United States Patent
Saito et al.

(10) Patent No.: US 10,378,070 B2
(45) Date of Patent: Aug. 13, 2019

(54) VECTOR AND GENE INTRODUCTION AGENT FOR MONITORING AND VISUALIZING CELL DIFFERENTIATION USING EXPRESSION OF MICRO RNA AS INDICATOR AND MONITORING AND VISUALIZING METHOD USING THEREOF

(71) Applicant: KYOTO UNIVERSITY, Kyoto (JP)

(72) Inventors: Hirohide Saito, Kyoto (JP); Hideyuki Nakanishi, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 15/697,831

(22) Filed: Sep. 7, 2017

(65) Prior Publication Data

US 2019/0071736 A1  Mar. 7, 2019

(51) Int. Cl.

| | |
|---|---|
| *C12N 5/00* | (2006.01) |
| *C12Q 1/48* | (2006.01) |
| *C12N 15/85* | (2006.01) |
| *C12N 15/86* | (2006.01) |
| *C12Q 1/6897* | (2018.01) |
| *G01N 33/50* | (2006.01) |

(52) U.S. Cl.
CPC ............ *C12Q 1/6897* (2013.01); *C12N 5/00* (2013.01); *C12N 15/85* (2013.01); *C12N 15/86* (2013.01); *C12Q 1/48* (2013.01); *G01N 33/5023* (2013.01); *G01N 2333/912* (2013.01)

(58) Field of Classification Search
CPC ........ C12Q 1/6897; C12Q 1/48; C12N 15/85; C12N 15/86
See application file for complete search history.

(56) References Cited

U.S. PATENT DOCUMENTS

2014/0315304 A1* 10/2014 Brown ................. C12N 5/0696
  435/372.3
2015/0315574 A1* 11/2015 Wilusz ................... A61K 48/00
  424/489
2017/0016077 A1  1/2017 Saito et al.

FOREIGN PATENT DOCUMENTS

| WO | WO-2011154553 A2 * | 12/2011 | .......... C12N 15/113 |
| WO | 2015/105172 | 7/2015 | |

OTHER PUBLICATIONS

Li et al. Dis. Model Mech. 6:828-33 (Year: 2013).*
Garcia-Silva et al. Genes 3:603-614 (Year: 2012).*
pVITRO1-GFP/LacZ, retrieved from the Internet on Jan. 17, 2019 at https://www.invivogen.com/pvitro1-gfplacz#details, Invivogen, 6 pages.
pLenti-C-Myc-DDK-IRES-Puro Tagged Cloning VectorpLenti-C-Myc-DDK-IRES-Puro Tagged Cloning Vector, Origene, retrieved from the Internet on Jan. 17, 2019 at https://www.origene.com/catalog/vectors/tagged-cloning-vectors/ps100069/plenti-c-myc-ddk-ires-puro-tagged-cloning-vector, 2 pages.

* cited by examiner

*Primary Examiner* — Brian Whiteman
(74) *Attorney, Agent, or Firm* — Myers Bigel, P.A.

(57) ABSTRACT

Provided is a method for continuously visualizing and accurately determining a living cellular state per se. Disclosed are: a vector comprising 5'- and 3'-end nucleic acid sequences for integration and a reporter gene sequence positioned between the 5'- and 3'-end nucleic acid sequences for integration; a gene introduction agent comprising a first vector and a second vector; a cell comprising the vector or the agent; and a method for determining a cellular state by using the cell.

7 Claims, 30 Drawing Sheets

Specification includes a Sequence Listing.

pDuReg2-tagRFP-hmAG1(92a-3p)

pDuReg2M-tagRFP-hmAG1(92a-3p)

pDuReg2MS-tagRFP-hmAG1(92a-3p)

- + hsa-miR-302a-5p inhibitor
- + Control inhibitor

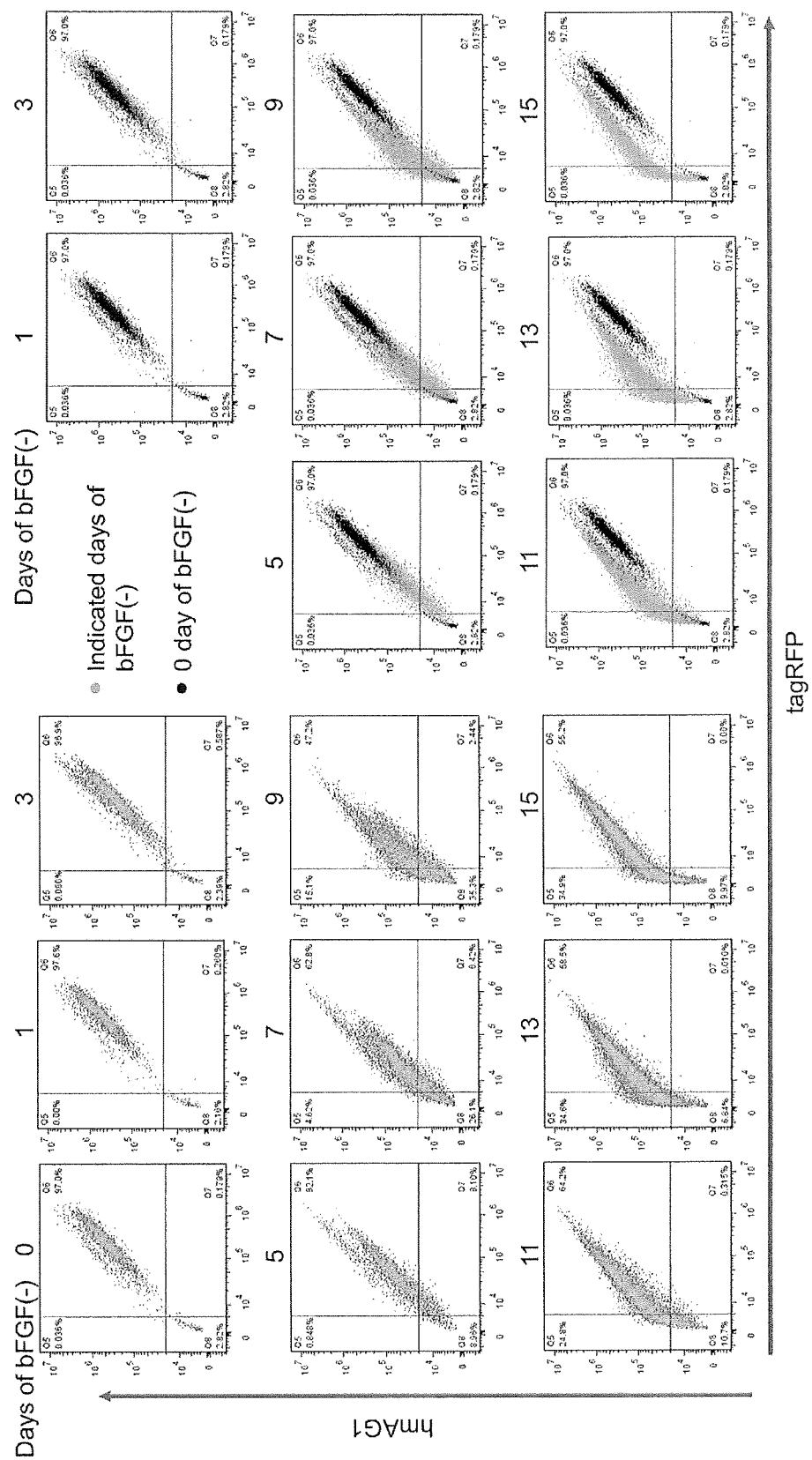

pCXEF1-TRE2MS-tagRFP-hmAG1(302a-5p)

pCXLE△-rtTA-puro

200 μm pCXEF1-TRE2MS-tagRFP-hmAG1(302a-5p) : pCXLE△-rtTA-puro = 1 : 1 pCXEF1-TRE2MS-tagRFP-hmAG1(302a-5p) : pCXLE△-rtTA-puro = 10 : 1

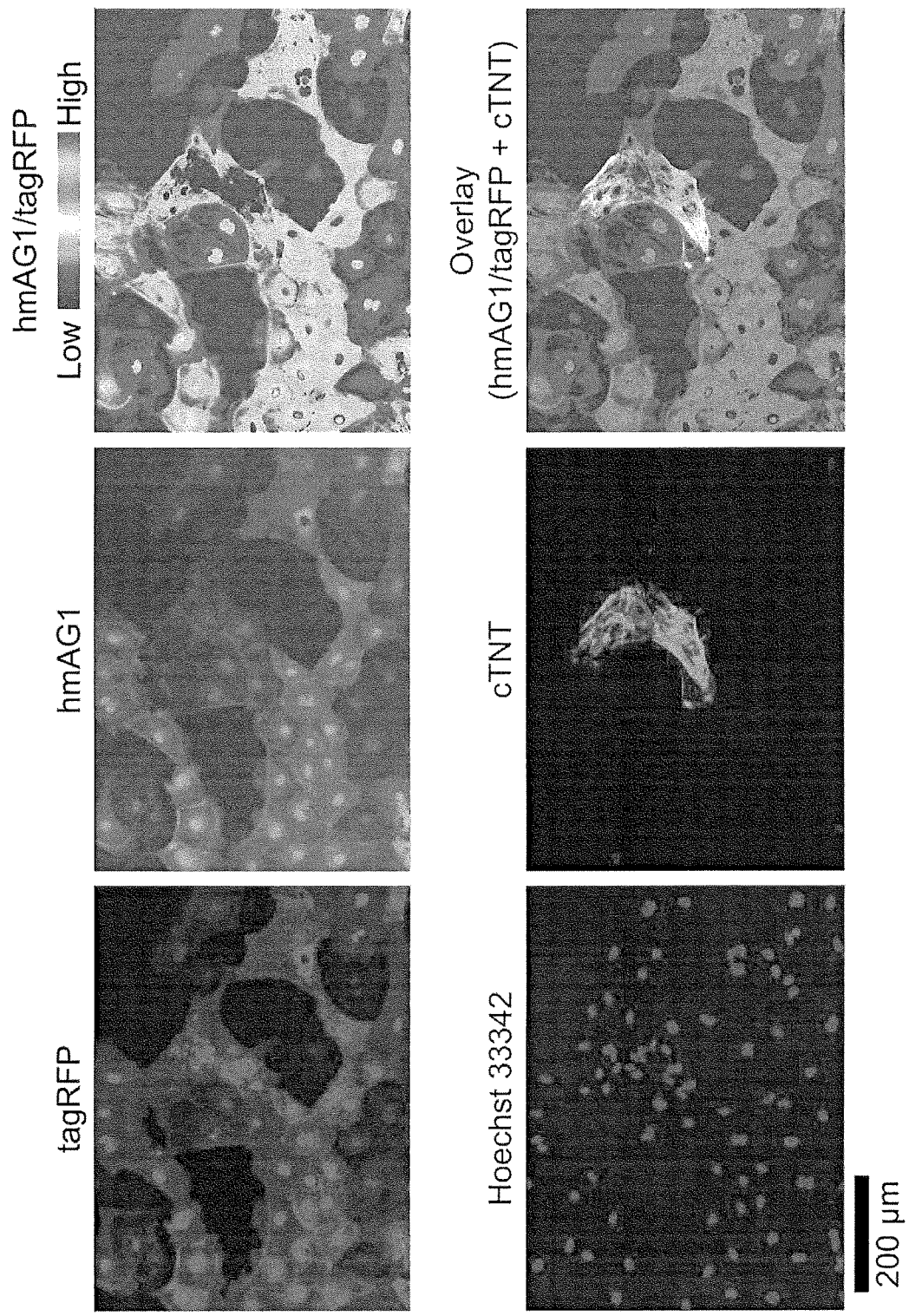

SEQUENCE LISTING

```
<160> NUMBER OF SEQ ID NOS: 51

<210> SEQ ID NO 1
<211> LENGTH: 110
<212> TYPE: DNA
<213> ORGANISM: Artificial Sequence
<220> FEATURE:
<223> OTHER INFORMATION: triple helix motif

<400> SEQUENCE: 1
gattcgtcag tagggttgta aaggtttttc ttttcctgag aaaacaacct tttgttttct      60
caggttttgc tttttggcct ttccctagct ttaaaaaaaa aaaagcaaaa                110

<210> SEQ ID NO 2
<211> LENGTH: 64
<212> TYPE: DNA
<213> ORGANISM: Artificial
<220> FEATURE:
<223> OTHER INFORMATION: RNaseP/Z cleavage site

<400> SEQUENCE: 2
gacgctggtg gctggcactc ctggtttcca ggacggggtt caagtccctg cggtgtcttt      60
gctt                                                                  64

<210> SEQ ID NO 3
<211> LENGTH: 94
<212> TYPE: DNA
<213> ORGANISM: Artificial
<220> FEATURE:
<223> OTHER INFORMATION: sno

<400> SEQUENCE: 3
tggatcgatg atgacttcca tatatacatt ccttggaaag ctgaacaaaa tgagtgaaaa      60
ctctataccg tcattctcgt cgaactgagg tcca                                  94
```

<210> SEQ ID NO 4
<211> LENGTH: 6
<212> TYPE: DNA
<213> ORGANISM: Artificial
<220> FEATURE:
<223> OTHER INFORMATION: polyA signal sequence

<400> SEQUENCE: 4 aataaa                                                                    6

<210> SEQ ID NO 5
<211> LENGTH: 28
<212> TYPE: DNA
<213> ORGANISM: Artificial
<220> FEATURE:
<223> OTHER INFORMATION: forward primer

<400> SEQUENCE: 5
ttctagaacg tgagatccgc ccctctcc                                           28

<210> SEQ ID NO 6
<211> LENGTH: 43
<212> TYPE: DNA
<213> ORGANISM: Artificial
<220> FEATURE:
<223> OTHER INFORMATION: reverse primer

<400> SEQUENCE: 6
aaaccggtgg cgcgcccatg gttgtggcca tattatcatc gtg                          43

<210> SEQ ID NO 7
<211> LENGTH: 38
<212> TYPE: DNA
<213> ORGANISM: Artificial
<220> FEATURE:
<223> OTHER INFORMATION: forward primer

<400> SEQUENCE: 7
gggcgcgccc agcgctgtga gcgtgatcaa gcccgaga                                38

<210> SEQ ID NO 8
<211> LENGTH: 31
<212> TYPE: DNA
<213> ORGANISM: Artificial
<220> FEATURE:
<223> OTHER INFORMATION: reverse primer

<400> SEQUENCE: 8
ccccgggtca cttggcctgg ctgggcagca t                                       31

<210> SEQ ID NO 9
<211> LENGTH: 41
<212> TYPE: DNA
<213> ORGANISM: Artificial
<220> FEATURE:
<223> OTHER INFORMATION: forward primer

<400> SEQUENCE: 9 cccctcgag gattcgtcag tagggttgta aaggtttttc t                             41

<210> SEQ ID NO 10
<211> LENGTH: 32
<212> TYPE: DNA
<213> ORGANISM: Artificial
<220> FEATURE:
<223> OTHER INFORMATION: reverse primer

```
<400> SEQUENCE: 10
ttctagaaag caaagacacc gcagggactt ga                           32

<210> SEQ ID NO 11
<211> LENGTH: 116
<212> TYPE: DNA
<213> ORGANISM: Artificial
<220> FEATURE:
<223> OTHER INFORMATION: MALAT1 TH sense

<400> SEQUENCE: 11
tcgaggattc gtcagtaggg ttgtaaaggt ttttcttttc ctgagaaaac aacctttgt     60 tttctcaggt tttgctttt ggcctttccc tagctttaaa aaaaaaaag caaaat         116

<210> SEQ ID NO 12
<211> LENGTH: 110
<212> TYPE: DNA
<213> ORGANISM: Artificial
<220> FEATURE:
<223> OTHER INFORMATION: MALAT1 TH antisense

<400> SEQUENCE: 12
ttttgctttt tttttttaa agctagggaa aggccaaaaa gcaaacctg agaaaacaaa     60 aggttgtttt ctcaggaaaa gaaaaacctt tacaaccta ctgacgaatc              110

<210> SEQ ID NO 13
<211> LENGTH: 29
<212> TYPE: DNA
<213> ORGANISM: Artificial
<220> FEATURE:
<223> OTHER INFORMATION: forward primer

<400> SEQUENCE: 13
gatatacgcg ttgacattga ttattgact                               29

<210> SEQ ID NO 14
<211> LENGTH: 37
<212> TYPE: DNA
<213> ORGANISM: Artificial
<220> FEATURE:
<223> OTHER INFORMATION: reverse primer

<400> SEQUENCE: 14 cccccctcgag tcaattaagt tgtgcccca gtttgct                       37

<210> SEQ ID NO 15
<211> LENGTH: 24
<212> TYPE: DNA
<213> ORGANISM: Artificial
<220> FEATURE:
<223> OTHER INFORMATION: hsa-miR-92a-3p target

<400> SEQUENCE: 15
ccacaggccg ggacaagtgc aata                                    24

<210> SEQ ID NO 16
<211> LENGTH: 24
<212> TYPE: DNA
<213> ORGANISM: Artificial
<220> FEATURE:
<223> OTHER INFORMATION: hsa-miR-92a-3p target antisense

<400> SEQUENCE: 16
tattgcactt gtcccggcct gtgg                                    24
```

```
<210> SEQ ID NO 17
<211> LENGTH: 99
<212> TYPE: DNA
<213> ORGANISM: Artificial
<220> FEATURE:
<223> OTHER INFORMATION: sno-lncRNA sense

<400> SEQUENCE: 17
ctagtggatc gatgatgact tccatatata cattccttgg aaagctgaac aaaatgagtg      60
aaaactctat accgtcattc tcgtcgaact gaggtccat                            99

<210> SEQ ID NO 18
<211> LENGTH: 99
<212> TYPE: DNA
<213> ORGANISM: Artificial
<220> FEATURE:
<223> OTHER INFORMATION: sno-lncRNA antisense

<400> SEQUENCE: 18
ctagatggac ctcagttcga cgagaatgac ggtatagagt tttcactcat tttgttcagc     60
tttccaagga atgtatatat ggaagtcatc atcgatcca                            99

<210> SEQ ID NO 19
<211> LENGTH: 38
<212> TYPE: DNA
<213> ORGANISM: Artificial
<220> FEATURE:
<223> OTHER INFORMATION: forward primer

<400> SEQUENCE: 19
ttctagaatt gttgttgtta acttgtttat tgcagctt                             38

<210> SEQ ID NO 20
<211> LENGTH: 27
<212> TYPE: DNA
<213> ORGANISM: Artificial
<220> FEATURE:
<223> OTHER INFORMATION: reverse primer

<400> SEQUENCE: 20
ccccaattgc cgcgctagca cgcgtca                                         27

<210> SEQ ID NO 21
<211> LENGTH: 24
<212> TYPE: DNA
<213> ORGANISM: Artificial
<220> FEATURE:
<223> OTHER INFORMATION: hsa-miR-302a-5p target

<400> SEQUENCE: 21
cagcaagtac atccacgttt aagt                                            24

<210> SEQ ID NO 22
<211> LENGTH: 24
<212> TYPE: DNA
<213> ORGANISM: Artificial
<220> FEATURE:
<223> OTHER INFORMATION: hsa-miR-302a-5p target antisense

<400> SEQUENCE: 22
acttaaacgt ggatgtactt gctg                                            24
```

```
<210> SEQ ID NO 23
<211> LENGTH: 22
<212> TYPE: DNA
<213> ORGANISM: Artificial
<220> FEATURE:
<223> OTHER INFORMATION: forward primer

<400> SEQUENCE: 23
caccatggga tccgtgtcta ag                                          22

<210> SEQ ID NO 24
<211> LENGTH: 24
<212> TYPE: DNA
<213> ORGANISM: Artificial
<220> FEATURE:
<223> OTHER INFORMATION: reverse primer

<400> SEQUENCE: 24
tcacttggcc tggctgggca gcat                                        24

<210> SEQ ID NO 25
<211> LENGTH: 54
<212> TYPE: DNA
<213> ORGANISM: Artificial
<220> FEATURE:
<223> OTHER INFORMATION: hsa-miR-1-3p target

<400> SEQUENCE: 25
atgggcgcgc ccagcataca tacttcttta cattccaccg ctgtgagcgt gatc       54

<210> SEQ ID NO 26
<211> LENGTH: 54
<212> TYPE: DNA
<213> ORGANISM: Artificial
<220> FEATURE:
<223> OTHER INFORMATION: hsa-miR-208a-3p target

<400> SEQUENCE: 26
atgggcgcgc ccagccacaa gcttttttgct cgtcttatcg ctgtgagcgt gatc      54

<210> SEQ ID NO 27
<211> LENGTH: 35
<212> TYPE: DNA
<213> ORGANISM: Artificial
<220> FEATURE:
<223> OTHER INFORMATION: forward primer

<400> SEQUENCE: 27
acaaccatgg gcgcgcctgt gagcgtgatc aagcc                            35

<210> SEQ ID NO 28
<211> LENGTH: 50
<212> TYPE: DNA
<213> ORGANISM: Artificial
<220> FEATURE:
<223> OTHER INFORMATION: reverse primer

<400> SEQUENCE: 28
agctgggtcg gcgcgactag tttgtcgacg cgtcacttgg cctggctggg            50

<210> SEQ ID NO 29
<211> LENGTH: 34
<212> TYPE: DNA
<213> ORGANISM: Artificial
<220> FEATURE:
<223> OTHER INFORMATION: forward primer
```

<400> SEQUENCE: 29
gcaggctccg cggccgacgt gagatccgcc cctc    34

<210> SEQ ID NO 30
<211> LENGTH: 36
<212> TYPE: DNA
<213> ORGANISM: Artificial
<220> FEATURE:
<223> OTHER INFORMATION: reverse primer

<400> SEQUENCE: 30
ggcgaccggt ggatccatgg ttgtggccat attatc    36

<210> SEQ ID NO 31
<211> LENGTH: 34
<212> TYPE: DNA
<213> ORGANISM: Artificial
<220> FEATURE:
<223> OTHER INFORMATION: forward primer

<400> SEQUENCE: 31
caagtgacgc gtcgagattc gtcagtaggg ttgt    34

<210> SEQ ID NO 32
<211> LENGTH: 33
<212> TYPE: DNA
<213> ORGANISM: Artificial
<220> FEATURE:
<223> OTHER INFORMATION: reverse primer

<400> SEQUENCE: 32
cgactagttt gtcgaaagca aagacaccgc agg    33

<210> SEQ ID NO 33
<211> LENGTH: 31
<212> TYPE: DNA
<213> ORGANISM: Artificial
<220> FEATURE:
<223> OTHER INFORMATION: forward primer

<400> SEQUENCE: 33
aaaggatccc gtgtctaagg gcgaagagct g    31

<210> SEQ ID NO 34
<211> LENGTH: 32
<212> TYPE: DNA
<213> ORGANISM: Artificial
<220> FEATURE:
<223> OTHER INFORMATION: reverse primer

<400> SEQUENCE: 34
ttctagaaag caaagacacc gcagggactt ga    32

<210> SEQ ID NO 35
<211> LENGTH: 98
<212> TYPE: DNA
<213> ORGANISM: Artificial
<220> FEATURE:
<223> OTHER INFORMATION: P2A

<400> SEQUENCE: 35
tgtgggctgg gcgcgggtcc agggttctcc tccacgtctc cagcctgctt cagcaggctg    60
aagttagtag ctccgcttcc gacgttgatc ctggcgct    98

```
<210> SEQ ID NO 36
<211> LENGTH: 39
<212> TYPE: DNA
<213> ORGANISM: Artificial
<220> FEATURE:
<223> OTHER INFORMATION: forward primer

<400> SEQUENCE: 36
acaaccatgg gcgcggtata cggaagcgga gctactaac                   39

<210> SEQ ID NO 37
<211> LENGTH: 33
<212> TYPE: DNA
<213> ORGANISM: Artificial
<220> FEATURE:
<223> OTHER INFORMATION: reverse primer

<400> SEQUENCE: 37
acgctcacag gcgcgggtcc agggttctcc tcc                         33

<210> SEQ ID NO 38
<211> LENGTH: 24
<212> TYPE: DNA
<213> ORGANISM: Artificial
<220> FEATURE:
<223> OTHER INFORMATION: hsa-miR-302a-5p target

<400> SEQUENCE: 38
cagcaagtac atccacgttt aagt                                   24

<210> SEQ ID NO 39
<211> LENGTH: 24
<212> TYPE: DNA
<213> ORGANISM: Artificial
<220> FEATURE:
<223> OTHER INFORMATION: hsa-miR-302a-5p target antisense

<400> SEQUENCE: 39
acttaaacgt ggatgtactt gctg                                   24

<210> SEQ ID NO 40
<211> LENGTH: 78
<212> TYPE: DNA
<213> ORGANISM: Artificial
<220> FEATURE:
<223> OTHER INFORMATION: hsa-miR-302a-5p H2

<400> SEQUENCE: 40
accatgggcg cggtacacga gtttatcgag caagtacatc cacgtttaag tgtgtacctc   60
gtgtacggaa gcggagct                                               78

<210> SEQ ID NO 41
<211> LENGTH: 90
<212> TYPE: DNA
<213> ORGANISM: Artificial
<220> FEATURE:
<223> OTHER INFORMATION: hsa-miR-302a-5p D4

<400> SEQUENCE: 41
accatgggcg cggtatcgag ataccgcgcc ttcgagaagc aagtacatcc acgtttaagt   60
cgcttccgtg atgattacgg aagcggagct                                   90
```

<210> SEQ ID NO 42
<211> LENGTH: 36
<212> TYPE: DNA
<213> ORGANISM: Artificial
<220> FEATURE:
<223> OTHER INFORMATION: forward primer

<400> SEQUENCE: 42
ttttggcaaa gaattgccac catgtctaga ctggac					36

<210> SEQ ID NO 43
<211> LENGTH: 33
<212> TYPE: DNA
<213> ORGANISM: Artificial
<220> FEATURE:
<223> OTHER INFORMATION: reverse primer

<400> SEQUENCE: 43
cccgaagctt gaatttcagg caccgggctt gcg					33

<210> SEQ ID NO 44
<211> LENGTH: 28
<212> TYPE: DNA
<213> ORGANISM: Artificial
<220> FEATURE:
<223> OTHER INFORMATION: forward primer

<400> SEQUENCE: 44
aacctgcagg ggctccggtg cccgtcag					28

<210> SEQ ID NO 45
<211> LENGTH: 64
<212> TYPE: DNA
<213> ORGANISM: Artificial
<220> FEATURE:
<223> OTHER INFORMATION: reverse primer

<400> SEQUENCE: 45
aaacctaggc catttccagg tcctgtacct ggccctcgt cagacatggt ggcgaccggt			60 ggat									64

<210> SEQ ID NO 46
<211> LENGTH: 33
<212> TYPE: DNA
<213> ORGANISM: Artificial
<220> FEATURE:
<223> OTHER INFORMATION: forward primer

<400> SEQUENCE: 46
ataaatcccc agtaggatca gcctcgactg tgc					33

<210> SEQ ID NO 47
<211> LENGTH: 33
<212> TYPE: DNA
<213> ORGANISM: Artificial
<220> FEATURE:
<223> OTHER INFORMATION: reverse primer

<400> SEQUENCE: 47
gcacgcatga tgtctgccat agagcccacc gca					33

<210> SEQ ID NO 48
<211> LENGTH: 21
<212> TYPE: DNA
<213> ORGANISM: Artificial

```
<220> FEATURE:
<223> OTHER INFORMATION: forward primer

<400> SEQUENCE: 48
cgcaaatggg cggtaggcgt g                                               21

<210> SEQ ID NO 49
<211> LENGTH: 33
<212> TYPE: DNA
<213> ORGANISM: Artificial
<220> FEATURE:
<223> OTHER INFORMATION: reverse primer

<400> SEQUENCE: 49
aaaggatcca ggaaccgtaa aaaggccgcg ttg                                  33

<210> SEQ ID NO 50
<211> LENGTH: 34
<212> TYPE: DNA
<213> ORGANISM: Artificial
<220> FEATURE:
<223> OTHER INFORMATION: forward primer

<400> SEQUENCE: 50
atcgcctgga gaattcgaca ccatgggatc cgtg                                 34

<210> SEQ ID NO 51
<211> LENGTH: 36
<212> TYPE: DNA
<213> ORGANISM: Artificial
<220> FEATURE:
<223> OTHER INFORMATION: reverse primer

<400> SEQUENCE: 51
gctagcacgc gtcagctgtc acttggcctg gctggg                               36
```

VECTOR AND GENE INTRODUCTION AGENT FOR MONITORING AND VISUALIZING CELL DIFFERENTIATION USING EXPRESSION OF MICRO RNA AS INDICATOR AND MONITORING AND VISUALIZING METHOD USING THEREOF

STATEMENT REGARDING ELECTRONIC FILING OF A SEQUENCE LISTING

A Sequence Listing in ASCII text format, submitted under 37 C.F.R. § 1.821, entitled 5576-338_ST25.txt, 10,479 bytes in size, generated on Jan. 29, 2018, and filed via EFS-Web, is provided in lieu of a paper copy. This Sequence Listing is hereby incorporated by reference into the specification for its disclosures.

TECHNICAL FIELD

The present invention relates to vectors and gene introduction agents for continuously visualizing cell differentiation by using expression of a miRNA as an indicator, and a visualizing method using the same.

BACKGROUND ART

Multicellular organisms have tissues and organs composed of different types of cells. Each human has $3.7 \times 10^{13}$ cells and the number of types of mature cells reaches 411. It has become increasingly important to provide a technology used to not only analyze functions of individual cells, but also distinguish and identify the type of each cell when the relevant cells are prepared for medical applications.

The present inventors have developed miRNA-responsive mRNAs, which express proteins in response to an intracellular microRNA(s) (hereinafter, referred to as miRNA), thereby providing a method for distinguishing a desired type of cell from another by using, as an indicator, expression of the miRNA (e.g., Patent Literature 1).

PRIOR ART DOCUMENT

Patent Literature

[Patent Literature 1] WO2015/105172

SUMMARY OF INVENTION

Problems to be Solved by the Invention

After a miRNA-responsive mRNA is prepared and transfected into cells, intracellular miRNA activity at the time of the transfection can be examined and the cellular state can then be revealed. In addition, RNA does not cause a problem such as genomic integration of an exogenous gene, so that use of RNA has such an advantage that the cells containing a miRNA-responsive mRNA can be applied clinically as they are. Meanwhile, when a target type of cells is differentiated from pluripotent stem cells such as iPS cells, the resulting cell population may contain undifferentiated cells and/or other types of cells. To select the target type of cells, it is necessary to continuously visualize the differentiation status of each cell. Unfortunately, no technique has been established which can be used to continuously examine, without using a virus, miRNA activity in live cell conditions.

Thus, a method has been sought in which a cellular state can be distinguished by continuously visualizing, with high precision, a cellular state in live cell conditions.

Means for Solving the Problems

The present inventors have found that a piggyBac transposon vector or an episomal plasmid vector can be used to introduce, into cells, a sequence that can generate an miRNA-responsive mRNA, thereby continuously monitoring the miRNA activity. The present invention was thereby completed.

Specifically, the present invention provides the following items.

[1] A vector comprising
(I) 5'- and 3'-end nucleic acid sequences for integration to be recognized by a transposase and
(II) a reporter gene sequence positioned between the 5'- and 3'-end nucleic acid sequences for integration, the reporter gene sequence comprising: in this order in the 5' to 3' direction, a) an inducible promoter; b) a sequence encoding a first marker protein; c) a poly(A) substitute sequence; d) an RNaseP/Z cleavage site sequence; e) an mRNA-stabilizing sequence; f) a sequence to drive polycistronic expression; g) an miRNA target sequence; h) a sequence encoding a second marker protein; i) a poly(A) substitute sequence and an RNaseP/Z cleavage site sequence, or a poly(A) signal sequence; and j) a sequence encoding an activator for the inducible promoter.

[2] The vector according to item [1], wherein the reporter gene sequence further comprises k) a strong expression promoter linked on the 3' end side of i) the poly(A) substitute sequence and on the 5' end side of j) the sequence encoding an activator for the inducible promoter.

[3] The vector according to item [1] or [2], wherein the reporter gene sequence further comprises, in this order in the 5' to 3' direction, l) a sequence to drive polycistronic expression and m) a drug resistance sequence, linked on the 3' end side of j) the sequence encoding an activator for the inducible promoter.

[4] A gene introduction agent comprising: (I) a first vector comprising, in this order in the 5' to 3' direction, (a) an inducible promoter; b) a sequence encoding a first marker protein; c) a poly(A) substitute sequence; d) an RNaseP/Z cleavage site sequence; e) an mRNA-stabilizing sequence; f) a sequence to drive polycistronic expression; g) an miRNA target sequence; h) a sequence encoding a second marker protein; l) EBNA1 gene, and m) a replication origin OriP; and (II) a second vector comprising, in this order in the 5' to 3' direction, (n) a strong expression promoter and (o) a sequence encoding an activator for the inducible promoter.

[5] The gene introduction agent according to item [4], wherein the first vector further comprises, in this order in the 5' to 3' direction, i) WPRE and k) a strong expression promoter, linked on the 3' end side of h) the sequence encoding a second marker protein and on the 5' end side of l) the EBNA1 gene; and/or
wherein the second vector further comprises, in this order in the 5' to 3' direction, p) a sequence to drive polycistronic expression, q) a drug resistance sequence, r) WPRE, and s) a replication origin OriP, linked on the 3' end side of o) the sequence encoding an activator for the inducible promoter.

[6] The gene introduction agent according to item [4] or [5], wherein the first vector further comprises, in this order in the 5' to 3' direction, t) ColE1Ori and u) a drug resistance sequence, linked on the 3' end side of m) the sequence encoding an activator for the inducible promoter; and/or wherein the second vector further comprises, in this order in the 5' to 3' direction, v) ColE1Ori and w) a drug resistance sequence, linked on the 3' end side of s) the replication origin OriP.

[7] A cell stably expressing an miRNA-responsive mRNA, wherein the cell has introduced therein:
a) the vector according to any one of items [1] to [3] and a transposase or a vector encoding the transposase; or
b) the gene introduction agent according to any one of items [4] to [6].

[8] A method for visualizing a differentiation status of a cell, the method comprising the steps of:
(I) introducing, into the cell, a) the vector according to any one of items [1] to [3] and a transposase or a vector encoding the transposase or b) the gene introduction agent according to any one of items [4] to [6]; and
(II) determining the differentiation status of the cell by using, as indicators, a level of translation of the first marker protein and a level of translation of the second marker protein.

[9] The method according to item [8], wherein the cell is a cell differentiated from a pluripotent stem cell.

[10] The method according to item [8] or [9], wherein the introduction step comprises introducing, into a cell population, a) the vector according to any one of items [1] to [3] and a transposase or a vector encoding the transposase; and wherein the method further comprises, after the cell differentiation status determination step, (III) introducing, into the cell population, the transposase or the vector encoding the transposase, thereby removing the reporter gene sequence from a genome of the cell.

Advantageous Effects of Invention

The present invention can provide a vector or gene introduction agent that can be transfected into a cell to continuously and stably express an miRNA-responsive reporter gene. In this system, an mi-RNA-activity-independent first marker protein-expressing gene and an miRNA-activity-responsive second marker protein-expressing gene are transcribed in a single messenger RNA from the identical promoter. Thus, the level of translation repression can be accurately determined using a ratio of the level of translation of the second marker protein to the level of translation of the first marker protein. This makes it possible to continuously and precisely distinguish a cellular state based on the miRNA activity.

BRIEF DESCRIPTION OF DRAWINGS

FIG. 1 illustrates vector designs for monitoring miRNA activity. First, $1 \times 10^5$ 293 FT cells were co-transfected with pcDNA3.1-ECFP (200 ng; used as an indicator for transfection efficiency) and the indicated miRNA reporter vector (400 ng) in addition to an hsa-miR-92a-3p inhibitor or a negative control (3 nM). One day after the transfection, the level of expression of each fluorescent protein was measured with a flow cytometer.

In FIG. 1B, the red histograms represent the fluorescence levels in the hsa-miR-92a-3p inhibitor-containing cells. In contrast, the black histograms represent the fluorescence levels in the negative control-containing cells.

In FIG. 1C, the green histograms represent the fluorescence levels in the hsa-miR-92a-3p inhibitor-containing cells. In contrast, the black histograms represent the fluorescence levels in the negative control-containing cells.

In FIG. 1D, the green histograms represent the fluorescence levels in the hsa-miR-92a-3p inhibitor-containing cells. In contrast, the black histograms represent the fluorescence levels in the negative control-containing cells.

FIG. 2 illustrates how to establish stable reporter human iPS cells (hiPSCs) for hsa-miR-302a-5p. HiPSCs (201B7 strain) were co-transfected with a piggyBac-based miRNA reporter vector and pCAG-HyAcPBase. The cells containing these vectors were cultured in puromycin-containing medium to give cells in which the reporter vector was integrated into the genome. Either the hsa-miR-302a-5p inhibitor or the negative control (30 nM) was transfected into the resulting stable reporter cells. These cells were further treated with 2000 ng/ml (FIG. 2B) or from 0 to 2000 ng/ml (FIG. 2C) of doxycycline to induce expression of the fluorescent proteins. One day after the inhibitor transfection, the levels of expression of tag RFP and hmAG1 were measured with a flow cytometer.

FIG. 3 shows the results of flow cytometry-based monitoring of hsa-miR-302a-5p activity during differentiation induced by removal of bFGF from medium. Stable reporter hiPSCs for hsa-miR-302a-5p were cultured in bFGF-free medium to induce spontaneous differentiation. One day before the flow cytometry, doxycycline (1000 ng/ml) was added to the cells. At each indicated time point in the diagram, the levels of expression of tagRFP and hmAG1 were measured with a flow cytometer.

FIG. 3B contains the 9 left plots, which are each a 2D dot plot showing the levels of fluorescence of tagRFP and hmAG1, and the 8 right plots in which the plot at day 0 is superimposed on each of the plots at the other time points. Black and green dots indicate the levels at day 0 and the indicated days after bFGF removal, respectively.

FIG. 4A shows a decrease in the hsa-miR-302a-5p activity during spontaneous differentiation. The spontaneous differentiation was likewise induced by using the procedure of FIG. 3 and fluorescent microscopic images were captured at the indicated days after bFGF removal.

FIG. 5 shows differentiation monitoring by using an miRNA-responsive reporter episomal vector.

FIG. 6 shows improvement of miRNA sensitivity by optimizing the RNA secondary structures or increasing the copy number of miRNA target sites. Reporters with 1 to 4 copies of hsa-miR-302a-5p target sites were integrated into the genomes of hiPSCs, and the resulting stable reporter cells were cultured in bFGF-free medium to induce spontaneous differentiation.

FIG. 7 shows detection of hsa-miR-208a-3p and hsa-miR-1-3p activity after cardiac differentiation, and separation and purification of cardiomyocytes. Stable reporter hiPSCs for hsa-miR-208a-3p or hsa-miR-1-3p were forced to differentiate into cardiomyocytes. One day before flow cytometry, cells were treated with doxycycline (500 ng/ml).

FIG. 10 shows time-lapse imaging of spontaneous differentiation. Stable reporter hiPSCs were cultured in bFGF-free, doxycycline (1000 ng/ml)-containing medium. On day 5, cells were detached from a plate and re-seeded. From days 6 to 11, fluorescent microscopic images of tagRFP and hmAG1 were captured every 3 h. FIG. 4B presents images in which the hmAG1.tagRFP ratio was visualized.

In FIG. 13, fluorescence microscopy was used to analyze differentiation by using reporter vectors having low access energy or multiple hsa-miR-302a-5p target sequences.

In FIG. 14, fluorescence microscopy was used to analyze cardiac differentiation. An hsa-miR-208a-3p-responsive reporter vector was integrated into hiPSCs, and the resulting cells were forced to differentiate into cardiomyocytes. After the differentiation, the cells were fixed and stained with an anti-cTNT antibody. The hmAG1/tagRFP ratio represents hsa-miR-208a-3p activity.

DESCRIPTION OF EMBODIMENTS

Figure 1A:
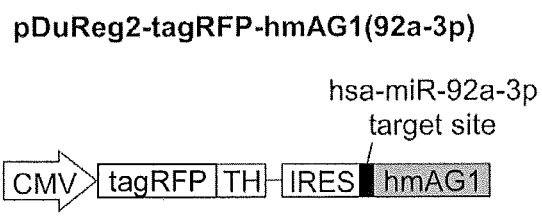
FIG. 1A is a schematic diagram regarding plasmid vector designs. CMV indicates a cytomegalovirus promoter for transcribing tagRFP and hmAG1 genes; tagRFP indicates red fluorescent protein tagRFP gene; TH indicates a MALAT-1 long non-coding RNA-derived triple helix motif, which helps stabilize and translate the tagRFP messenger RNA; IRES indicates an encephalomyocarditis virus-derived internal ribosome entry site for the translation of hmAG1; hmAG1 indicates a monomeric Azami Green (green fluorescent protein) gene optimized for human codon; and Sno indicates small nuclear RNA-like long non-coding RNA-derived end protection motif added so as to stabilized the hmAG1 messenger RNA.
Figure 1A:
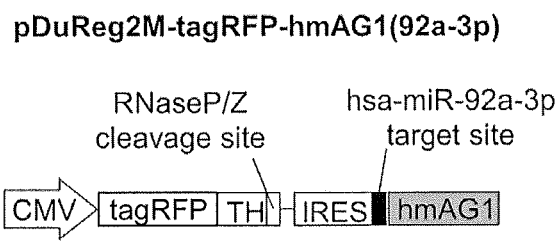
Figure 1A:
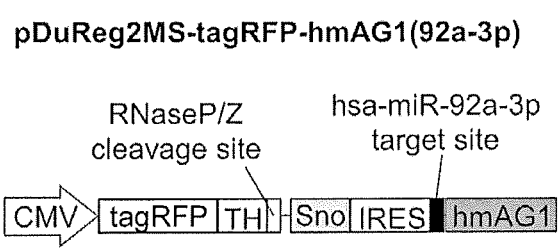
Figure 1B:
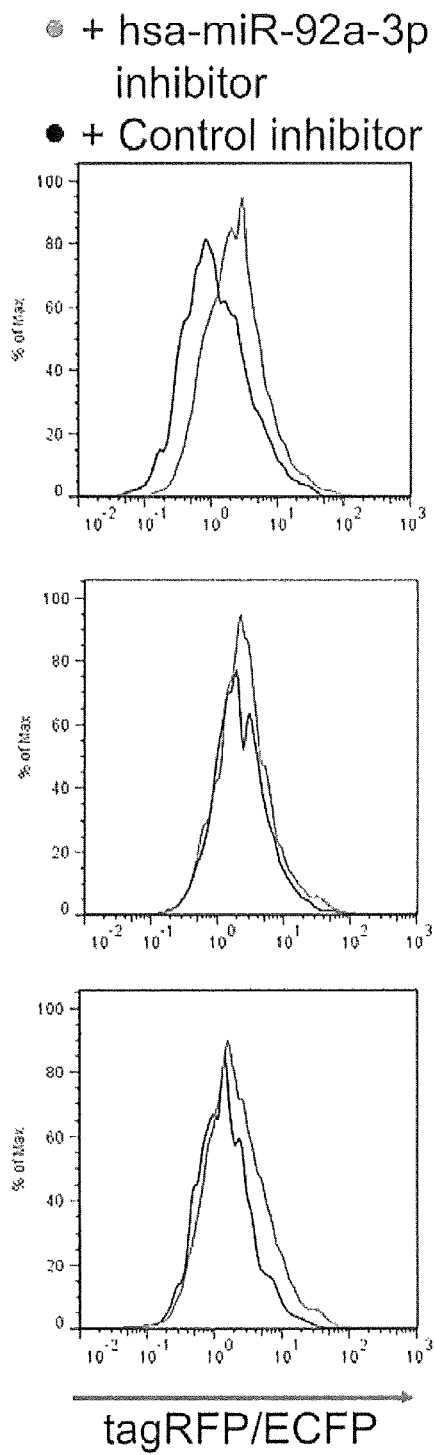
FIG. 1B is fluorescence histograms of the respective fluorescent proteins in tagRFP-positive and hmAG1-positive cells.

The following describes, in detail, embodiments of the present invention. The present invention, however, is not limited to these embodiments.

First Embodiment: PiggyBac Transposon-Based Vector

A first embodiment of the present invention provides a piggyBac transposon-based vector. Specifically, provided is a vector comprising:

(I) 5'- and 3'-end nucleic acid sequences for integration to be recognized by a transposase and (II) a reporter gene sequence positioned between the 5'- and 3'-end nucleic acid sequences for integration, the reporter gene sequence comprising: in this order in the 5' to 3' direction, a) an inducible promoter; b) a sequence encoding a first marker protein; c) a poly(A) substitute sequence; d) an RNaseP/Z cleavage site sequence; e) an mRNA-stabilizing sequence; f) a sequence to drive polycistronic expression; g) an miRNA target sequence; h) a sequence encoding a second marker protein; i) a poly(A) substitute sequence and an RNaseP/Z cleavage site sequence, or a poly(A) signal sequence; and j) a sequence encoding an activator for the inducible promoter.

A vector according to this embodiment, together with a transposase, is transfected into cells, in which the vector is transcribed, under control of a single inducible promoter, in a single mRNA including a first marker protein-encoding sequence, a miRNA target sequence, and a second marker protein-encoding sequence. A DNA sequence that is cut out by the transposase and is then integrated according to this embodiment is sometimes referred to as a reporter gene sequence or a miRNA-responsive reporter gene.

(I) 5'- and 3'-end nucleic acid sequences for integration may be inverted repeat sequences specifically recognized by a specific transposase. Preferable examples of the inverted repeat sequence include piggyBac, which is a transposon derived from a moth. Regarding the piggyBac transposon, a nucleic acid sequence positioned between the 5'- and 3'-end nucleic acid sequences for integration is first integrated in a chromosome of a cell. Then, the nucleic acid sequence of interest can be removed from the chromosome by using the transposase. Kaji, K. et al., Nature, 458: 771-775 (2009) and Woltjen et al., Nature, 458: 766-770 (2009) disclose technologies for integrating a nucleic acid sequence into a chromosome and removing the nucleic acid sequence from the chromosome by using the piggyBac transposon.

(II) In the reporter gene sequence, the above sequences a) to j) are linked in this order in the 5' to 3' direction. Optionally, k) the strong expression promoter may be linked, in this order in the 5' to 3' direction, on the 3' end side of the sequence i) and on the 5' end side of the sequence j). Further optionally, l) the sequence to drive polycistronic expression and m) the drug resistance sequence may be linked, in this order in the 5' to 3' direction, on the 3' end side of j) the sequence encoding an activator for the inducible promoter. As used herein, the phrase "a first element (sequence) is positioned on the "5' end side" of a second element (sequence)" means that the first element is positioned at least upstream of, namely on the 5' end side of the second element (e.g., any of a) to m) constituting the reporter gene sequence). However, the two do not have to be in contact with each other and another element or a nucleotide sequence may be interposed therebetween. Likewise, the phrase "a first element (sequence) is positioned on the "3' end side" of a second element (sequence)" means that the first element is positioned at least downstream of, namely on the 3' end side of the second element (e.g., any of the elements a) to m) constituting the reporter gene sequence). However, the two do not have to be in contact with each other and another element or a nucleotide sequence may be interposed therebetween. For instance, a sequence containing several dozen nucleotides may be present between the sequences a) and b) and a nucleotide sequence may be present between the sequences i) and k).

a) The inducible promoter drives transcription of a gene under control of the promoter in given induction conditions. Examples of the inducible promoter include, but are not limited to, tetracycline responsive element (TRE) promoter or derivatives thereof.

b) The sequence encoding a first marker protein encodes a protein that can function as a marker after translation in a cell. The protein may be, for example, a fluorescent protein, a light-emitting protein, or a chromogenic protein, or may help emit fluorescence, light, or color for visualization and quantification. Examples of the fluorescent protein include, but are not limited to, blue fluorescent proteins (e.g., Sirius, EBFP); cyan fluorescent proteins (e.g., mTurquoise, TagCFP, AmCyan, mTFP1, MidoriishiCyan, CFP); green fluorescent proteins (e.g., TurboGFP, AcGFP, TagGFP, Azami-Green (e.g., hmAG1), ZsGreen, EmGFP, EGFP, GFP2, HyPer); yellow fluorescent proteins (e.g., TagYFP, EYFP, Venus, YFP, PhiYFP, PhiYFP-m, TurboYFP, ZsYellow, mBanana); orange fluorescent proteins (e.g., KusabiraOrange (e.g., hmKO2), mOrange); red fluorescent proteins (e.g., TurboRFP, DsRed-Express, DsRed2, TagRFP, DsRed-Monomer, AsRed2, mStrawberry); and near-infrared fluorescent proteins (e.g., TurboFP602, mRFP1, JRed, KillerRed, mCherry, HcRed, KeimaRed (e.g., hdKeimaRed), mRasberry, mPlum). Examples of the light-emitting protein include, but are not limited to, Aequorin. In addition, examples of the protein that helps emit fluorescence, light, or color include, but are not limited to, enzymes (e.g., a luciferase, phosphatase, peroxidase, β-lactamase) that help convert fluorescent, light-emitting, or chromogenic precursors. As used herein, when a protein that helps emit fluorescence, light, or color is used as a protein encoded by a marker gene, a relevant precursor is made to contact a cell or the relevant precursor is introduced into the cell during target cell determination.

Examples of c) the poly(A) substitute sequence include MALAT-1 long non-coding RNA-derived triple helix motif (J. E. Wilusz et al., Genes Dev. 26 (2012), 2392-2407). This sequence makes it possible to help translation of a first marker protein because the sequence stabilizes the corresponding mRNA even after RNA-induced silencing complex (RISC) cleaves the mRNA at the position of the miRNA target sequence g) and the resulting mRNA thus loses the poly(A). The triple helix motif (also, referred to as TH) may be a sequence comprising (SEQ ID NO: 1)
gattcgtcagtagggttgtaaaggtttttcttttcctgagaaaacaacc
ttttgttttctcaggattgcttttggcctttccctagctttaaaaaaa
aaaaagcaaaa.

d) The RNaseP/Z cleavage site sequence is a sequence to be cleaved by RNaseP and RNaseZ. Specific examples of the sequence include a sequence comprising (SEQ ID NO: 2)
gacgctggtggctggcactcctggtttccaggacggggttcaagtccct
gcggtgtattgctt.

As e) the mRNA-stabilizing sequence, small nuclear RNA-like long non-coding RNA-derived end protection motif (sno: Q. F. Yin et al., Mol. Cell. 48 (2012), 219-230) may be used. The sno sequence may be a sequence comprising (SEQ ID NO: 3)
tggatcgatgatgacttccatatatacattccttggaaagctgaacaaa
atgagtgaaaactctataccgtcattctcgtcgaactgaggtcca.

f) The sequence to drive polycistronic expression can be used to efficiently express a plurality of genes cloned in a single expression vector. Example of the sequence to drive polycistronic expression include, but are not limited to, foot-and-mouth disease virus 2A sequence (PLoS ONE 3, e2532, 2008, Stem Cells 25, 1707, 2007) and IRES(s) (U.S. Pat. No. 4,937,190).

g) The miRNA target sequence is a nucleic acid sequence specifically recognized by an intracellular miRNA. As used herein, the "miRNA" refers to a non-coding RNA composed of a short chain (20 to 25 nucleotides) that is present in a cell and is participated in the regulation of gene expression through mRNA degradation and/or repression of translation from an mRNA to a protein. This miRNA is produced first as a transcribed, single-stranded pri-miRNA, an miRNA of which, together with its complementary strand, can form a hairpin loop structure; a portion of the pri-miRNA is cleaved by an enzyme called Drosha present in the nucleus to give a pre-miRNA, which is exported outside the nucleus; and the pre-miRNA is further cleaved by Dicer to become functional.

As the miRNA, it is possible to suitably select a miRNA that is expressed specifically in a specific type of cell to be determined or a miRNA that is not expressed in a specific type of cell to be determined. The specifically expressed miRNA is represented by miRNAs, the expression levels of which are higher in a specific type of cell than in another type of cell by 10% or more, 20% or more, 30% or more, 40% or more, 50% or more, 60% or more, 70% or more, 80% or more, or 90% or more. Such a miRNA can be suitably selected from miRNAs registered on database information site (e.g., www.mirbase.org/ or www.microrna.org/) and/or miRNAs described in literatures disclosed in the database.

In the present invention, the nucleic acid sequence specifically recognized by a miRNA is preferably a sequence perfectly complementary to the miRNA. Alternatively, the nucleic acid sequence may have a mismatch in the perfectly complementary sequence as long as the nucleic acid sequence can be recognized by the miRNA. The mismatch in the sequence perfectly complementary to the miRNA may be a mismatch that the miRNA can usually recognize. Regarding in vivo, intracellular, intrinsic functions, the degree of the mismatch may be about 40 to 50%. Examples of such a mismatch include, but are not particularly limited to, 1 nucleotide, 2 nucleotides, 3 nucleotides, 4 nucleotides, 5 nucleotides, 6 nucleotides, 7 nucleotides, 8 nucleotides, 9 nucleotides, and 10 nucleotides; or 1% mismatch, 5% mismatch, 10% mismatch, 20% mismatch, 30% mismatch, and 40% mismatch per entire recognition sequence. In addition, like a miRNA target sequence included in a certain mRNA in a cell, many mismatches may be included in the 5' region of a target sequence, which region is outside a seed region and corresponds to about 16 nucleotides located on the 3' end side of the miRNA. The seed region may contain no mismatch or contain mismatches: 1 nucleotide, 2 nucleotides, or 3 nucleotides. The length of such a sequence may be a nucleotide length corresponding to the number of nucleotides that can bind specifically to RISC. The length of the sequence is preferably 18 nucleotides or more and 24 nucleotides or less and more preferably 20 nucleotides or more and 22 nucleotides or less.

The miRNA target site includes one, two, three, four, or more copies of a nucleic acid sequence specifically recognized by a miRNA. It is preferable that the miRNA target site be provided with a plurality of the nucleic acid sequences specifically recognized by a miRNA because the miRNA target site has increased sensitivity to the intracellular miRNA.

h) The sequence encoding a second marker protein can be selected from substantially the same choices as of b) the sequence encoding the first marker protein and encodes a marker protein different from the second marker protein.

As the sequence i), either a poly(A) substitute sequence and a RNaseP/Z cleavage site sequence, or a poly(A) signal sequence can be used. When the sequence i) is the poly(A) substitute sequence and the RNaseP/Z cleavage site sequence, the poly(A) substitute sequence and the RNaseP/Z cleavage site sequence are linked in this order in the 3' to 5' direction. Meanwhile, the poly(A) substitute sequence may be identical to c) the poly(A) substitute sequence as well as the RNaseP/Z cleavage site sequence may be identical to d) the above-described RNaseP/Z cleavage site sequence. The poly(A) substitute sequence and the RNaseP/Z cleavage site sequence may not be provided and a poly(A) signal sequence may be provided as a substitute. The poly(A) signal sequence may be a sequence comprising AATAAA (SEQ ID NO: 4).

k) The sequence encoding an activator for the inducible promoter is determined depending on the inducible promoter a). For instance, when the inducible promoter is TRE promoter, reverse tetracycline trans-activator gene (rtTA) can be used as the sequence k). The rtTA is a sequence necessary for the doxycycline-inducible transcription by TRE. The optional strong expression promoter j) is positioned upstream of, namely on the 5' end side of the sequence k) so as to help transcription of the activator for the inducible promoter. j) the strong expression promoter may enable constitutive expression of a gene under control of the promoter. Examples of the strong expression promoter used include EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR, HSV-TK (herpes simplex virus thymidine kinase) promoter, FerH (ferritin H-chain) promoter, and FerL (ferritin L-chain) promoter.

Among them, preferred are EF1α promoter, CAG promoter, MoMuLV LTR, CMV promoter, and SRα promoter.

Further, the optional sequence l) to drive polycistronic expression is not limited to and may be selected from substantially the same choices as of the sequence f) to drive polycistronic expression. The sequences f) and l) may be the same or different. The drug resistance sequence m) is used to subject cells containing such a reporter gene construct to drug selection. The drug resistance gene m) may be a sequence encoding a drug resistance gene. Preferable examples include, but are not limited to, puromycin resistance gene.

When a reporter gene sequence is designed, it is possible to add a sequence between the sequences f) and g) or the sequences g) and h) such that a start codon included in the sequence f) is located in-frame of the gene sequence h).

Those skilled in the art can construct such a vector by genetic engineering technique if a desired nucleic acid sequence can be designed. For instance, an insert containing essential sequences a) to m) is cloned into a commercially available piggyBac vector system to construct such a vector.

Second Embodiment: Gene Introduction Agent
(First and Second Vectors)

The second embodiment of the present invention involves a gene introduction agent comprising an episomal vector, which is a non-viral plasmid vector. Specifically, provided is a gene introduction agent comprising:

(I) a first vector comprising, in this order in the 5' to 3' direction, a) an inducible promoter; b) a sequence encoding a first marker protein; c) a poly(A) substitute sequence; d) an RNaseP/Z cleavage site sequence; e) an mRNA-stabilizing sequence; f) a sequence to drive polycistronic expression; g) an miRNA target sequence; h) a sequence encoding a second marker protein; l) EBNA1 gene, and m) a replication origin OriP; and (II) a second vector comprising, in this order in the 5' to 3' direction, (n) a strong expression promoter and (o) a sequence encoding an activator for the inducible promoter.

When the first and second vectors according to this embodiment are co-transfected into cells, a single mRNA including a first marker protein-encoding sequence, a miRNA target sequence, and a second marker protein-encoding sequence is transcribed, under control of a single inducible promoter. The first vector is an episomal vector having EBNA1 gene and a replication origin OriP, so that the vector can self-replicate and be maintained while a gene introduced into a cell is not integrated into its genome. The second vector encodes an activator for the inducible promoter of the first vector. Note that a modification embodiment of the present invention can provide a gene introduction agent consisting of a single episomal vector as constructed by cloning an activator for the inducible promoter into the first vector.

In the first vector, a) the inducible promoter, b) the sequence encoding a first marker protein, c) the poly(A) substitute sequence, d) the RNaseP/Z cleavage site sequence, e) the mRNA-stabilizing sequence, f) the sequence to drive polycistronic expression, g) the miRNA target sequence, and h) the sequence encoding a second marker protein can be selected from the elements explained and called the same names in the first embodiment.

l) The EBNA1 gene and m) the replication origin OriP are essential vector elements for the replication of an episomal vector.

Preferably, the first vector further comprises, in this order in the 5' to 3' direction, j) WPRE and k) a strong expression promoter, linked downstream of h) the sequence encoding a second marker protein and upstream of l) the EBNA1 gene. j) WPRE is Woodchuck hepatitis virus Post-transcriptional Regulatory Element for the stabilization and translation of messenger RNA. The strong expression promoter k) enables constitutive expression of a gene under control thereof and can be selected from the strong expression promoters described in the first embodiment.

The first vector may further comprise, in this order in the 5' to 3' direction, t) ColE1Ori and u) a drug resistance sequence, linked downstream of m) the replication origin OriP. Examples of the drug resistance gene include, but are not limited to, ampicillin resistance gene from the viewpoint of selection during vector amplification. As used herein, the gene sequence encoded by the first vector according to the second embodiment is also referred to as a reporter gene sequence or an miRNA-responsive reporter gene sequence.

When a reporter gene sequence in the first vector is designed, it is possible to add a sequence between the sequences f) and g) or the sequences g) and h) such that a start codon included in the sequence f) is located in-frame of the gene sequence h).

The second vector may be a plasmid vector comprising at least n) a strong expression promoter and o) a sequence encoding an activator for the inducible promoter. Like the case of the first vector, the strong expression promoter n) can be selected from the constitutively active strong expression promoters as described in the first embodiment. In addition, the sequence o) can be suitably selected depending on the inducible promoter. It is preferable that when the inducible promoter is TRE promoter, the sequence encoding an activator is rtTA.

The second vector further optionally comprising, in this order in the 5' to 3' direction, p) a sequence to drive polycistronic expression, q) a drug resistance sequence, r) WPRE, and s) a replication origin OriP, linked on the 3' end side of o) the sequence encoding an activator for the inducible promoter. p) the sequence to drive polycistronic expression, r) WPRE, and s) the replication origin OriP have the same configurations as of the above-described corresponding terms. The q) drug resistance sequence may encode a drug resistance gene. Preferable examples include, but are not limited to, puromycin resistance gene. The second vector may further comprise, in this order in the 5' to 3' direction, v) ColE1Ori and w) a drug resistance sequence, linked on the 3' end side of s) the replication origin OriP. Examples of the drug resistance sequence include, but are not limited to, ampicillin resistance gene from the viewpoint of selection during vector amplification.

In this embodiment, the second vector may be a plasmid vector comprising a replication origin OriP and may not be a complete episomal vector comprising both EBNA1 gene and OriP. This is because when the second vector is co-transfected with the first vector, the EBNA1 expressed by the first vector recognizes the OriP of the second vector, allowing for replication of the both vectors. The first vector can be an episomal vector. In this case, it is preferable that EBNA1 gene and a replication origin OriP be cloned at a position outside a region between n) and r).

Those skilled in the art can construct the first and second vectors according to the second embodiment by genetic engineering technique if desired nucleic acid sequences can be designed. For instance, an insert containing essential sequences selected from the above is cloned into a commercially available plasmid vector system to construct each vector.

Third Embodiment: Cell Stably Expressing miRNA-Responsive mRNA

The third embodiment of the present invention involves a cell that contains a vector(s) according to the first or second embodiment and stably expresses a miRNA-responsive mRNA.

The cell according to this embodiment may be collected from any kind of multicellular organisms and may be obtained by culturing an isolated cell(s). Specific examples of the cell include somatic cells collected from mammals (e.g., a human, a mouse, a monkey, a pig, a rat) and cells obtained by culturing cells isolated from each mammal or each mammalian cell line. Examples of the somatic cells include: keratinous epithelial cells (e.g., keratinocytes); mucosal epithelial cells (e.g., tongue epithelial cells); exocrine epithelial cells (e.g., mammary glandular cells); hormone-secreting cells (e.g., adrenomedullary cells); metabolic and storage cells (e.g., hepatocytes); interface-forming luminal epithelial cells (e.g., type I alveolar cells); vascular luminal epithelial cells (e.g., vascular endothelial cells); ciliated cells with transport function (e.g., tracheal epithelial cells); extracellular matrix secretory cells (e.g., fibroblasts); contractile cells (e.g., smooth muscle cells); hematopoietic and immune cells (e.g., T cells); sensory cells (e.g., rod cells); automatic nervous system neurons (e.g., cholinergic neurons); sensory and peripheral neuron-supporting cells (e.g., satellite cells); CNS neurons and glial cells (e.g., astrocytes); pigment cells (e.g., retinal pigment epithelial cells); and progenitors (tissue precursors) thereof. The cell differentiation degree and/or how old an animal, a source of the cell, is are not particularly limited. An undifferentiated progenitor (including a somatic stem cell) or a fully differentiated mature cell may be likewise used as a source of a somatic cell of the present invention. As used herein, examples of the undifferentiated progenitor include tissue stem cells (somatic stem cells) such as neural stem cells, hematopoietic stem cells, mesenchymal stem cells, and dental pulp stem cells. Preferable examples of an individual mammal which is a source of the somatic cell according to the present invention include, but are not particularly limited to, humans. In addition, more preferred are cells artificially processed after the somatic cells have been sampled. Examples include induced pluripotent stem cells (iPS cells) prepared from the somatic cells and cells obtained after pluripotent stem cells (e.g., ES cells and iPS cells) have been differentiated.

Examples of a method for introducing, into a cell, a vector(s) according to the first or second embodiment include lipofection, electroporation, a calcium phosphate co-precipitation method, a DEAE dextran method, microinjection, and a gene gun method. Specific examples include the method described in Science, 324: 797-801 (2009).

When a piggyBac-based vector according to the first embodiment is introduced into a cell, a transposase that specifically recognizes the 5'- and 3'-end nucleic acid sequences for integration in the vector, preferably a non-viral vector encoding the transposase may be introduced as a form of a plasmid vector. Plasmid vectors encoding a transposase are commercially available. Alternatively, based on the coding sequence of a transposase of interest, the plasmid vectors can be suitably constructed by those skilled in the art. The vector according to the first embodiment and the vector encoding a transposase may be co-transfected or transfected separately. In addition, the amount of the vector(s) to be transfected can be suitably determined, depending on the properties of a subject cell and purposes, by those skilled in the art and has no particular limitation.

In cells containing a piggyBac transposon-based vector and a plasmid vector encoding a corresponding transposon according to the first embodiment, a reporter gene sequence positioned between the 5'- and 3'-end nucleic acid sequences for integration is integrated into a chromosome. Then, under conditions in which the activator for the inducible promoter is active, a single mRNA is transcribed, including a sequence encoding a first marker protein, a miRNA target sequence, and a sequence encoding a second marker protein. That is, the cell can stably express the reporter genes.

When a gene introduction agent according to the second embodiment is used, a first vector and a second vector may be co-introduced or introduced separately. Then, the amount of the vectors to be introduced and how to introduce them may be determined like the case of the piggyBac transposon-based vector.

In cells containing a gene introduction agent according to the second embodiment, the nucleic acid sequences encoded by the agent are not integrated into a chromosome, but they can remain and self-replicate. Then, under conditions in which the activator for the inducible promoter is active, a single mRNA is transcribed, including a sequence encoding a first marker protein, a miRNA target sequence, and a sequence encoding a second marker protein. That is, the cell can stably express the reporter genes.

Fourth Embodiment: Method for Determining Cellular State

The fourth embodiment of the present invention involves a method for determining a cellular state. Specifically, the present invention relates to a method for visualizing a differentiation status of a cell, comprising the steps of:

(I) introducing, into the cell, a) the vector according to the first embodiment and a transposase or a vector encoding the transposase or b) the gene introduction agent according to the second embodiment; and (II) determining the differentiation status of the cell by using, as indicators, a level of translation of the first marker protein and a level of translation of the second marker protein.

The transposon-based vector a) used in step (I) according to this embodiment is as described in the first embodiment and the first- and second-vectors-containing gene introduction agent b) is as described in the second embodiment. In addition, a cell into which these vectors are to be introduced and the method for introducing these vectors into a cell are as described in the third embodiment.

Step (I) of introducing the vector(s) into a cell drives the transcription of a reporter gene sequence from the transposon-based vector a) introduced or the first- and second-vectors-containing gene introduction agent b) introduced. In either the case a) or b), the transcription is started after initiation of cell culture under conditions in which the activator for the inducible promoter is active. For instance, when the inducible promoter is TRE promoter and the activator is rtTA, the transcription by the TRE promoter can start after initiation of culturing the cell in doxycycline-containing medium.

In the case of using either the vector a) or b), an mRNA transcribed from the reporter gene sequence includes a miRNA target sequence. A miRNA specifically binds to the miRNA target sequence and may be present in RISC in a cell. In this case, the level of translation of the second marker protein, which has the upstream miRNA target sequence, is repressed. Then, the level of translation is controlled quantitatively depending on the miRNA activity. In contrast, when a cell does not contain a given miRNA or the given miRNA is not present in RISC, the levels of translation of the second marker protein are not repressed. Thus, the level of translation of the second marker protein differs between a cell having a given miRNA in RISC and a cell without the given miRNA. As used herein, the case of having a given miRNA in RISC refers to a "case of having miRNA activity". The first marker protein-encoding sequence without an upstream miRNA target sequence can be used to express the marker protein regardless of the miRNA activity. This is because the translation is not controlled depending on the level of expression of the miRNA. Without the miRNA-mediated translation repression, the ratio of the level of translation of the second marker protein to that of the first marker protein remains constant. Hence, the ratio of the level of translation of the second marker protein to that of the first marker protein may be obtained and used to estimate the level of miRNA-mediated translation repression. In a cell, miRNA activity varies depending on the type and the degree of differentiation of the cell. In addition, active miRNA species also vary. Accordingly, a cellular state can be determined depending on the level of translation repression. According to the present invention, a reporter gene sequence integrated in a chromosome or a sequence cloned in an episomal vector may be used to stably, continuously transcribe and express the corresponding mRNA.

In the determination step, a given detector may be used to detect, preferably quantify signals from the marker proteins to estimate the levels of translation of the first and second marker proteins. Examples of the detector include, but are not limited to, a flow cytometer, an imaging cytometer, a fluorescence microscope, a luminescence microscope, and a CCD camera. The person skilled in the art can suitably select and use such a detector in accordance with the kind marker protein and how to determine it. Preferable examples of how to detect the marker protein when it is a fluorescent protein include flow cytometry. Flow cytometry can be used to quantify the intensity of light emitted by a marker protein (e.g., a fluorescent protein, a luminescence enzyme) that has been translated in an individual cell and can provide the quantified levels as information for the determination.

In the case of using either the vector a) or b) according to the present invention, mRNA can be continuously transcribed from the corresponding reporter gene. Consequently, it is possible to continuously obtain signals from the marker proteins, thereby enabling continuous cellular state determination.

The determination method according to this embodiment further optionally comprises, after the cell differentiation status determination step, (III) introducing, into the cell population, the transposase or the vector encoding the transposase, thereby removing the reporter gene sequence from a genome of the cell. This step aims at removing the reporter gene sequence integrated into a chromosome when the vector according to the first embodiment is used in the introduction step (I). The determination step includes an essential determination, namely determining a state of a cell that has been differentiated into a desired type of cell, and optional sorting, followed by a step of removing the reporter gene sequence. In this step, an exogenous gene is removed from the cell, so that safety can be provided during clinical use of the cell.

EXAMPLES

Hereinafter, the present invention is described in detail by Examples. The present invention, however, is not limited to these Examples.

Experimental Materials and Methods

KOD-plus Neo (TOYOBO CO., LTD.) was used for PCRs to prepare the inserts and Ligation high ver.2 (TOYOBO CO., LTD.) was used for ligations. Oligo DNAs were purchased from Greiner Japan. Each plasmid DNA was amplified in *E. coli* (DH5α strain) and then purified using PureYield plasmid miniprep kit (Promega) or Jetstar plasmid midiprep kit (Genomed). The following details how to construct plasmid DNAs.

Only plasmid DNAs underlined are shown in Examples of the present invention. Although data on other plasmid DNAs are not shown, these plasmid DNAs were necessary when the plasmid DNAs used in this study were constructed.

pcDNA3.1-tagRFP-IRES

An IRES-containing insert was constructed by PCR using pNMD+1-2xKL4 (Endo, K., et al., Nat. Commun. 4, 2393 (2013)) as a template and a forward primer (ttctagaACGTGAGATCCGCCCCTCTCC (SEQ ID NO: 5)) and a reverse primer (AAACCGGTGGCGCGCCCATGGTTGTGGCCATATTATCATCGTG (SEQ ID NO: 6)). The resulting insert was digested by restriction enzymes AgeI and XbaI. Meanwhile, pcDNA3.1-tagRFP was also digested by restriction enzymes AgeI and XbaI and the resulting vector was then dephosphorylated with Antarctic Phosphatase (New England Biolabs Japan). The resulting digested insert and pcDNA3.1-tagRFP were ligated to give pcDNA3.1-tagRFP-IRES.

pcDNA3.1-tagRFP-IRES-hmAG1

An hmAG1 gene-containing insert was constructed by PCR using pA9-hmAG1 as a template and a forward primer (gGGCGCGCCCAGCGCTGTGAGCGTGATCAAGCCCGAGA (SEQ ID NO: 7)) and a reverse primer (ccccgggtcaCTTGGCCTGGCTGGGCAGCAT (SEQ ID NO: 8)). The resulting insert was digested by restriction enzymes AscI and XmaI. Meanwhile, pcDNA3.1-tagRFP-IRES was also digested by restriction enzymes AscI and AgeI and the resulting vector was then dephosphorylated with Antarctic Phosphatase (New England Biolabs Japan). The resulting digested insert and pcDNA3.1-tagRFP-IRES were ligated to give pcDNA3.1-tagRFP-IRES-hmAG1.

pcDNA3.1-tagRFP-TriHeliMasc-IRES-hmAG1

A MALAT1-triple helix motif- and mascRNA sequence-containing insert was constructed by PCR using the genome DNA of a SNL767 cell as a template and a forward primer (CCCCCTCGAGgattcgtcagtagggttgtaaaggtttttct (SEQ ID NO: 9)) and a reverse primer (TTCTAGAaagcaaagacaccgcagggacttga (SEQ ID NO: 10)). The resulting insert was digested by restriction enzymes XbaI and XhoI. Meanwhile, pcDNA3.1-tagRFP-IRES-hmAG1 was also digested by restriction enzymes XbaI and XhoI and the resulting vector was then dephosphorylated with rAPid alkaline phosphatase (Roche Diagnostics K.K.). The resulting digested insert and pcDNA3.1-tagRFP-IRES-hmAG1 were ligated to give pcDNA3.1-tagRFP-TriHeliMasc-IRES-hmAG1.

pDuReg-tagRFP-hmAG1

A MALAT1 triple helix motif-containing sense strand oligo DNA (TCGAGgattcgtcagtagggttgtaaaggttttcttttcctgagaaaacaacctttgttttctcaggttttgctttggccttttccctag ctttaaaaaaaaaaaagcaaaaT (SEQ ID NO: 11)) and its antisense strand oligo DNA (ttttgcttttttttttaaagctagggaaaggccaaaaagcaaaacctgagaaaacaaaaggttgttttctcaggaaaagaaaaacctttacaaccctactgacgaatc (SEQ ID NO: 12)) were phosphorylated by T4 polynucleotide kinase (Takara Bio) and were then annealed. pcDNA3.1-tagRFP-IRES-hmAG1 was digested by restriction enzymes XbaI and XhoI and the resulting vector was then dephosphorylated with rAPid alkaline phosphatase. The annealed oligo DNAs and the resulting digested pcDNA3.1-tagRFP-IRES-hmAG1 were ligated to give pDuReg-tagRFP-hmAG1.

pDuReg2-tagRFP-hmAG1 and pDuReg2M-tagRFP-hmAG1

A tagRFP gene-containing insert was constructed by PCR using pcDNA3.1-tagRFP as a template and a forward primer (GATATACGCGTTGACATTGATTATTGACT (SEQ ID NO: 13)) and a reverse primer (ccccCTCGAGtcaattaagtttgtgccccagtttgct (SEQ ID NO: 14)). The resulting insert was digested by restriction enzymes EcoRI and XhoI. Meanwhile, pDuReg-tagRFP-hmAG1 and pcDNA3.1-tagRFP-TriHeliMasc-IRES-hmAG1 were also digested by restriction enzymes EcoRI, XhoI, and NotI and the resulting vectors were then dephosphorylated with rAPid alkaline phosphatase. The resulting digested insert and each vector were ligated to give pDuReg2-tagRFP-hmAG1 and pDuReg2M-tagRFP-hmAG1.

pcDNA3.1-tagRFP-IRES-hmAG1(92a-3p), pDuReg2-tagRFP-hmAG1(92a-3p), and pDuReg2M-tagRFP-hmAG1(92a-3p)

An hsa-miR-92a-3p target sequence-containing oligo DNA (CCACAGGCCGGGACAAGTGCAATA (SEQ ID NO: 15)) and its complementary strand oligo DNA (TATTGCACTTGTCCCGGCCTGTGG (SEQ ID NO: 16)) were phosphorylated by T4 polynucleotide kinase and were then annealed. pcDNA3.1-tagRFP-IRES-hmAG1, pDuReg2-tagRFP-hmAG1, and pDuReg2M-tagRFP-hmAG1 were digested by a restriction enzyme AfeI and were then dephosphorylated by Antarctic Phosphatase. The annealed oligo DNAs and each digested vector were ligated to give pcDNA3.1-tagRFP-IRES-hmAG1(92a-3p), pDuReg2-tagRFP-hmAG1(92a-3p), and pDuReg2M-tagRFP-hmAG1(92a-3p).

pDuReg2MS-tagRFP-hmAG1(92a-3p)

A sno-lncRNA-derived end protection motif-containing sense strand oligo DNA (CTAGtggatcgatgatgacttccatatatacattccttggaaagctgaacaaaatgagtgaaaactctataccgtcattctcgtcgaac tgaggtccaT (SEQ ID NO: 17)) and its antisense strand oligo DNA (CTAGAtggacctcagttcgacgagaatgacggtatagagttttcactcatttgttcagcttccaaggaatgtatatatggaagtcat catcgatcca (SEQ ID NO: 18)) were phosphorylated by T4 polynucleotide kinase and were then annealed. pDuReg2M-tagRFP-hmAG1(92a-3p) was digested by a restriction enzyme XbaI and the resulting vector was then dephosphorylated with rAPid alkaline phosphatase. The annealed oligo DNAs and the resulting digested pDuReg2M-tagRFP-hmAG1(92a-3p) were ligated to give pDuReg2MS-tagRFP-hmAG1(92a-3p).

pCXLE-TRE-Tight

A tetracycline responsive element-containing insert was constructed by PCR using pTRE-Tight (Takara Bio) as a template and a forward primer (TTCTAGAATTGTTGTTGTTAACTTGTTTATTGCAGCTT (SEQ ID NO: 19)) and a reverse primer (CCCCAATTGCCGCGCTAGCACGCGTCA (SEQ ID NO: 20)). The resulting insert was digested by restriction enzymes MfeI and XbaI. Meanwhile, pCXLE-hSK (a gift from Dr. Keisuke Okita) was also digested by restriction enzymes EcoRI, ScaI, and XbaI and the resulting vector was then dephosphorylated with rAPid alkaline phosphatase. The resulting digested insert and pCXLE-hSK were ligated to give pCXLE-TRE-Tight.

pCXLE-TRE2M-tagRFP-hmAG1(92a-3p) and pCXLE-TRE2MS-tagRFP-hmAG1(92a-3p)

pCXLE-TRE-Tight was digested by restriction enzymes EcoRI and PvuII and the resulting vector was then dephosphorylated with rAPid alkaline phosphatase. Meanwhile, pDuReg2M-tagRFP-hmAG1(92a-3p) and pDuReg2MS-tagRFP-hmAG1(92a-3p) were digested by restriction enzymes EcoRI, PmeI, and PvuI. The digested pCXLE-TRE-Tight and pDuReg2M-tagRFP-hmAG1(92a-3p) or pDuReg2MS-tagRFP-hmAG1(92a-3p) were subjected to ligation to give pCXLE-TRE2M-tagRFP-hmAG1(92a-3p) and pCXLE-TRE2MS-tagRFP-hmAG1(92a-3p), respectively.

pCXLE-TRE2MS-tagRFP-hmAG1 pCXLE-TRE2MS-tagRFP-hmAG1(92a-3p) and pDuReg2M-tagRFP-hmAG1 were digested by restriction enzymes KpnI and NacI. An hsa-miR-92a-3p target sequence-free DNA fragment derived from pCXLE-TRE2MS-tagRFP-hmAG1(92a-3p) and a restriction enzyme AfeI recognition sequence-containing DNA fragment derived from pDuReg2M-tagRFP-hmAG1 were purified and ligated to give pCXLE-TRE2MS-tagRFP-hmAG1.

pCXLE-TRE2MS-tagRFP-hmAG1(302a-5p)

An hsa-miR-302a-5p target sequence-containing oligo DNA (CAGCAAGTACATCCACGTTTAAGT (SEQ ID NO: 21)) and its complementary strand oligo DNA (ACTTAAACGTGGATGTACTTGCTG (SEQ ID NO: 22)) were phosphorylated by T4 polynucleotide kinase and were then annealed. Then, pCXLE-TRE2MS-tagRFP-hmAG1 was digested by a restriction enzyme AfeI and was then dephosphorylated by Antarctic Phosphatase. The annealed oligo DNAs and the resulting digested pCXLE-TRE2MS-tagRFP-hmAG1 were ligated to give pCXLE-TRE2MS-tagRFP-hmAG1(302a-5p).

pENTR-D2MS-tagRFP-hmAG1(302a-5p) and pENTR-D2MS-tagRFP-hmAG1

An insert (containing a tagRFP gene, a MALAT1 triple helix motif, a mascRNA sequence, IRES, and an hsa-miR-302a-5p target sequence-free or -containing hmAG1 gene) was constructed by PCR using either pCXLE-TRE2MS-tagRFP-hmAG1(302a-5p) or pCXLE-TRE2MS-tagRFP-hmAG1 as a template and a forward primer (CAC-Catgggatccgtgtctaag (SEQ ID NO: 23)) and a reverse primer (tcaCTTGGCCTGGCTGGGCAGCAT (SEQ ID NO: 24)). Each insert was cloned into pENTR-D/TOPO (Life Technologies Japan) by TOPO cloning method to construct pENTR-D2MS-tagRFP-hmAG1(302a-5p) and pENTR-D2MS-tagRFP-hmAG1.

PB-TRE2MS-tagRFP-hmAG1(302a-5p) and PB-TRE2MS-tagRFP-hmAG1

An insert (containing a tagRFP gene, a MALAT1 triple helix motif, a mascRNA sequence, IRES, and an hsa-miR-302a-5p target sequence-free or -containing hmAG1 gene) from pENTR-D2MS-tagRFP-hmAG1(302a-5p) or pENTR-D2MS-tagRFP-hmAG1 was cloned using Gateway LR Clonase II (Life Technologies Japan) into KW542_PB_TA_ERP2 vector (a gift from Dr. Knut Woltjen) to give PB-TRE2MS-tagRFP-hmAG1(302a-5p) or PB-TRE2MS-tagRFP-hmAG1, respectively.

PB-TRE2MS-tagRFP-hmAG1(1-3p) and (208a-3p)

An hsa-miR-1-3p target sequence-containing oligo DNA (ATGGGCGCGCCCAGCCATACATACTTCTTTACATTC-CACCGCTGTGAGCGTGATC (SEQ ID NO: 25)) or an hsa-miR-208a-3p target sequence-containing oligo DNA (ATGGGCGCGCCCAGCCACAAGCTTTTT-GCTCGTCTTATCGCTGTGAGCGTGATC (SEQ ID NO: 26)) was mixed with their complementary strand oligo DNA and the mixture was heated to 98° C. and was then gradually cooled to room temperature for annealing. Meanwhile, PB-TRE2MS-tagRFP-hmAG1 was digested by a restriction enzyme AfeI. The annealed oligo DNAs were cloned, using In-Fusion HD Cloning Kit, into the digested PB-TRE2MS-tagRFP-hmAG1 to give either PB-TRE2MS-tagRFP-hmAG1 (1-3p) or (208a-3p).

pENTR-D2MS-tdTomato-hmAG1

First, pENTR-D2MS-tagRFP-hmAG1 and pNFAT-RE9x-tdTomato were each digested by restriction enzymes XhoI and EagI, and the resulting vectors were blunt-ended and phosphorylated by Mighty cloning reagent set <Blunt End> (Takara Bio). Each DNA fragment was digested by restriction enzyme BamHI, and only a DNA fragment derived from pENTR-D2MS-tagRFP-hmAG1 was dephosphorylated by Antarctic Phosphatase. These DNA fragments were ligated to give pENTR-D2MS-tdTomato-hmAG1.

pENTR-D2.5MS-tdTomato-hmAG1

An hmAG1 gene-containing insert was constructed by PCR using pENTR-D2MS-tdTomato-hmAG1 as a template and a forward primer (ACAACCATGGGCGCGCCTGT-GAGCGTGATCAAGCC (SEQ ID NO: 27)) and a reverse primer (AGCTGGGTCGGCGCGactagtTTgtcgacGCGT-CACTTGGCCTGGCTGGG (SEQ ID NO: 28)). Meanwhile, pENTR-D2MS-tdTomato-hmAG1 was digested by a restriction enzyme AscI. The PCR-constructed insert was cloned, using In-Fusion HD Cloning Kit, into the digested pENTR-D2MS-tdTomato-hmAG1 to give pENTR-D2.5MS-tdTomato-hmAG1.

pENTR-D3MS-tdTomato-hmAG1

An IRES-containing insert was constructed by PCR using pDuReg2-tagRFP-hmAG1 as a template and a forward primer (GCAGGCTCCGCGGCCGACGTGAGATCCGC-CCCTC (SEQ ID NO: 29)) and a reverse primer (GGC-GACCGGTGGATCCATGGTTGTGGCCATATTATC (SEQ ID NO: 30)). Meanwhile, pENTR-D2.5MS-tdTomato-hmAG1 was digested by restriction enzymes BamHI and EagI. The PCR-constructed insert was cloned, using In-Fusion HD Cloning Kit, into the digested pENTR-D2.5MS-tdTomato-hmAG1 to give pENTR-D3MS-tdTomato-hmAG1.

pENTR-D4MS-tdTomato-hmAG1

A MALAT1 triple helix motif- and mascRNA sequence-containing insert was constructed by PCR using pDuReg2MS-tagRFP-hmAG1(92a-3p) as a template and a forward primer (CAAGTGACGCGTCGAGATTCGTCAG-TAGGGTTGT (SEQ ID NO: 31)) and a reverse primer (CGACTAGTTTGTCGAAAGCAAAGACACCGCAGG (SEQ ID NO: 32)). Meanwhile, pENTR-D3MS-tdTomato-hmAG1 was digested by a restriction enzyme SalI. The PCR-constructed insert was cloned, using In-Fusion HD Cloning Kit, into the digested pENTR-D3MS-tdTomato-hmAG1 to give pENTR-D4MS-tdTomato-hmAG1.

pENTR-D4MS-tagRFP-hmAG1

A tagRFP gene-containing insert was constructed by PCR using pDuReg2MS-tagRFP-hmAG1(92a-3p) as a template and a forward primer (aaaGGATCCcgtgtctaagggcgaagagctg (SEQ ID NO: 33)) and a reverse primer (TTCTA-GAaagcaaagacaccgcagggacttga (SEQ ID NO: 34)). The resulting insert was digested by restriction enzymes BamHI and XhoI. Meanwhile, pENTR-D4MS-tdTomato-hmAG1 was also digested by restriction enzymes BamHI and XhoI and the resulting vector was then dephosphorylated with rAPid alkaline phosphatase. The resulting digested insert and pENTR-D4MS-tdTomato-hmAG1 were ligated to give pENTR-D4MS-tagRFP-hmAG1.

PB-TRE4MS-tagRFP-hmAG1

An insert (containing a tagRFP gene, a MALAT1 triple helix motif, a mascRNA sequence, IRES, and an hmAG1 gene) from pENTR-D4MS-tagRFP-hmAG1 was cloned, using Gateway LR Clonase II, into KW542_PB_TA_ERP2 vector (a gift from Knut Woltjen) to give PB-TRE4MS-tagRFP-hmAG1.

PB-TRE4.2MS-tagRFP-P2A-hmAG1

An insert was constructed by PCR using a P2A self-cleaving peptide gene sequence-containing oligo DNA (TGTGGGCTGGGCGCGGGTCCAGGGTTCTCCTC-CACGTCTCCAGCCTGCTTCAGCA GGCTGAAGT-TAGTAGCTCCGCTTCCgacgttgatcctggcgct (SEQ ID NO: 35)) as a template and a forward primer (ACAAC-CATGGGCGCGgtatacGGAAGCGGAGCTACTAAC (SEQ ID NO: 36)) and a reverse primer (ACGCTCACAG-GCGCGGGTCCAGGGTTCTCCTCC (SEQ ID NO: 37)). This insert was cloned, using In-Fusion HD Cloning Kit, into the AscI-digested PB-TRE4MS-tagRFP-hmAG1 to give PB-TRE4.2MS-tagRFP-P2A-hmAG1.

PB-TRE4.2MS-tagRFP-P2A-hmAG1(302a-5p)-Std1 to 4X

An hsa-miR-302a-5p target sequence-containing oligo DNA (CAGCAAGTACATCCACGTTTAAGT (SEQ ID NO: 38)) and its complementary strand oligo DNA (ACT-TAAACGTGGATGTACTTGCTG (SEQ ID NO: 39)) were phosphorylated by T4 polynucleotide kinase and were then annealed. Meanwhile, PB-TRE4.2MS-tagRFP-P2A-hmAG1 was digested by a restriction enzyme BstZ17I and the resulting vector was then dephosphorylated with rAPid alkaline phosphatase. Then, the annealed oligo DNAs and the digested PB-TRE4.2MS-tagRFP-P2A-hmAG1 were ligated. Each plasmid DNA obtained by the ligation was named in accordance with how many copies of the hsa-miR-302a-5p target sequence each plasmid DNA had.

PB-TRE4.2MS-tagRFP-P2A-hmAG1(302a-5p)-H2, D4

First, hsa-miR-302a-5p target sequence-containing oligo DNAs (H2: ACCATGGGCGCGGTACACGAGTTTATC-GAGCAAGTACATCCACGTTTAAGTGTGT ACCTCGT-GTACGGAAGCGGAGCT (SEQ ID NO: 40) and D4: ACCATGGGCGCGGTATCGAGATACCGCGCCTTCGA-GAAGCAAGTACATCCACGTT TAAGTGCTTCCGT-GATGATTACGGAAGCGGAGCT (SEQ ID NO: 41)) were each mixed with their complementary strand oligo DNA, and the mixture was heated to 98° C. and gradually cooled to room temperature for annealing. Meanwhile, PB-TRE4.2MS-tagRFP-P2A-hmAG1 was digested by a restriction enzyme BstZ17I. The annealed oligo DNAs were cloned, using In-Fusion HD Cloning Kit, into the digested PB-TRE4.2MS-tagRFP-P2A-hmAG1 to give either PB-TRE4.2MS-tagRFP-P2A-hmAG1(302a-5p)-H2 or D4.

PB-TRE2.2MS-tagRFP-P2A-hmAG1(302a-5p)-Std1 to 4X, H2, and D4

PB-TRE4.2MS-tagRFP-P2A-hmAG1(302a-5p)-Std1 to 4X, H2, D4, and PB-TRE2MS-tagRFP were digested by restriction enzymes PshAI and SbfI. Then, 9.5-kb DNA fragment derived from PB-TRE2MS-tagRFP and 2.5 to 2.6-kb DNA fragment derived from each of PB-TRE4.2MS-tagRFP-P2A-hmAG1(302a-5p)-Std1 to 4X, H2, and D4 were ligated to give PB-TRE2.2MS-tagRFP-P2A-hmAG1(302a-5p)-Std1 to 4X, H2, and D4, respectively.

pCXLE-rtTA-puro

A reverse tetracycline trans-activator gene- and puromycin resistance gene-containing insert was constructed by PCR using KW542_PB_TA_ERP2 (a gift from Knut Woltjen) as a template and a forward primer (TTTTG-GCAAAGAATTgcCACCATGTCTAGACTGGAC (SEQ ID NO: 42)) and a reverse primer (CCCGAAGCTT-GAATTTCAGGCACCGGGCTTGCG (SEQ ID NO: 43)). Meanwhile, pCXLE-hSK (a gift from Dr. Keisuke Okita) was digested by a restriction enzyme EcoRI. The insert was cloned, using In-Fusion HD Cloning Kit, into the EcoRI-digested pCXLE-hSK to give pCXLE-rtTA-puro.

pCXLEΔ-rtTA-puro

First, pCXLE-rtTA-puro was digested by a restriction enzyme EcoNI, and was then blunt-ended, phosphorylated, and ligated using Mighty cloning reagent set <Blunt End> to give pCXLEΔ-rtTA-puro.

pCXEF1pre-TRE-Tight

An EF1 promoter-containing insert was constructed by PCR using pNMD+31-BoxCD (Endo, K., et al., Nat. Commun. 4, 2393 (2013)) as a template and a forward primer (AAcctgcaggGGCTCCGGTGCCCGTCAG (SEQ ID NO: 44)) and a reverse primer (AAAcctaggccatttccaggtcctgtac-ctggccctcgtcagaCATGGTGGCGACCGGTGGAT (SEQ ID NO: 45)). The resulting insert was digested by restriction enzymes AvrII and SbfI. Meanwhile, pCXLE-TRE-Tight was digested by restriction enzymes AvrII and PstI and the resulting vector was then dephosphorylated with Antarctic Phosphatase. The resulting digested insert and pCXLE-TRE-Tight were ligated to give pCXEF1pre-TRE-Tight.

pCXEF1-TRE-Tight

A BGH poly(A) sequence-containing insert was constructed by PCR using pDisplay (Life Technologies Japan) as a template and a forward primer (ATAAATCCCCAG-TAGGATCAGCCTCGACTGTGC (SEQ ID NO: 46)) and a reverse primer (GCACGCATGATGTCTGCCATAGAGC-CCACCGCA (SEQ ID NO: 47)). Meanwhile, pCXEF1pre-TRE-Tight was digested by a restriction enzyme AccI. The insert was cloned, using In-Fusion HD Cloning Kit, into the digested pCXEF1pre-TRE-Tight to give pCXEF1-TRE-Tight.

pCXLE-neo-hSK

A kanamycin/neomycin resistance gene-containing insert was constructed by PCR using ptdTomato-N1 (Takara Bio) as a template and a forward primer (CGCAAATGGGCG-GTAGGCGTG (SEQ ID NO: 48)) and a reverse primer (aaaGGATCCaggaaccgtaaaaaggccgcgttg (SEQ ID NO: 49)). The resulting insert was digested by restriction enzymes SspI and BamHI and was then dephosphorylated with rAPid alkaline phosphatase. Meanwhile, pCXLE-hSK was digested by restriction enzymes SspI and BamHI. The resulting digested insert and pCXLE-hSK were ligated to give pCXLE-neo-hSK.

pCXLE-neo2MS-tagRFP-hmAG1(302a-5p)

An hsa-miR-302a-5p target sequence-added, hmAG1 gene- and tagRFP gene-containing insert was constructed by digesting pCXLE-TRE2MS-tagRFP-hmAG1(302a-5p) by restriction enzymes EcoRI, BglII, and NsiI. Meanwhile, pCXLE-neo-hSK was digested by restriction enzymes EcoRI and BglII and the resulting vector was then dephosphorylated with rAPid alkaline phosphatase. A DNA fragment derived from pCXLE-TRE2MS-tagRFP-hmAG1(302a-5p) and a DNA fragment derived from pCXLE-neo-hSK were ligated to give pCXLE-neo2MS-tagRFP-hmAG1(302a-5p).

pCXEF1-TRE2MS-tagRFP-hmAG1(302a-5p)

An hsa-miR-302a-5p target sequence-added, hmAG1 gene- and tagRFP gene-containing insert was constructed by PCR using pCXLE-neo2MS-tagRFP-hmAG1(302a-5p) as a template and a forward primer (ATCGCCTGGAGAATTC-GACACCATGGGATCCGTG (SEQ ID NO: 50)) and a reverse primer (GCTAGCACGCGTCAGCTGTCACTTG-GCCTGGCTGGG (SEQ ID NO: 51)). Meanwhile, pCXEF1-TRE-Tight was digested by restriction enzymes EcoRI and PvuII. The insert was cloned, using In-Fusion HD Cloning Kit, into the digested pCXEF1-TRE-Tight to give pCXEF1-TRE2MS-tagRFP-hmAG1(302a-5p).

Cell Culture

Here, 293FT cells were maintained in (4.5 g/l glucose- and L-glutamine-containing, sodium pyruvate-free, liquid) Dulbecco's Modified Eagle Medium (Nacalai Tesque) supplemented with fetal bovine serum (at a final concentration of 10%), L-glutamine (at a final concentration of 2 mM; Life Technologies Japan), MEM non-essential amino acids (at a final concentration of 0.1 mM; Life Technologies Japan), and sodium pyruvate (at a final concentration of 1 mM; Sigma-Aldrich Japan). Meanwhile, human iPS cells (hiPSCs) (201B7 strain) were maintained in StemFit AK03 (Ajinomoto) and the medium was refreshed once every 2 days. In addition, the cells were passed once every 8 days while using 0.5×TrypLE Select (Life Technologies Japan) and a cell scraper. Before cell seeding, plates were pre-coated with iMatrix-511 (Takara Bio). The culture protocol is described in detail in Nakagawa M., et al., Sci. Rep., 4 (2014), p. 3594.

Transfection and Flow Cytometry of 293FT Cells

First, 293FT cells ($1 \times 10^5$ cells) were seeded onto 24-well plates, and 1 day later the cells were transfected with the indicated amount of plasmid DNA by using 1 µl/well of Lipofectamine2000 (Life Technologies Japan). One day after that, the cells were detached from the plates by using 200 µl/well of trypsin/EDTA solution. To each well was added 500 of Dulbecco's Modified Eagle Medium, and the cells were suspended. The levels of cellular fluorescence were measured with a flow cytometer BD FACSAriaII (BD Biosciences). The excitation wavelengths were 488 nm for tagRFP and hmAG1 and 405 nm for ECFP. In addition, a band pass filter of 585/42 nm was used for tagRFP, that of 530/30 nm was used for hmAG1, and that of 450/40 nm was used for ECFP. The obtained data were analyzed by FlowJo (FLOWJO).

Measurement of miRNA by Quantitative Real-Time PCR

HiPSCs (201B7 strain) that had been cultured in conventional medium or bFGF-free medium were harvested and lysed using TaqMan microRNA cells-to-Ct kit (Life Technologies Japan). Next, miRNAs included in the cell lysate were converted, using TaqMan microRNA reverse transcription kit (Life Technologies Japan), into cDNAs. Then, TaqMan microRNA assays (Life Technologies Japan) and StepOnePlus real-time PCR system (Life Technologies Japan) were used to quantify the cDNA of each of hsa-miR-302a-5p and RNU6B. The RNU6B was used as an internal control.

Establishment of Stable Reporter hiPSCs

Prepared were transfection complexes containing 30 µl of Opti-mem (Life Technologies Japan), 133 ng of pCAG-HyAcPBase (a gift from Dr. Akitsu Hotta), 533 ng of each piggyBac donor vector, and 2.67 µl of FuGENE HD (Promega). Next, the transfection complexes were incubated at room temperature for 15 to 40 min. In addition, hiPSCs (201B7 strain) were detached from the plate and were suspended in StemFit AK03 containing 10 µM Y-27632 (Wako Pure Chemical Industries). Then, the cell concentration was measured using Countess Automated Cell Counter (Life Technologies Japan). After that, $3.3 \times 10^5$ cells were centrifuged at 800 rpm for 5 min to remove the supernatant, resuspended in 500 µl of PBS, and then re-centrifuged at 800 rpm for 5 min to remove the supernatant. The resulting cells were resuspended in the above transfection complex and were incubated at room temperature for 5 min. Subsequently, 18 µl of the cell suspension was added to 1.5 ml of StemFit AK03 containing 10 µM Y-27632 in each well of iMatrix-coated 6-well plates. Transfection of episomal vectors was conducted the same way as piggyBac vectors. From 2 or 3 days after transfection, the cells were maintained in StemFit AK03 containing 1000 ng/ml of puromycin (Invivogen).

Transfection of miRNA Inhibitor into Stable Reporter hiPSCs

To prepare transfection complexes, 1.2 µl of 10 µM mirVana miRNA inhibitor (Life Technologies Japan) and 1.0 µl of Stemfect RNA transfection reagent (Stemgent) were each diluted with 12.5 µl of Stemfect transfection buffer. The two dilutions were mixed and incubated at room temperature for 10 min. Stable reporter hiPSCs (established by introducing PB-TRE2MS-tagRFP-hmAG1(302a-5p)) were detached, using 0.5×TrypLE Select, from plates and were then suspended in 374 µl of 10 µM Y-27632-containing StemFit AK03. The cell suspension was mixed with the miRNA inhibitor transfection complex, and the resulting mixture was added to wells of a 24-well plate (coated with iMatrix). The medium was changed to medium containing 10 µM Y-27632 and 0 to 2000 ng/ml doxycycline (Takara Bio). One day after the miRNA inhibitor transfection, the cells were detached from the plate and the levels of fluorescence of each cell were measured with BD Accuri (BD Biosciences Inc.). The excitation wavelength was 488 nm for both tagRFP and hmAG1, and a band pass filter of 585/40 nm was used for tagRFP and a band pass filter of 533/30 nm was used for hmAG1. The obtained data were analyzed by FlowJo.

To Induce Differentiation of hiPSCs by Culturing in bFGF-Free Medium and Analyze the hiPSCs by Flow Cytometry Stable reporter hiPSCs for hsa-miR-302a-5p (50 to $1.0 \times 10^5$ cells per well; a smaller number of cells was seeded for longer culture days to avoid confluence) were seeded on 24-well plates. From one day after that, the cells were cultured in bFGF-free StemFit AK03. One day before flow cytometry measurement, doxycycline was added at 1000 ng/ml to the medium. The cells were harvested, using 0.5×TrypLE Select, at each measurement time point, and the levels of fluorescence of each cell were measured with BD Accuri. The excitation wavelength was 488 nm for both tagRFP and hmAG1, and a band pass filter of 585/40 nm was used for tagRFP and a band pass filter of 533/30 nm was used for hmAG1. The obtained data were analyzed by FlowJo. The readings from stable reporter cells established using each of PB-TRE2MS-tagRFP and PB-TRE-IRES-hmAG1 were used to compensate for fluorescence overlap.

Differentiation of hiPSCs by Culturing in bFGF-Free Medium and Fluorescent Microscopic Imaging Stable reporter hiPSCs for hsa-miR-302a-5p ($1.3 \times 10^4$ cells per well) were seeded on 6-well plates. From 1 day after that, the cells were cultured in bFGF-free StemFit AK03. One day before fluorescence microscopic imaging, doxycycline was added at 1000 ng/ml to the medium. Fluorescent microscopic images were captured using IN Cell Analyzer 6000 (GE Healthcare Japan). The excitation wavelengths were 561 nm for tagRFP and 488 nm for hmAG1. In addition, the exposure time was 200 ms. The hmAG1/tagRFP fluorescence ratio was analyzed by ImageJ. Note that images before brightness and contrast adjustment were used for this analysis. In addition, regions where the tagRFP intensity was lower than a threshold were regarded as having no fluorescence and excluded from the hmAG1/tagRFP fluorescence ratio analysis. The brightness and contrast of the fluorescent images on days 0, 7, 15 were identically adjusted.

Neural Differentiation of hiPSCs and Fluorescent Microscopic Imaging

Differentiation into dopaminergic neurons was induced in accordance with the protocol described in Nakagawa M., et al., Sci. Rep., 4 (2014), p. 3594. Here, the protocol is described briefly. Stable reporter hiPSCs for hsa-miR-302a-5p ($1.0\times10^6$ cells per well) were seeded on a 24-well plate coated with iMatrix. From 1 day after the seeding, the cells were cultured in Glasgow's Minimum Essential Medium (Life Technologies Japan) supplemented with knockout serum replacement (at a final concentration of 8%; Life Technologies Japan), MEM non-essential amino acids (at a final concentration of 0.1 mM), sodium pyruvate (at a final concentration of 1 mM), LDN193189 (at a final concentration of 100 nM; Stemgent), A-83-01 (at a final concentration of 500 nM; Stemgent), Purmorphamine (at a final concentration of 2 µM; Merck Millipore), and FGF-8 (at a final concentration of 100 ng/ml; Wako Pure Chemical Industries). On day 3 after the seeding, CHIR99021 was then added at 3 µM. On day 7, the medium was changed to Glasgow's Minimum Essential Medium supplemented with knockout serum replacement (at a final concentration of 8%), MEM non-essential amino acids (at a final concentration of 0.1 mM), sodium pyruvate (at a final concentration of 1 mM), LDN193189 (at a final concentration of 100 nM), and CHIR99021 (at a final concentration of 3 µM). On day 10, the cells were harvested using 0.5×TrypLE Select and cell scrapers, suspended in 10 µM Y-27632-containing medium, and re-seeded at $4.0\times10^5$ cells per well of 24-well plates (coated with iMatrix-511). Then, doxycycline was added at 1000 ng/ml to the medium. The fluorescence microscopic images were captured using substantially the same procedure as described in "To Induce Differentiation of hiPSCs by Culturing in bFGF-free Medium and Capture Fluorescent Microscopic Images".

Immunostaining with TRA-1-60 and Fluorescent Microscopic Imaging

First, the cells attached to the 24-well plates were washed 3 times with PBS. Next, the cells were cultured in medium containing Alexa Fluor 647 mouse anti-human TRA-1-60 (BD Biosciences Japan) (medium:antibody=10:1) for 2 h. Then, the cells were washed 3 times with the medium, and fluorescent microscopic images were captured using IN Cell Analyzer 6000. The excitation wavelength used was 642 nm and the exposure time was 3000 ms. The brightness and contrast of the fluorescent images in the same figure sets were identically adjusted.

Differentiation of hiPSCs by Culturing in bFGF-Free Medium and Time-Lapse Imaging Stable reporter hiPSCs for hsa-miR-302a-5p were seeded on a 24-well plate. From 1 day after the seeding, the cells were cultured in bFGF-free, doxycycline (at a final concentration of 1000 ng/ml)-containing StemFit AK03. On day 5, the cells were harvested using 0.5×TrypLE Select and cell scrapers, suspended in 10 µM Y-27632-containing medium, and re-seeded (at 4000 cells per well) on 24-well plates coated with iMatrix-511. From one day after the re-seeding, time-lapse images were captured using BioStation CT (Nikon). The exposure time was 200 ms.

Calculating and Designing Accessibility to miRNA Target Sequences

To engineer accessibility to each miRNA target sequence, custom scripts and RNAfold were used to design the target sequences and surrounding sequences thereof. Note that at this time, parameters for RNAfold were set to default values. The accessibility (kcal/mol) of each reporter messenger RNA was determined using ParasoR. At this time, the parameters of the window size were set to 3, 5, and 23.

Cardiac Differentiation of hiPSCs

Stable reporter hiPSCs (established by introducing PB-TRE2MS-tagRFP-hmAG1(1-3p) or PB-TRE2MS-tagRFP-hmAG1(208a-3p)) were seeded at $5\times10^5$ cells per well on a 6-well ultra-low attachment plate (Corning) to induce the formation of embryoid bodies over 24 h. As the medium used at this time, used was 1.5 ml per well of StemPro-34 medium (Thermo Fisher Scientific) supplemented with L-glutamine (at a final concentration of 2 mM; Thermo Fisher Scientific), ascorbic acid (at a final concentration of 50 µg/ml; Sigma-Aldrich Japan), transferrin (at a final concentration of 150 µg/ml; Roche), monothioglycerol (at a final concentration of $4\times10^{-4}$ M; Sigma-Aldrich Japan), Y-27632 (at a final concentration of 10 µM), and human recombinant BMP4 (at a final concentration of 2 ng/ml; R&D Systems). Also, prepared was StemPro-34 medium supplemented with L-glutamine (at a final concentration of 2 mM), ascorbic acid (at a final concentration of 50 µg/ml), transferrin (at a final concentration of 150 µg/ml), monothioglycerol (at a final concentration of $4\times10^{-4}$ M), human recombinant bFGF (at a final concentration of 10 ng/ml; R&D systems), human recombinant Activin A (at a final concentration of 12 ng/ml; R&D systems), and human recombinant BMP4 (at a final concentration of 18 ng/ml). One day after cell passage, 1.5 ml of this medium was added thereto. On day 3, the embryoid bodies were washed with Iscove's Modified Dulbecco's Medium (Thermo Fisher Scientific), and was then cultured for 4 days in 3 ml of StemPro-34 medium supplemented with L-glutamine (at a final concentration of 2 mM), ascorbic acid (at a final concentration of 50 µg/ml), transferrin (at a final concentration of 150 µg/ml), monothioglycerol (at a final concentration of $4\times10^{-4}$ M), human recombinant VEGF (at a final concentration of 10 ng/ml; R&D systems), and IWP-3 (at a final concentration of 1 µM; Stemgent). On day 7, the medium was changed to StemPro-34 medium supplemented with L-glutamine (at a final concentration of 2 mM), ascorbic acid (at a final concentration of 50 µg/ml), transferrin (at a final concentration of 150 µg/ml), monothioglycerol (at a final concentration of $4\times10^{-4}$ M), human recombinant VEGF (at a final concentration of 10 ng/ml), and human recombinant bFGF (at a final concentration of 5 ng/ml). After that, the cells were refed every two days. The embryoid bodies were cultured in a 5% $CO_2$, 5% $O_2$ hypoxia environment for the first 12 days, and then transferred to a 5% $CO_2$ normoxia environment for the reminder of the culture period.

Transfection of miRNA Inhibitor into hiPSC-Derived Cardiomyocytes

After cardiac differentiation, the day-20 embryoid bodies were dissociated by treatment with type I collagenase (Sigma) for 1 h, followed by 5-min treatment with 0.25% trypsin/EDTA. After the dissociation, the resulting cells were centrifuged and resuspended in the medium, and seeded on fibronectin (Sigma)-coated 24-well plates. To prepare the transfection complexes, 1.2 µl of 10 µM mirVana miRNA inhibitor and 1.0 µl of Stemfect RNA transfect reagent were each diluted in 12.5 µl of Stemfect RNA transfection buffer. The two dilutions were mixed and incubated at room temperature for 15 min. These transfection complexes were added to the seeded cells. Four hours after the transfection, the medium was changed to medium containing doxycycline (at a final concentration of 500 ng/ml). One day after the miRNA inhibitor transfection, the cells were harvested, using 250 μl/well of 0.25% trypsin/EDTA, and the levels of fluorescence of each cell were measured with BD Accuri. The excitation wavelength was 488 nm for both tagRFP and hmAG1, and a band pass filter of 585/40 nm was used for tagRFP and a band pass filter of 533/30 nm was used for hmAG1. The obtained data were analyzed by FlowJo. The readings obtained by using stable reporter cells established using each of PB-TRE2MS-tagRFP and PB-TRE-IRES-hmAG1 were used to compensate for fluorescence overlap.

Sorting and cTNT Staining of Cardiomyocytes

After cardiac differentiation, the cells were likewise seeded on 6-well plates as described in "Transfection of miRNA Inhibitor into hiPSC-derived Cardiomyocytes". Next, doxycycline was added at a final concentration of 500 ng/ml to the medium. One day after the doxycycline addition, the cells were harvested using 1 ml/well of 0.25% trypsin/EDTA and separated and purified, on the basis of fluorescence readings, by using BD FACSAriaII. The excitation wavelengths were 561 nm for tagRFP and 488 nm for hmAG1. In addition, a band pass filter of 585/42 nm was used for tagRFP and that of 530/30 nm was used for hmAG1. The separated and purified cells were washed with PBS, fixed with 4% paraformaldehyde, permeabilized with saponin (Sigma-Aldrich), and then stained with an anti-cardiac troponin T antibody (Thermo Fisher Scientific). After that, APC goat anti-mouse Ig (BD Biosciences) was used as a secondary antibody.

cTNT Staining and Fluorescent Microscopic Imaging

Stable reporter hiPSCs (established by introducing PB-TRE2MS-tagRFP-hmAG1(1-3p) or PB-TRE2MS-tagRFP-hmAG1(208a-3p)) were seeded at $2\times10^4$ cells per well on a 96-well ultra-low attachment plate (Corning) to induce the formation of embryoid bodies over 24 h. As the medium, used was 70 μl per well of StemPro-34 medium supplemented with L-glutamine (at a final concentration of 2 mM), ascorbic acid (at a final concentration of 50 μg/ml), transferrin (at a final concentration of 150 μg/ml), monothioglycerol (at a final concentration of $4\times10^{-4}$ M), Y-27632 (at a final concentration of 10 μM), and human recombinant BMP4 (at a final concentration of 2 ng/ml). Also, prepared was StemPro-34 medium supplemented with L-glutamine (at a final concentration of 2 mM), ascorbic acid (at a final concentration of 50 μg/ml), transferrin (at a final concentration of 150 μg/ml), monothioglycerol (at a final concentration of $4\times10^{-4}$ M), human recombinant bFGF (at a final concentration of 10 ng/ml), human recombinant Activin A (at a final concentration of 12 ng/ml), human recombinant BMP4 (at a final concentration of 18 ng/ml), and doxycycline (at a final concentration of 1000 ng/ml). One day after cell passage, 70 μl of this medium was added thereto. On day 3, the embryoid bodies were transferred to a 24-well ultra-low attachment plate (Corning) and washed with Iscove's Modified Dulbecco's Medium, and then cultured for 3 days in 500 μl of StemPro-34 medium supplemented with L-glutamine (at a final concentration of 2 mM), ascorbic acid (at a final concentration of 50 μg/ml), transferrin (at a final concentration of 150 μg/ml), monothioglycerol (at a final concentration of $4\times10^{-4}$ M), human recombinant VEGF (at a final concentration of 10 ng/ml), IWP-3 (at a final concentration of 1 μM), SB431542 (at a final concentration of 5.4 μM; Sigma-Aldrich Japan), Dorsomorphin (at a final concentration of 0.6 μM; Sigma-Aldrich Japan), and doxycycline (at a final concentration of 500 ng/ml). On day 6, the embryoid bodies were dissociated by treatment with Accumax (Innovative Cell Technologies) for 20 min, and seeded on a fibronectin-coated 24-well cell culture plate (Corning) at 1 to $2\times10^4$ cells/well in 500 μl of the same medium from day 3. On day 7, the medium was changed to 500 μl of StemPro-34 medium supplemented with L-glutamine (at a final concentration of 2 mM), ascorbic acid (at a final concentration of 50 μg/ml), transferrin (at a final concentration of 150 μg/ml), monothioglycerol (at a final concentration of $4\times10^{-4}$ M), human recombinant VEGF (at a final concentration of 10 ng/ml), and doxycycline (at a final concentration of 500 ng/ml). The embryoid bodies and the seeded cells were cultured in a 5% $CO_2$, 5% $O_2$ hypoxia environment for the first 7 days and then transferred to a 5% $CO_2$ normoxia environment. On day 14, the cells were washed with PBS, fixed with 4% paraformaldehyde, permeabilized with saponin, and then stained with an anti-cardiac troponin T antibody. A goat anti-mouse IgG (H+L) cross-adsorbed secondary antibody, Alexa Fluor 647 (Thermo Fisher Scientific) was used as a secondary antibody. Cell nuclei were stained with Hoechst 33342 (Thermo Fisher Scientific). Fluorescent microscopic images were captured using BZ X710 (Keyence). The excitation wavelengths were 560 nm for tagRFP, 470 nm for hmAG1, 620 nm for Alexa Fluor 647, and 360 nm for Hoechst 33342. In addition, the exposure times were 2000 ms for tagRFP, 6000 ms for hmAG1, 2000 ms for Alexa Fluor 647, and 435 ms for Hoechst 33342.

Results

Design of Single Promoter-Driven Dual Reporter Vectors to Monitor miRNA Dynamics There have been several studies about the long-term monitoring of miRNA activity by lenti- or retro-viral vectors containing miRNA target sequences. In those studies, the vectors were designed to either transcribe only a miRNA-responsive reporter (i.e., no reference reporter was transcribed) or to transcribe reference and miRNA-responsive reporters individually from different promoters. However, in these vector designs, transcriptional repression by epigenetic modifications may alter the expression ratio of the two reporter genes, because the susceptibility to the epigenetic modifications differs depending on promoters or genes.

In order to avoid that such transcriptional repression is misinterpreted as miRNA-mediated post-transcriptional repression, the present inventors designed a vector such that a reference reporter gene and an miRNA-responsive reporter gene are transcribed, in a single messenger RNA, from the same promoter. By doing so, these two genes are subject to identical transcriptional control (FIG. 1). The reference reporter (tagRFP) gene is located at the 5' end side of the messenger RNA, and the miRNA-responsive reporter (human codon-optimized monomeric Azami Green; hmAG1) gene is located at the 3' end side of the same messenger RNA. In addition, an internal ribosome entry site (IRES) was inserted upstream of hmAG1 to induce the translation of hmAG1. A target sequence that is complementary to the corresponding miRNA was inserted between the IRES and the hmAG1. If the miRNA is active in the cell, the expression of hmAG1 is repressed through base pairing between the miRNA and its target sequence. Because this miRNA-target sequence is perfectly complementary to the corresponding miRNA, the RNA-induced silencing complex (RISC) will likely cleave the messenger RNA at this miRNA target site. However, this cleavage also causes the tagRFP to be separated from the poly(A) sequence. Given that the poly (A) sequence is important for the stabilization and translation of messenger RNAs, its loss could cause the miRNA to repress not only hmAG1 but also tagRFP expression, which would compromise the detection of miRNA activity when the hmAG1/tagRFP ratio is measured. Thus, to avoid the repression of tagRFP expression, the present inventors inserted a triple helix (TH) sequence derived from a long non-coding (lnc)RNA, MALAT-1, to stabilize the messenger RNA and assist the translation of tagRFP even without the poly(A) (FIG. 1A).

It has been known that an miRNA named hsa-miR-92a-3p(miR-92a) has increased activity in 293FT cells. Thus, the present inventors first constructed a reporter vector containing a target sequence of this miR-92a and transfected this reporter vector into 293FT cells. In addition, a reference ECFP reporter vector (pcDNA3.1-ECFP) was co-transfected as a transfection control. In addition, to investigate the specificity of the present miRNA-responsive reporter vectors, either a miR-92a-specific miRNA inhibitor or negative control reagent, which does not inhibit miR-92a, was co-transfected.

Simple insertion of the IRES and TH motif into the vector failed to allow 293FT cells to be distinguished on the basis of miR-92a activity (FIGS. 1B to 1E, the upper panels). Next, RNaseP/RNaseZ cleavage sequences were inserted between the triple helix motif and the IRES so as to prevent the miRNA-mediated repression of tagRFP. In contrast to the first vector without the RNaseP/Z cleavage sequences, tagRFP expression from the second vector was hardly repressed by miR-92a, whereas hmAG1 expression was (FIGS. 1B to 1E, the middle panels).

Figure 1C:
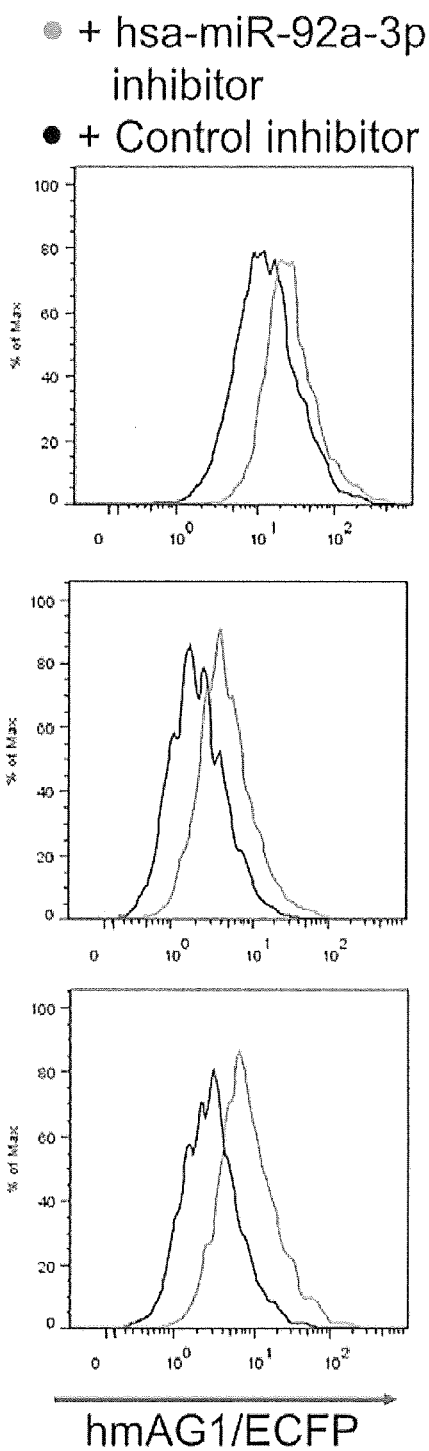
FIG. 1C is fluorescence histograms of the respective fluorescent proteins in tagRFP-positive and hmAG1-positive cells.
Figure 1D:
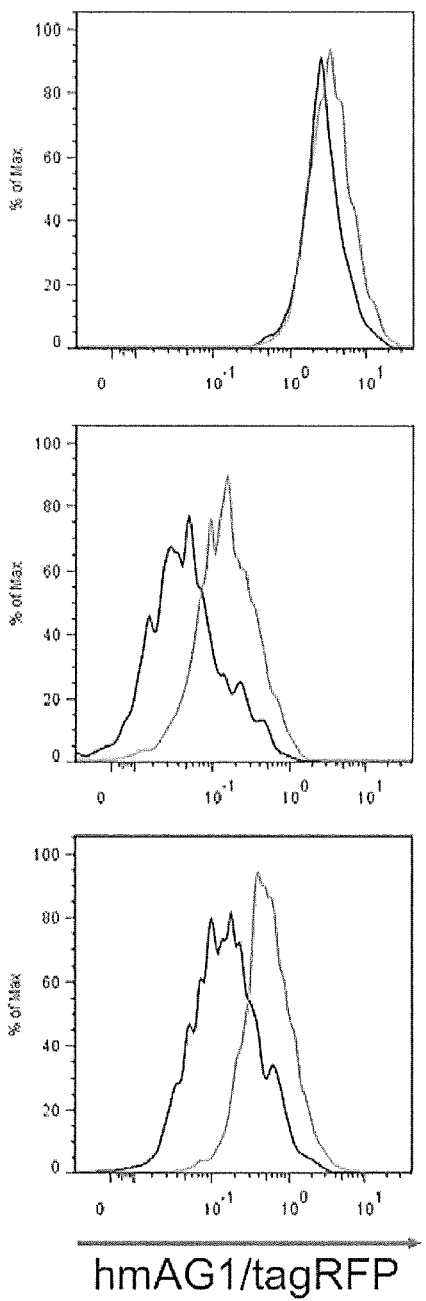
FIG. 1D is fluorescence histograms of the respective fluorescent proteins in tagRFP-positive and hmAG1-positive cells.
Figure 1E:
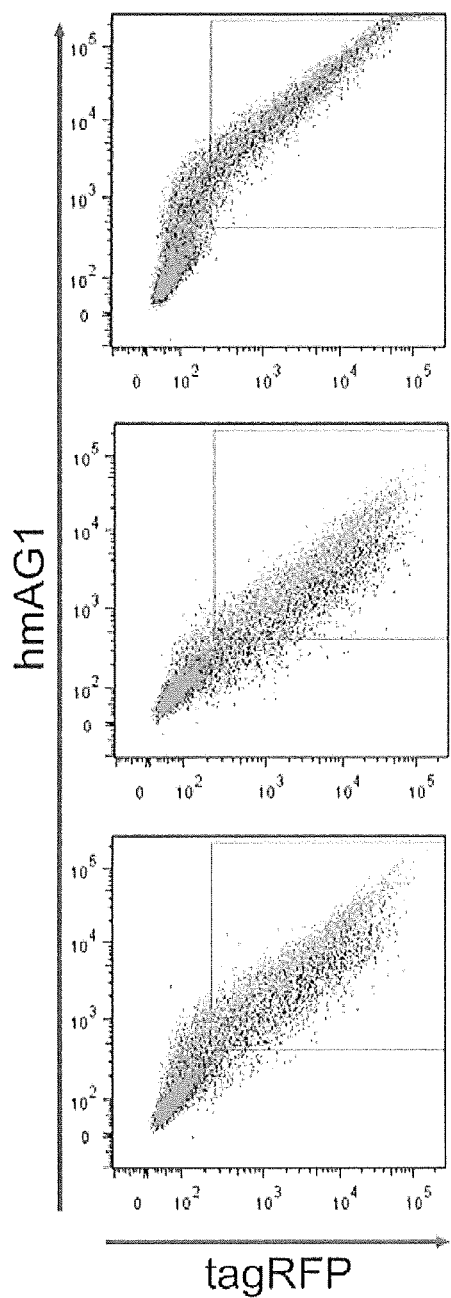
FIG. 1E is two-dimensional (2D) dot plots showing the levels of fluorescence of tagRFP and hmAG1. The green dots represent the hsa-miR-92a-3p inhibitor-containing cells. The black dots represent the negative control-containing cells.

Use of this second vector made it possible to distinguish cells on the basis the miR-92a activity. However, the level of expression of hmAG1 was lower than that of the first vector even in the miR-92a-inhibitor-treated cells (FIGS. 1C to 1E, the upper and middle panels). The present inventors believed that this lower expression was due to the destabilization of hmAG1 messenger RNA after the RNaseP/Z-mediated cleavage, because the cleaved hmAG1 messenger RNA lacked protection by the 5' cap structure. Then, to increase the stability of the cleaved hmAG1 messenger RNA and to restore the hmAG1 expression level, an end-protection motif (derived from sno-lncRNA) was inserted between the RNaseP/Z cleavage sequence and the IRES (FIG. 1A, the bottom). The addition of this motif partially restored hmAG1 expression (FIGS. 1C to 1E, lower panels and FIG. 8). Here, this vector made it possible to discriminate cells with miR-92a activity from cells without it (FIG. 1E, the lower panel). Thus, the present inventors used the third reporter vector design in the following study.

Figure 9:
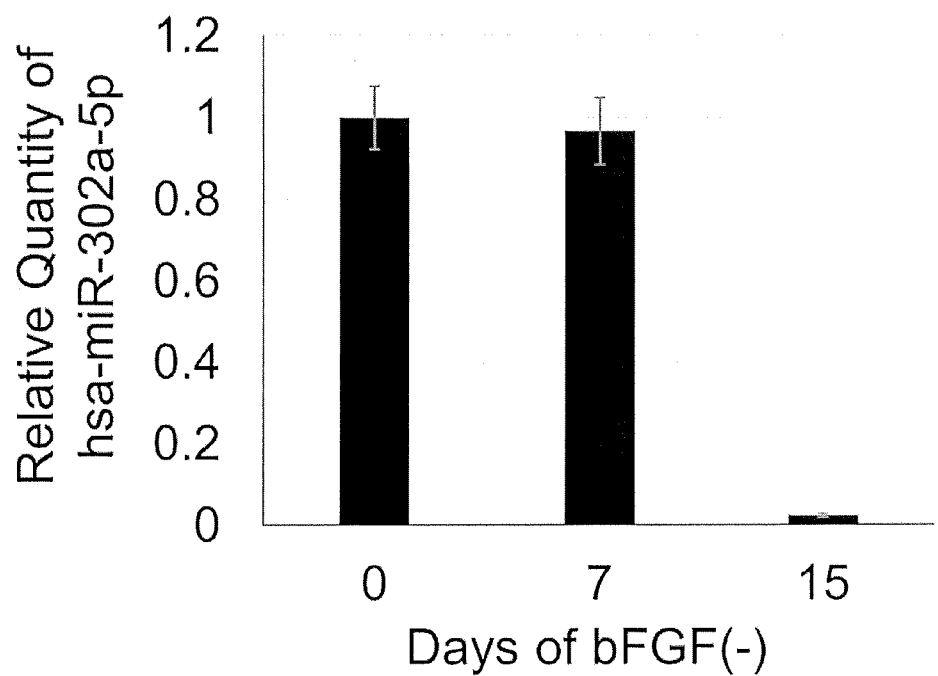
FIG. 9 shows the levels of expression of hsa-miR-302a-5p in hiPSCs before and after differentiation. Here, hiPSCs (201B7 strain) were cultured in conventional medium (day 0), and were then cultured in bFGF-free medium for 7 or 15 days. The level of expression of hsa-miR-302a-5p at each time point was determined by RT-PCR. The level of expression of RNU6B was used as an internal control. The error bars indicate standard deviations (n=3).

Establishment of Stable miRNA-Responsive Reporter hiPSCs by Genomic Integration of Reporter Genes To continuously monitor miRNA dynamics during differentiation, stable miRNA-responsive reporter hiPSCs were established. To efficiently establish the stable reporter cells, a piggyBac transposon system was utilized. The first reporter piggyBac vector was designed so as to detect a miRNA named hsa-miR-302a-5p (hsa-miR-302a-5p), which is highly expressed in human pluripotent stem cells (FIG. 9). Then, this hsa-miR-302a-5p-responsive reporter piggyBac vector and the hyperactive piggyBac transposase expression vector pCAG-HyAcPBase were co-transfected into hiPSCs (201B7 strain).

Figure 2A:
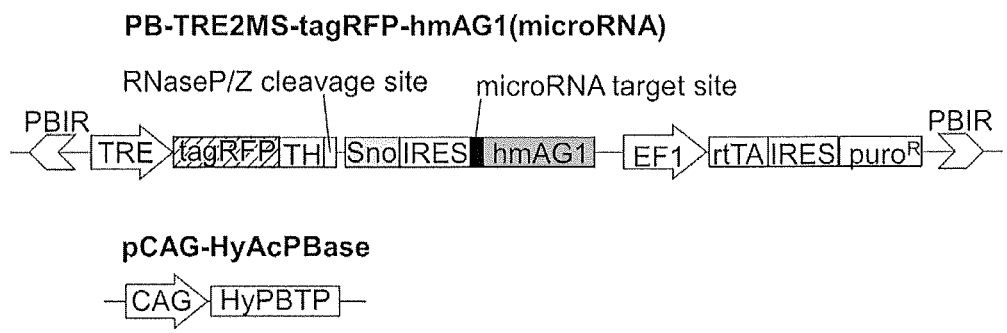
FIG. 2A illustrates the structure of a piggyBac-based plasmid vector. Each abbreviation means as follows: PBIR, inverted repeat sequences of the piggyBac transposon for transposase-mediated integration of the reporter genes; TRE, tetracycline response element; tagRFP, tagRFP gene; TH, MALAT-1 long non-coding RNA-derived triple helix motif; Sno, small nuclear RNA-like long non-coding RNA-derived end protection motif; IRES, internal ribosome entry site for the translation of hmAG1; hmAG1, humanized monomeric Azami Green gene; EF1, elongation factor 1 alpha promoter; rtTA, reverse tetracycline trans-activator gene; puroR, puromycin resistance gene; CAG, CAG promoter composed of cytomegalovirus early enhancer and beta-actin promoter; and HyAcPBTP, hyperactive piggyBac transposase gene for the integration of genes inserted between two PBIRs.
Figure 2B:
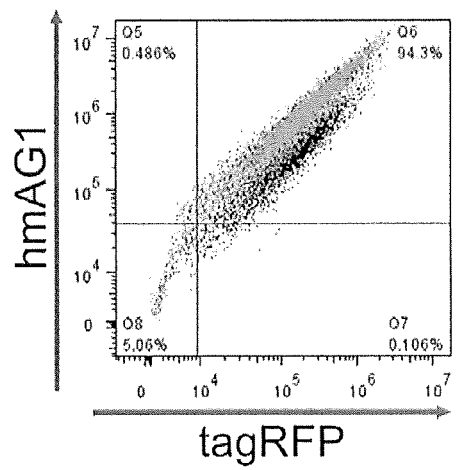
FIG. 2B is a 2D dot plot showing the levels of fluorescence of tagRFP and hmAG1.

The obtained stable reporter hiPSCs were transfected with either an hsa-miR-302a-5p-specific inhibitor or a negative control reagent, which does not inhibit hsa-miR-302a-5p, and the levels of fluorescence of tagRFP and hmAG1 were analyzed by flow cytometry. As expected, the inhibition of hsa-miR-302a-5p increased the hmAG1/tagRFP ratio and shifted the cell population upwards in a two-dimensional dot plot (FIG. 2B). This result indicated that hmAG1 expression was repressed by hsa-miR-302a-5p in the stable reporter cells and that these hiPSCs can be used to detect hsa-miR-302a-5p activity.

Figure 2C:
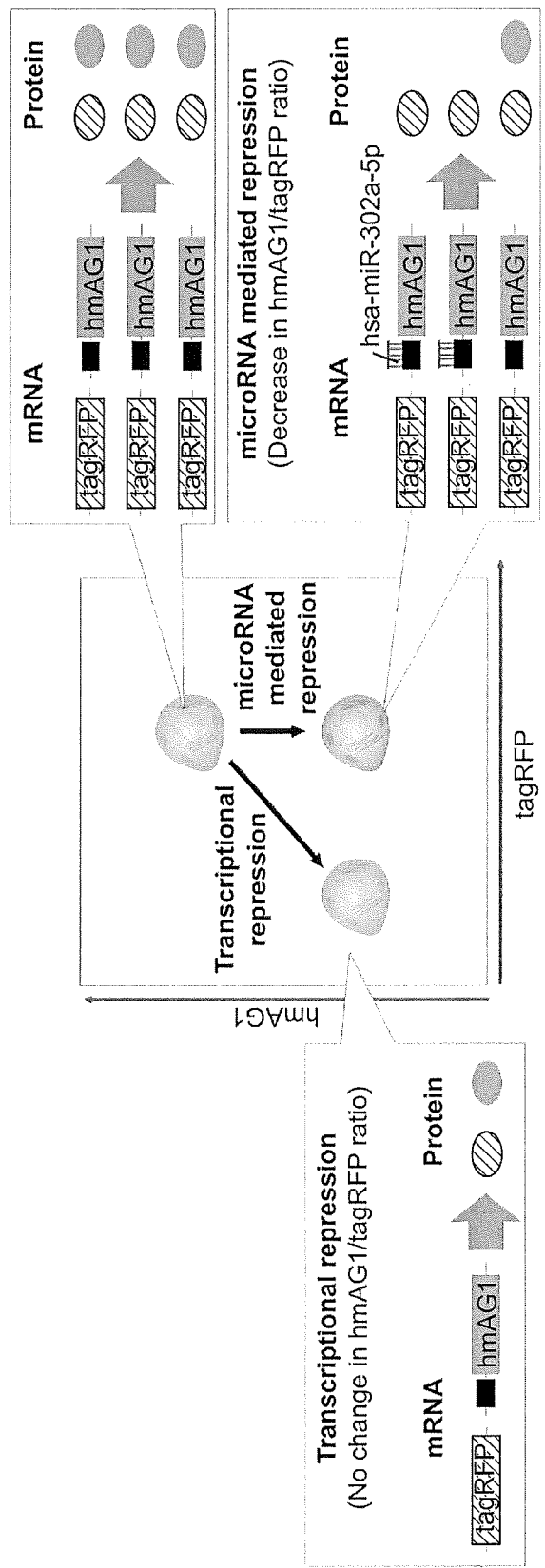
FIG. 2C is a schematic diagram illustrating how to distinguish between miRNA activity-mediated repression and transcriptional repression.
Figure 2D:
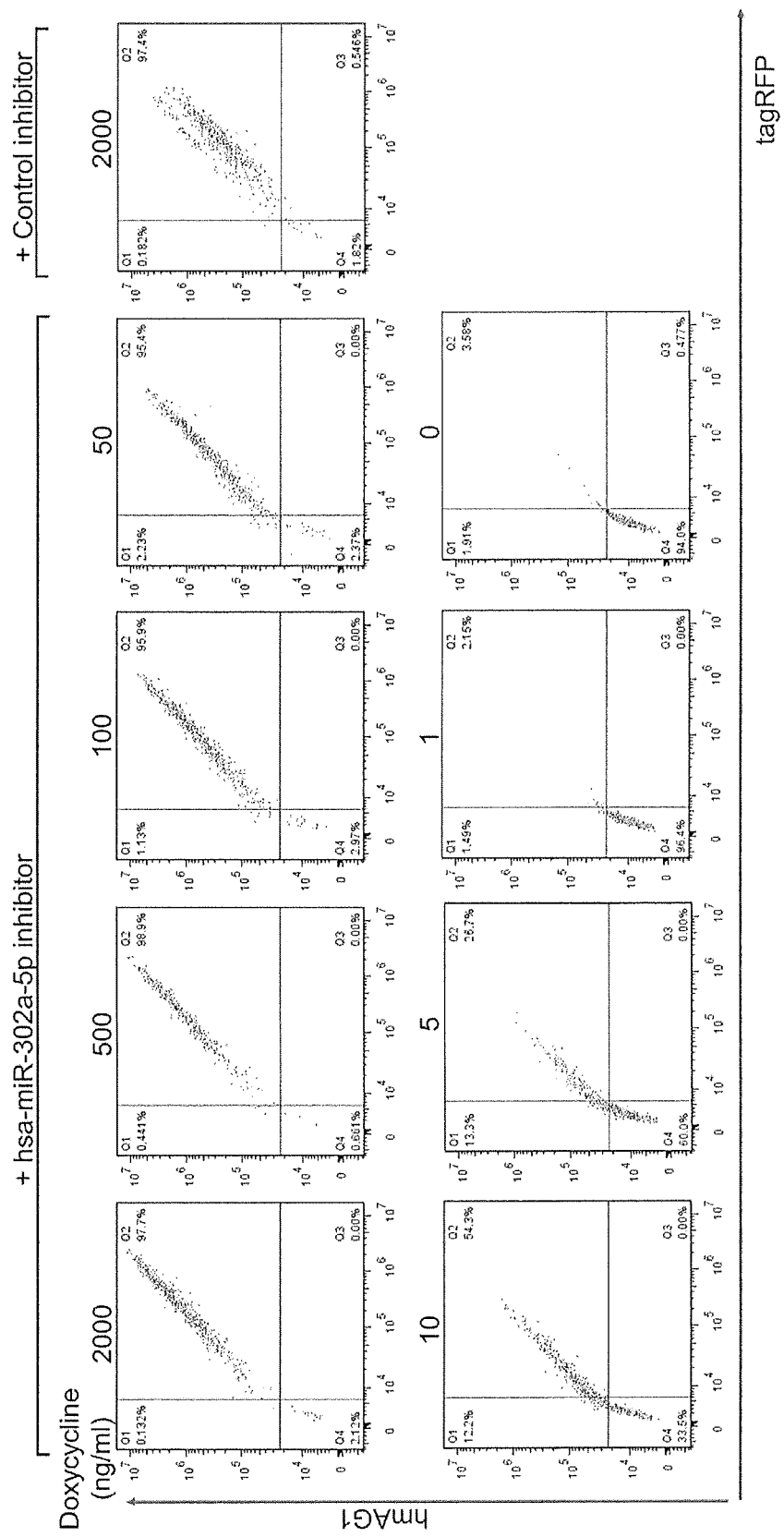
FIG. 2D is 2D dot plots showing the levels of fluorescence of tagRFP and hmAG1 when doxycycline was used to induce transcription in the presence or absence of hsa-miR-302a-5p.
Figure 2E:
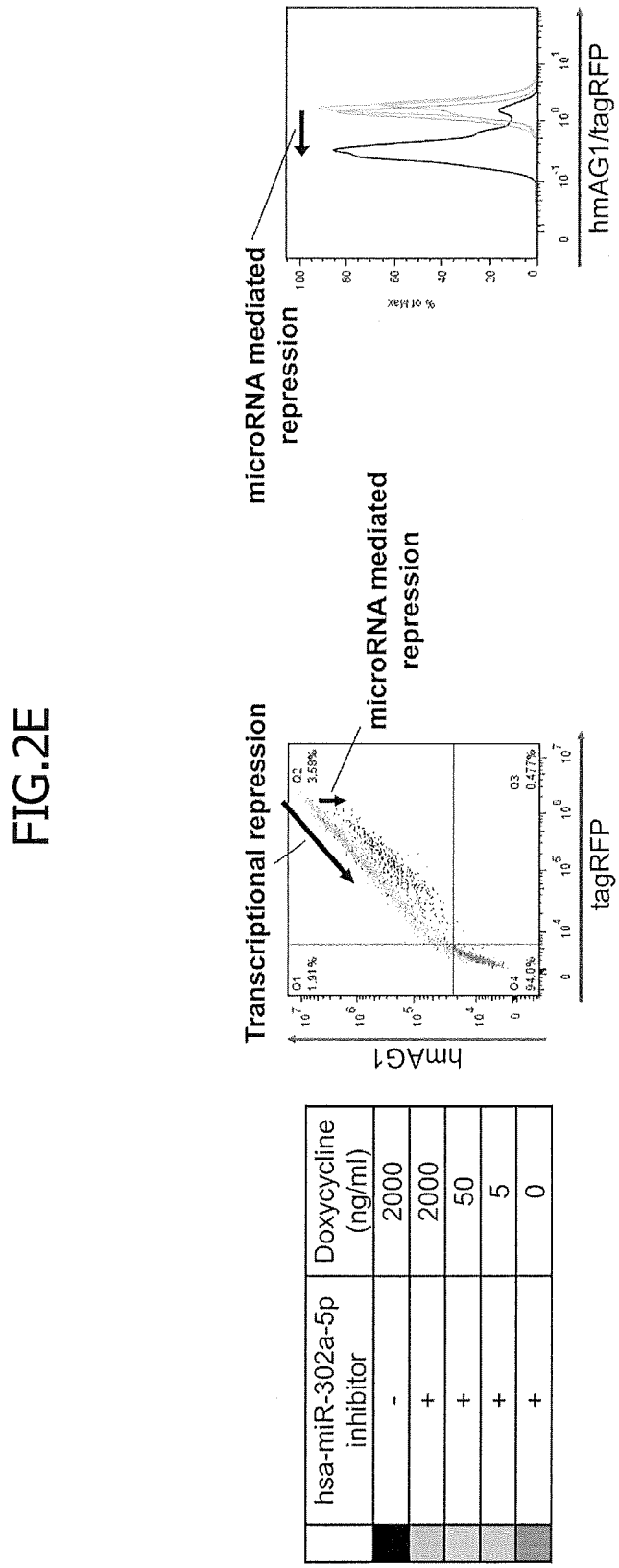
FIG. 2E contains a 2D dot plot (left) of the cells shown in FIG. 2D and superimposed histograms (right) showing the hmAG1/tagRFP ratio.

Distinction Between Transcriptional Repression and miRNA-Mediated Post-Transcriptional Repression Reporter genes are prone to be subject to transcriptional repression during long-term culture, especially when cells differentiate. Accordingly, to monitor the miRNA dynamics during differentiation, it is important to distinguish between transcriptional repression and miRNA-mediated post-transcriptional repression. In the present vector designs, transcriptional repression should similarly affect both the reference (tagRFP) and the miRNA-responsive (hmAG1) reporter genes whereas miRNA-mediated repression would only affect hmAG1 expression. To investigate this possibility, the transcription levels of the reporter genes were varied by treating the stable reporter cells with various concentrations of doxycycline (at 0 to 2000 ng/ml). As expected, in cells where hsa-miR-302a-5p activity was inhibited, the transcriptional repression due to a decrease in doxycycline concentration likewise caused a decrease in the level of expression of hmAG1 and tagRFP, resulting in no change in the hmAG1/tagRFP ratio (FIGS. 2D and 2E). In contrast, in cells where hsa-miR-302a-5p activity was not inhibited, endogenous hsa-miR-302a-5p selectively reduced expression of hmAG1, resulting in a change in the hmAG1/tagRFP ratio (FIGS. 2D and 2E). These results have demonstrated that the cells with hsa-miR-302a-5p can be distinguished from the cells with silenced reporter gene transcription.

Monitoring and Visualizing miRNA Dynamics During hiPSC Differentiation

Figure 3A:
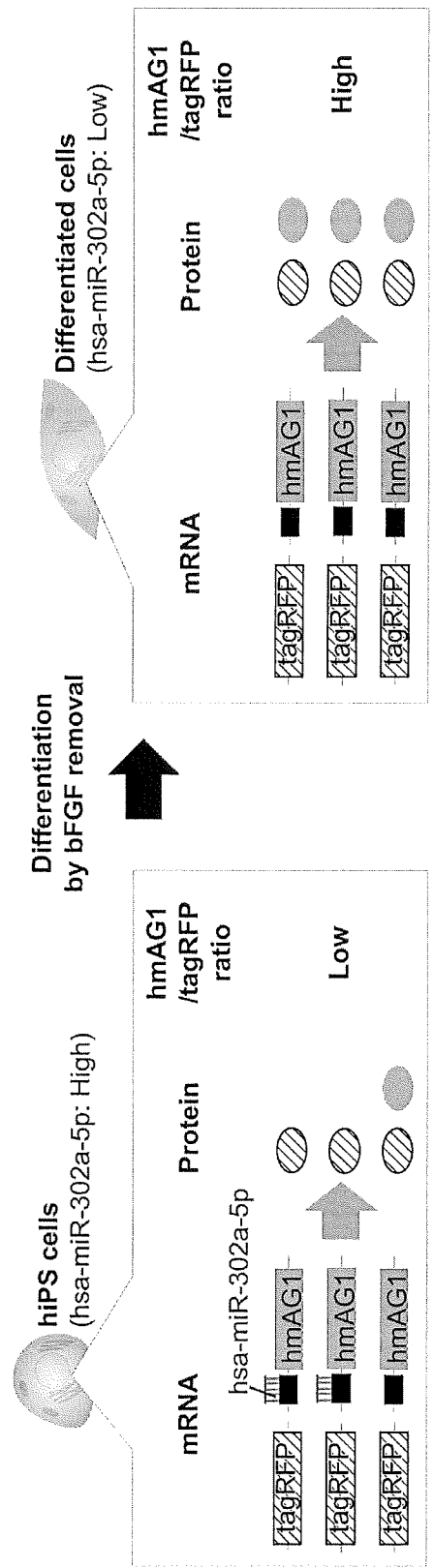
FIG. 3A is a schematic diagram regarding the monitoring during differentiation induced by bFGF removal. The hsa-miR-302a-5p activity was high in undifferentiated iPS cells and low in differentiated cells, causing the hmAG1/tagRFP ratio to increase as differentiation proceeded.

To investigate whether the present miRNA-responsive reporter vector can be used to monitor differentiation-associated miRNA dynamics, stable reporter hiPSCs for hsa-miR-302a-5p were forced to differentiate. Because the level of expression of hsa-miR-302a-5p is high in human pluripotent stem cells and low in differentiated cells (FIG. 9), the expression ratio of hmAG1/tagRFP expressed from the hsa-miR-302a-5p-responsive reporter vector should increase during differentiation (FIG. 3A).

To induce spontaneous differentiation of the stable reporter hiPSCs for hsa-miR-302a-5p, the cells were cultured in bFGF-free medium. It has been known that this culture condition induces the spontaneous differentiation of human pluripotent stem cells. First, the cells were detached from a culture plate at the indicated time points in FIG. 3B, and the levels of expression of the reporter genes were analyzed by flow cytometry. After bFGF removal from the medium, the number of cells exhibiting a high hmAG1/tagRFP ratio increased gradually, and 15 days after the bFGF removal, almost all cells were able to be distinguished from undifferentiated hiPSCs (FIG. 3B). These results are consistent with the past finding that human pluripotent stem cells could completely differentiate two weeks after bFGF removal.

Figure 4A:
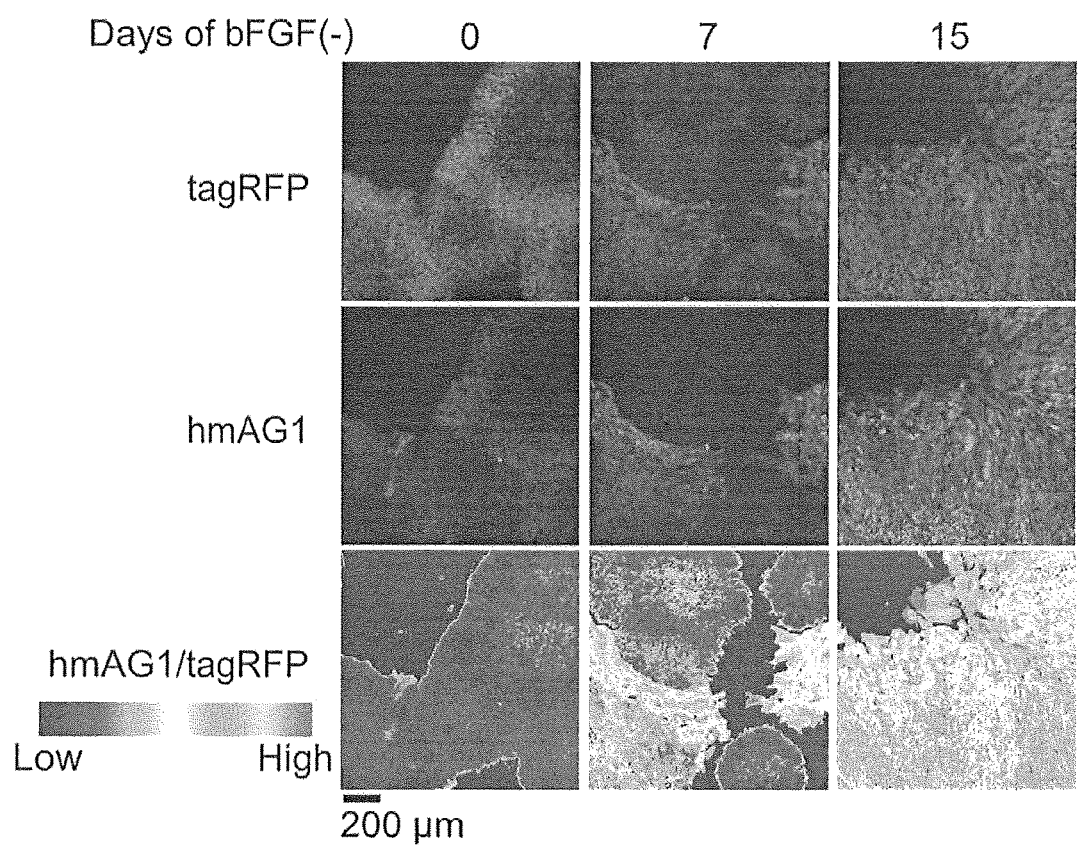
FIG. 4A shows the fluorescent microscopic imaging of hsa-miR-302a-5p activity during differentiation. Stable reporter hiPSCs for hsa-miR-302a-5p were forced to differentiate and their fluorescent microscopic images were captured at the time points indicated above the panels.
Figure 4B:
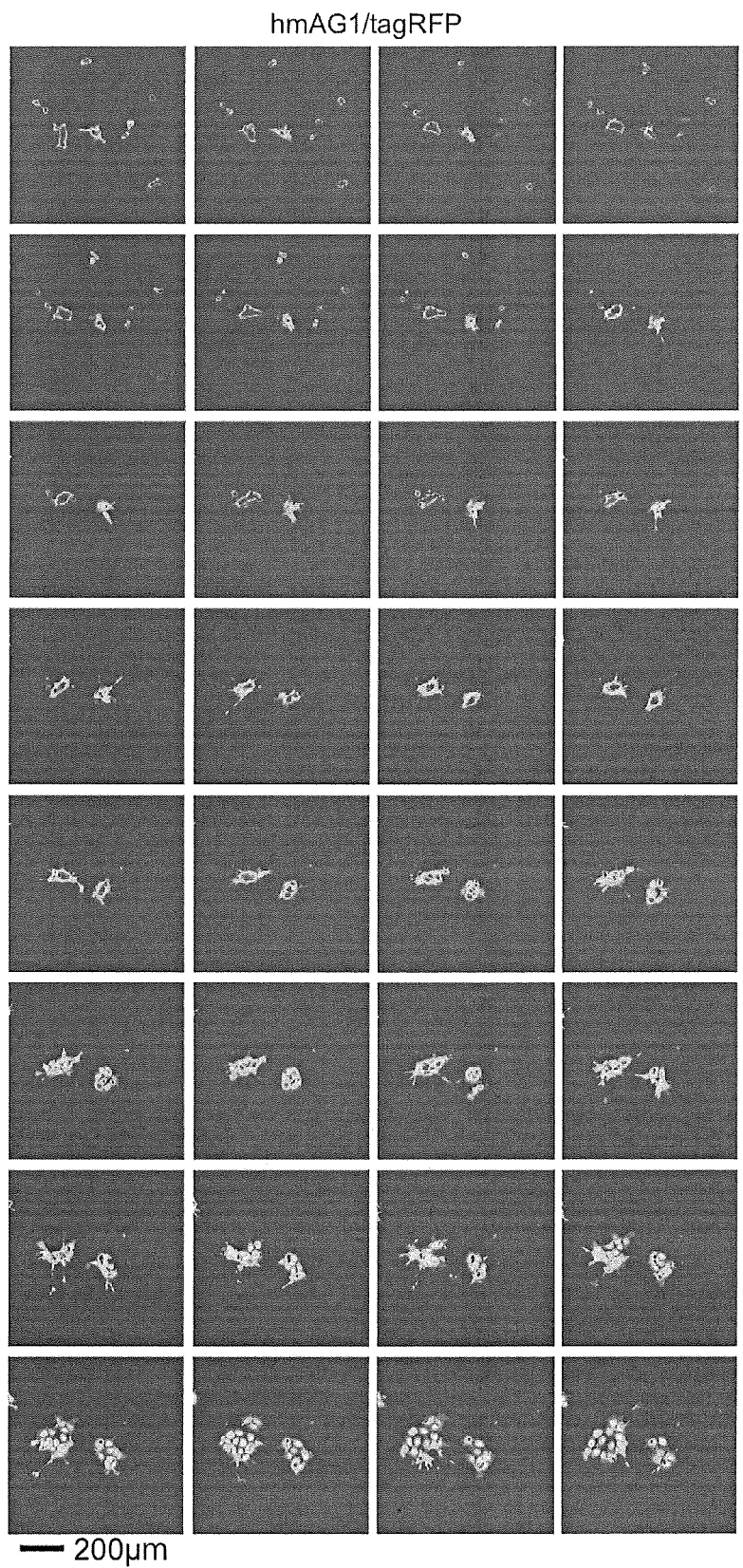
FIG. 4B shows time-lapse imaging of spontaneous differentiation. Stable reporter hiPSCs were cultured in bFGF-free and doxycycline (1000 ng/ml)-containing medium. On day 5, cells were detached from a plate and re-seeded. From days 6 to 11, fluorescent microscopic images were captured every 3 h.
Figure 4C:
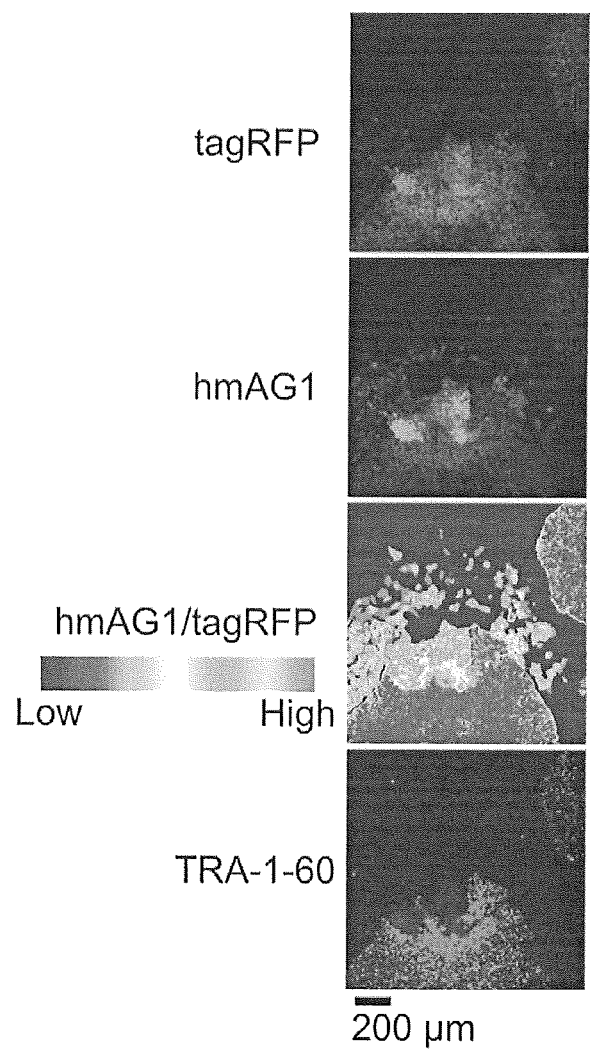
In FIG. 4C, visualized hsa-miR-302a-5p activity and TRA-1-60 staining are compared in cells that contain both undifferentiated hiPSCs and partially differentiating cells.
Figure 4D:
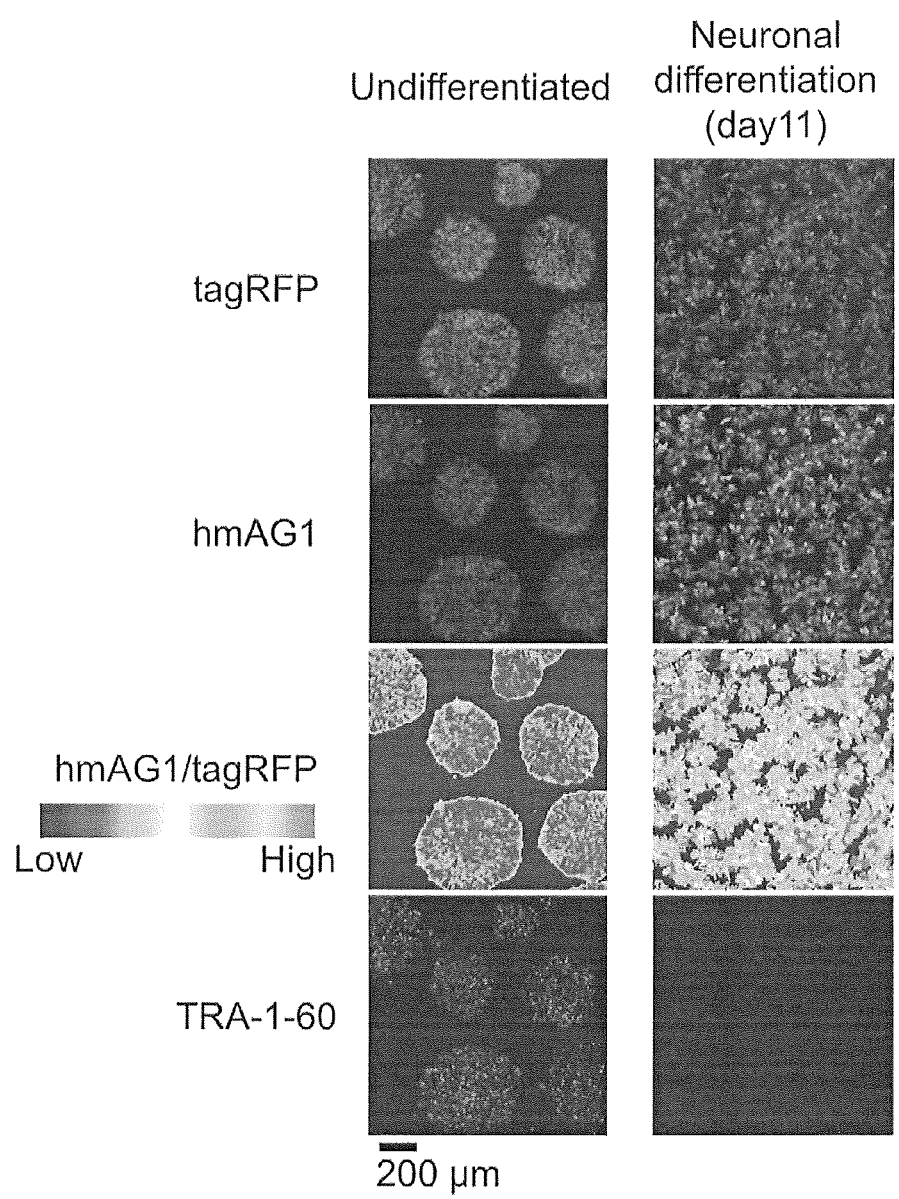
FIG. 4D shows a decrease in hsa-miR-302a-5p activity during neural differentiation. The differentiated cells were detached from a plate, re-seeded, and treated with doxycycline (1000 ng/ml) on day 10. The next day, fluorescent microscopic images were captured. In all the images, the ratio of hmAG1 fluorescence to tagRFP fluorescence was analyzed by ImageJ.
Figure 10A:
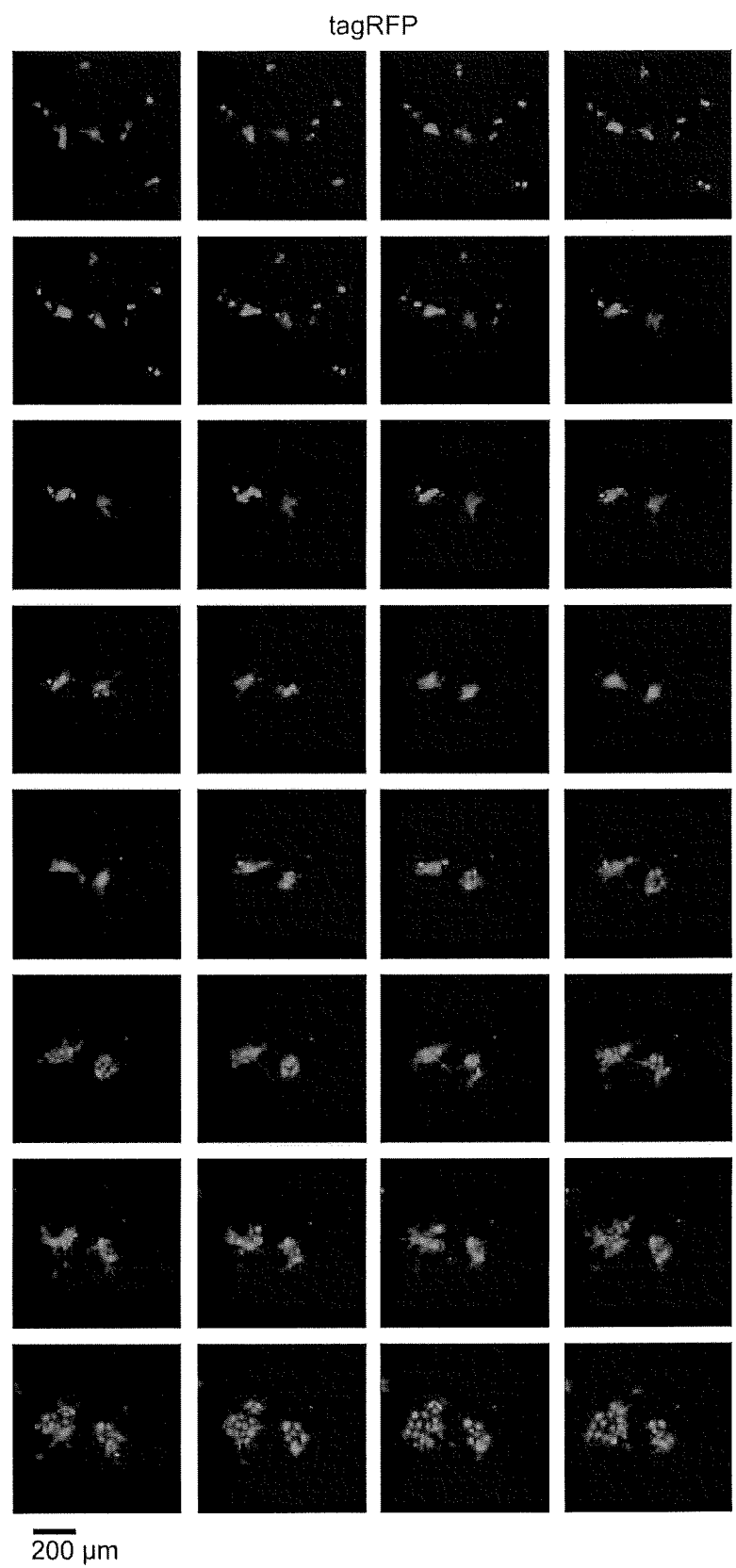
FIG. 10A shows time-lapse imaging of tagRFP.
Figure 10B:
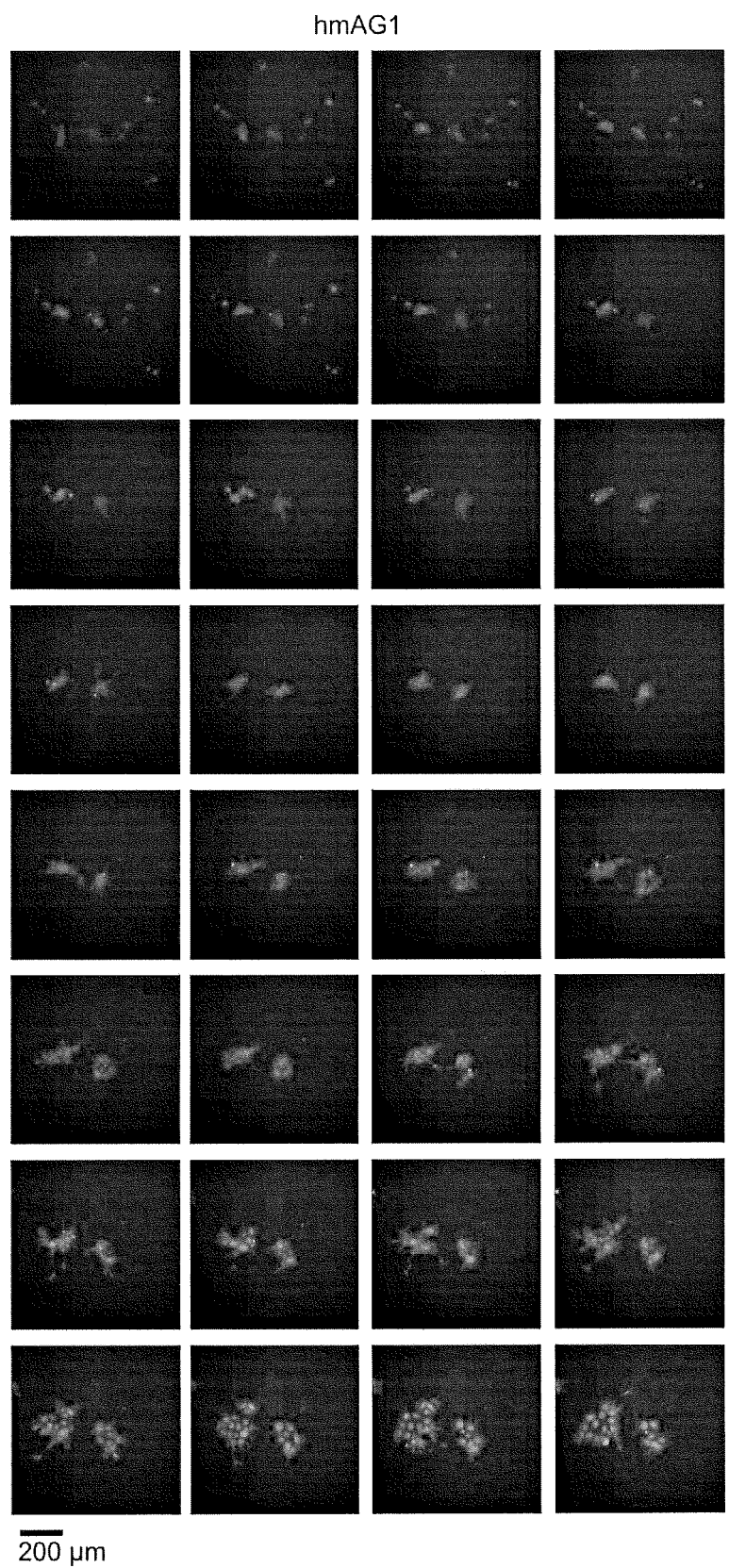
FIG. 10B shows time-lapse imaging of hmAG1.

To investigate whether or not the differentiation could be directly monitored without detaching the cells from a plate, fluorescent microscopic images of the stable reporter hiPSCs were captured. Analysis of the images also showed a gradual increase in the hmAG1/tagRFP ratio after bFGF removal (FIG. 4A), consistent with the flow cytometry data. To observe a differentiation process in more detail, time-lapse imaging was performed (FIGS. 4B, 10A, and 10B). In addition, to confirm that cells showing a low hmAG1/tagRFP ratio were actually undifferentiated cells, the cells were stained with an anti-TRA-1-60 antibody, a marker for pluripotent stem cells. The results revealed that most of the low hmAG1/tagRFP cells were positive for IRA-1-60, while the high hmAG1/tagRFP cells were not (FIGS. 4C and 4D). To investigate the applicability of the reporter system to another differentiation protocol, stable reporter hiPSCs for hsa-miR-302a-5p were forced to differentiate into midbrain neuronal lineage. On day 10 of the differentiation induction, when hsa-miR-302a-5p activity is low, the cells were harvested and re-seeded. Fluorescent microscopic images were captured on the following day. Like the case of differentiation induction by bFGF removal, differentiated cells exhibited a high hmAG1/tagRFP ratio and were negative for TRA-1-60 (FIG. 4D). These results have demonstrated that the present method can be used to check a cellular state and trace the differentiation process.

Figure 11:
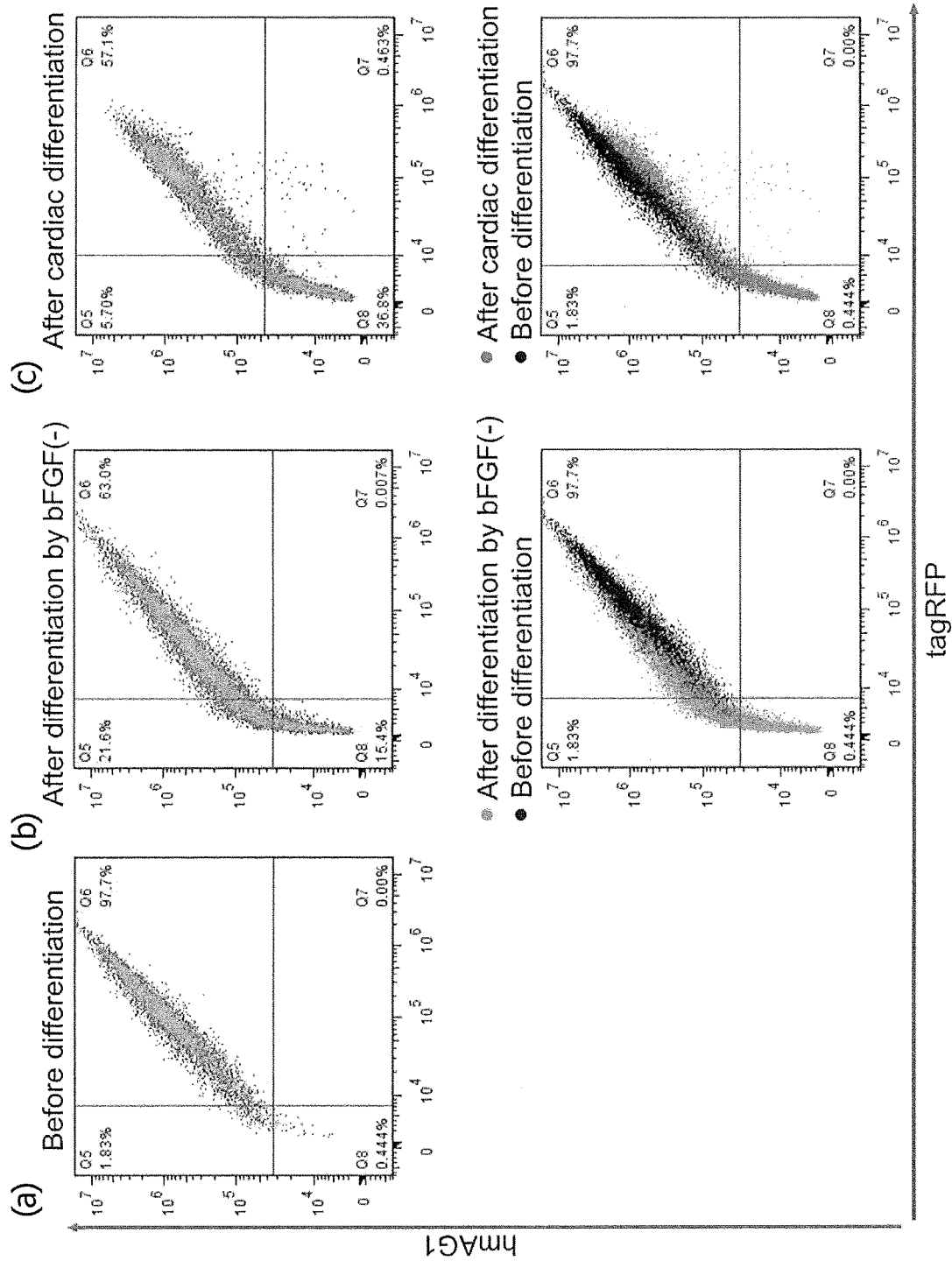
FIG. 11 is 2D dot plots showing the levels of fluorescence of tagRFP and hmAG1 in control stable reporter hiPSCs before and after differentiation. A control vector, which has substantially the same structure as of the miRNA-responsive reporter vector shown in FIG. 2A, but has no miRNA target sequence, was integrated into the genome of an hiPSC (201B7 strain). One day before flow cytometry, these control reporter cells were treated with doxycycline (500 to 1000 ng/ml). Panel (a) shows the results of the control reporter cells before differentiation. Panel (b) shows the results of the control reporter cells at 15 days after bFGF removal. Panel (c) shows the results of the control reporter cells after cardiac differentiation. Regarding the bottom plots (b) and (c), the plot before differentiation is superimposed on each plot after differentiation.

To confirm whether hsa-miR-302a-5p activity controls the hmAG1/tagRFP ratio during differentiation, a control reporter vector without an hsa-miR-302a-5p target sequence was also constructed. Next, hiPSCs that contained this reporter vector were established the same way as in the case of the hsa-miR-302a-5p-responsive reporter vector. The control stable reporter hiPSCs did not exhibit a change in the hmAG1/tagRFP ratio during differentiation (FIG. 11). This result demonstrated that hsa-miR-302a-5p-driven post-transcriptional regulation is responsible for the change in the hmAG1/tagRFP ratio in the stable reporter cells for hsa-miR-302a-5p.

Figure 5A:
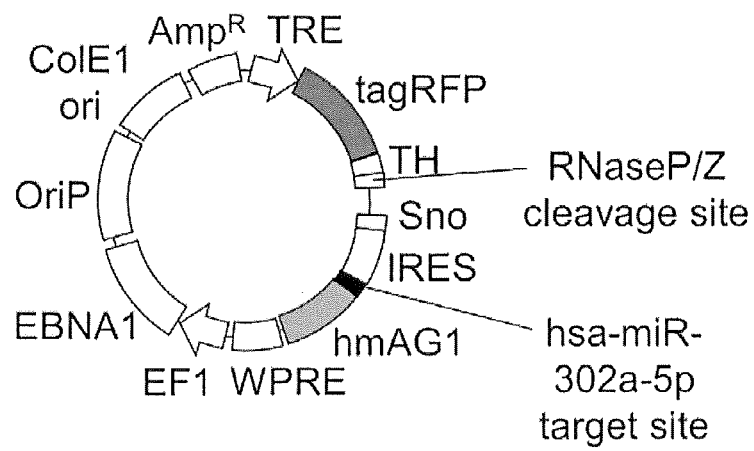
FIG. 5A shows episomal vector constructs. Each abbreviation means as follows: TRE, tetracycline response element for the doxycycline-inducible transcription of tagRFP and hmAG1; tagRFP, tagRFP (red fluorescent protein) gene; TH, MALAT-1 long non-coding RNA-derived triple helix motif for the stabilization and translation of tagRFP messenger RNA; Sno, small nuclear RNA-like long non-coding RNA-derived end protection motif for the stabilization of hmAG1 messenger RNA; IRES, encephalomyocarditis virus-derived internal ribosome entry site for the translation of hmAG1; hmAG1, humanized monomeric Azami Green (green fluorescent protein) gene; WPRE, Woodchuck hepatitis virus Post-transcriptional Regulatory Element for the stabilization and translation of messenger RNA; EF1, elongation factor 1 alpha promoter for the transcription of EBNA1; EBNA1, Epstein-Barr virus Nuclear Antigen 1 gene for the replication of pDNAs containing OriP; OriP, origin for EBNA1-mediated plasmid replications in mammalian cells; ColE1 ori, origin for replication of a plasmid DNA in E. coli; AmpR, ampicillin resistance gene for the selection of E. coli having a plasmid DNA; CAG, CAG promoter composed of cytomegalovirus early enhancer and beta-actin promoter for the transcription of rtTA; rtTA, reverse tetracycline transactivator gene for the doxycycline-inducible transcription by TRE; and puroR, puromycin resistance gene for the selection of mammalian cells.
Figure 5A:
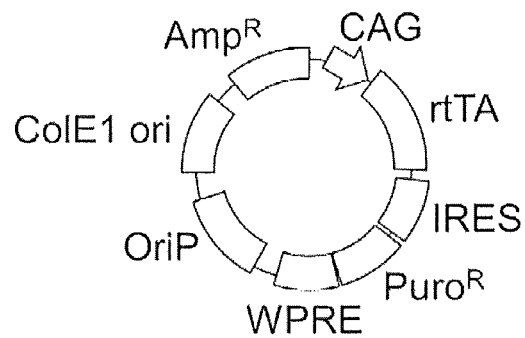
Figure 5B:
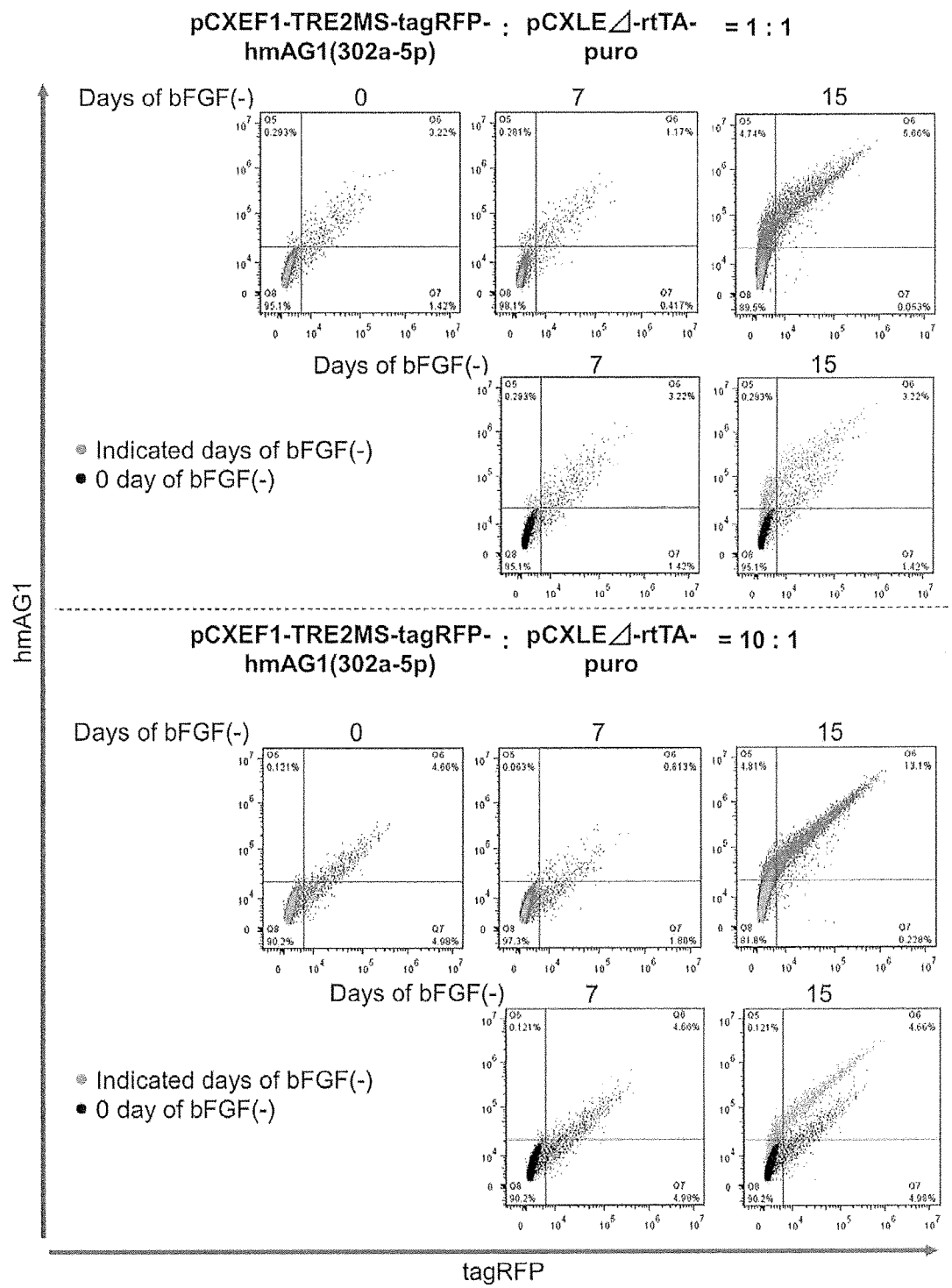
In FIG. 5B, hiPSCs (201B7 strain; $3.3 \times 10^5$ cells) were co-transfected with 333 ng of each of pCXEF1-TRE2MS-tagRFP-hmAG1(302a-5p) and pCXLEΔ-rtTA-puro or with 606 ng of the former and 60.6 ng of the latter in combination. The transfected cells were selected by puromycin and forced to differentiate by bFGF removal. One day before flow cytometry, stable reporter cells were treated with doxycycline (1000 ng/ml). The 2D dot plots show the levels of fluorescence of tagRFP and hmAG1 in hiPSCs transfected with the episomal vectors.
Figure 12:
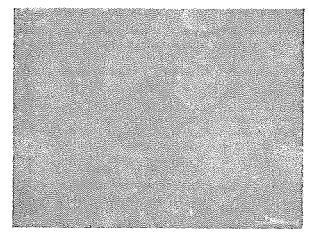
FIG. 12 shows typical photographs of cells obtained by introducing an episomal vector into the cells, followed by puromycin selection. First, hiPSCs were transfected as described in the figure legend of FIG. 5 and selected by puromycin. Then, typical colonies were photographed.
Figure 12:
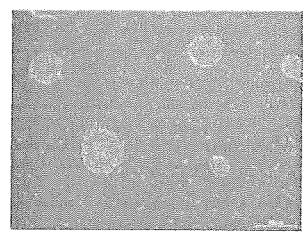

Also, to detect hsa-miR-302a-5p activity, pCXEF1-TRE2MS-tagRFP-hmAG1(302a-5p) and pCXLEΔ-rtTA-puro, which are episomal plasmid-based reporter vectors, were constructed (FIG. 5A). Episomal vectors can be replicated and maintained in human cells without genomic integration. Thus, the present inventors expected that use of these vectors allowed miRNA dynamics to be monitored without a risk of insertional mutagenesis. Here, hiPSCs transfected with the episomal vectors also showed an increased hmAG1/tagRFP ratio after 15 days of bFGF removal, though the number of fluorescent cells was lower than when the piggyBac vector was used. Increasing the ratio of pCXEF1-TRE2MS-tagRFP-hmAG1(302a-5p) to pCXLEΔ-rtTA-puro slightly increased the ratio of fluorescent cells, but decreased the number of puromycin-resistant colonies (FIGS. 5B and 12). In this way, use of the episomal vector-based, miRNA-responsive reporter vector made it possible to clearly distinguish between differentiated cells and undifferentiated hiPSCs (FIG. 5B).

Figure 6A:
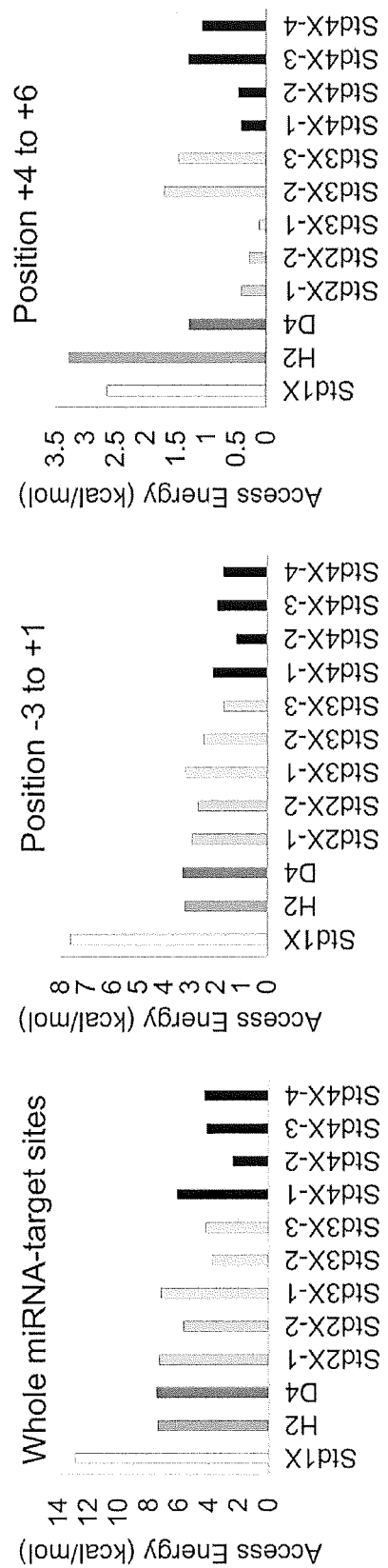
FIG. 6A shows predicted access energies of the hsa-miR-302a-5p target sequences in each vector. For the vectors with multiple hsa-miR-302a-5p target sites, the access energy of each target site is shown individually (e.g., Std4X-3 indicates the access energy of the 3rd target site in the Std4X vector).
Figure 6B:
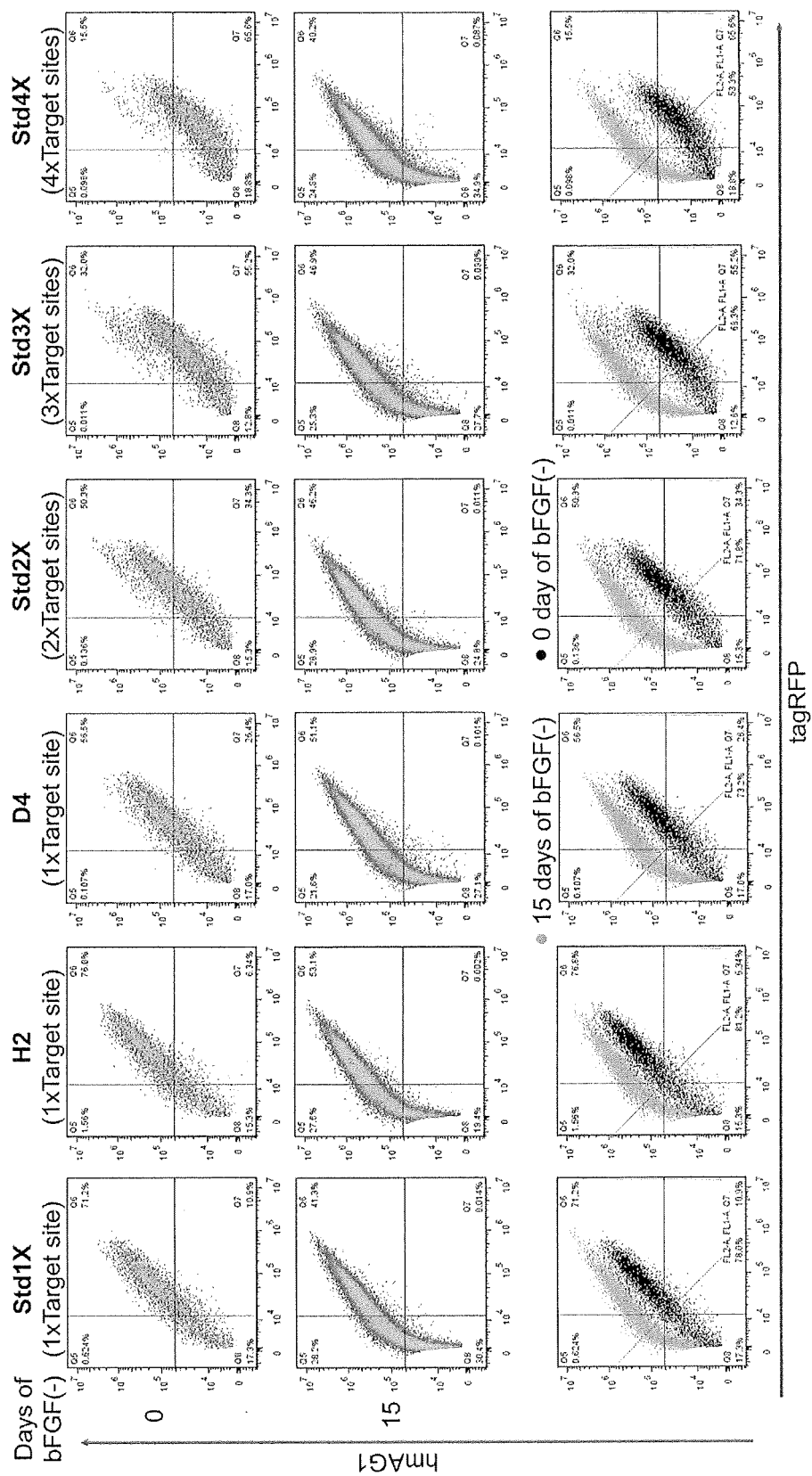
FIG. 6B is 2D dot plots showing the levels of fluorescence of tagRFP and hmAG1 at day 0 (top) and day 15 (middle) after bFGF removal. Regarding the bottom plots, each top plot is superimposed on the corresponding middle plot.
Figure 6C:
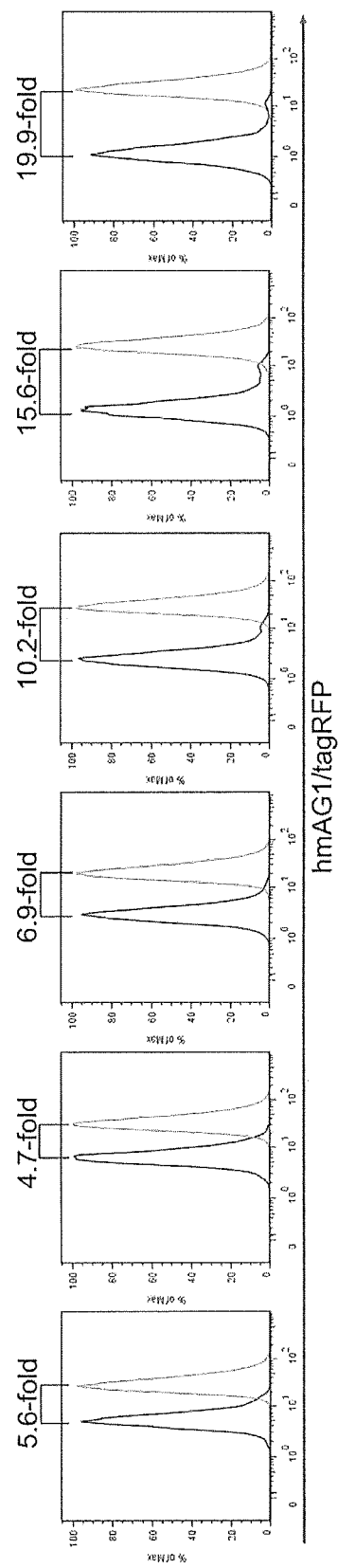
FIG. 6C is histograms showing the hmAG/tagRFP ratio. Fold changes of modes between day 0 and day 15 after the bFGF removal were calculated and shown.
Figure 13A:
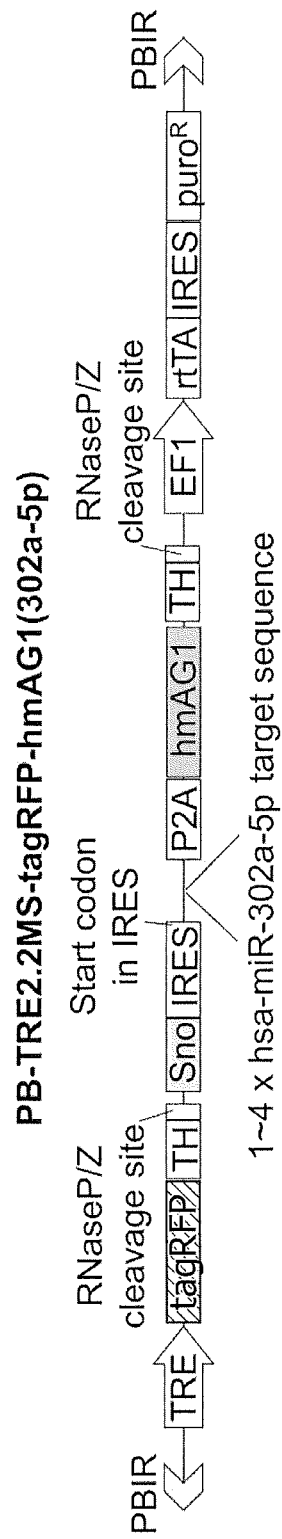
FIG. 13A shows a vector construct having 1 to 4 copies of a hsa-miR-302a-5p target site. Each abbreviation means as follows: PBIR, inverted repeat sequences of the piggyBac transposon for transposase-mediated integration of the reporter genes; TRE, tetracycline response element; tagRFP, tagRFP (red fluorescent protein) gene; TH, MALAT-1 long non-coding RNA-derived triple helix motif for the stabilization and translation of tagRFP messenger RNA; Sno, small nuclear RNA-like long non-coding RNA-derived end protection motif for the stabilization of hmAG1 messenger RNA; IRES, internal ribosome entry site for the translation of hmAG1; P2A, porcine teschovirus-1-derived self-cleaving peptide gene; hmAG1, humanized monomeric Azami Green (green fluorescent protein) gene; EF1, elongation factor 1 alpha promoter for the transcription of rtTA; rtTA, reverse tetracycline trans-activator gene for the doxycycline-inducible transcription by TRE; and puroR, puromycin resistance gene for the selection of mammalian cells having an integrated vector.
Figure 13B:
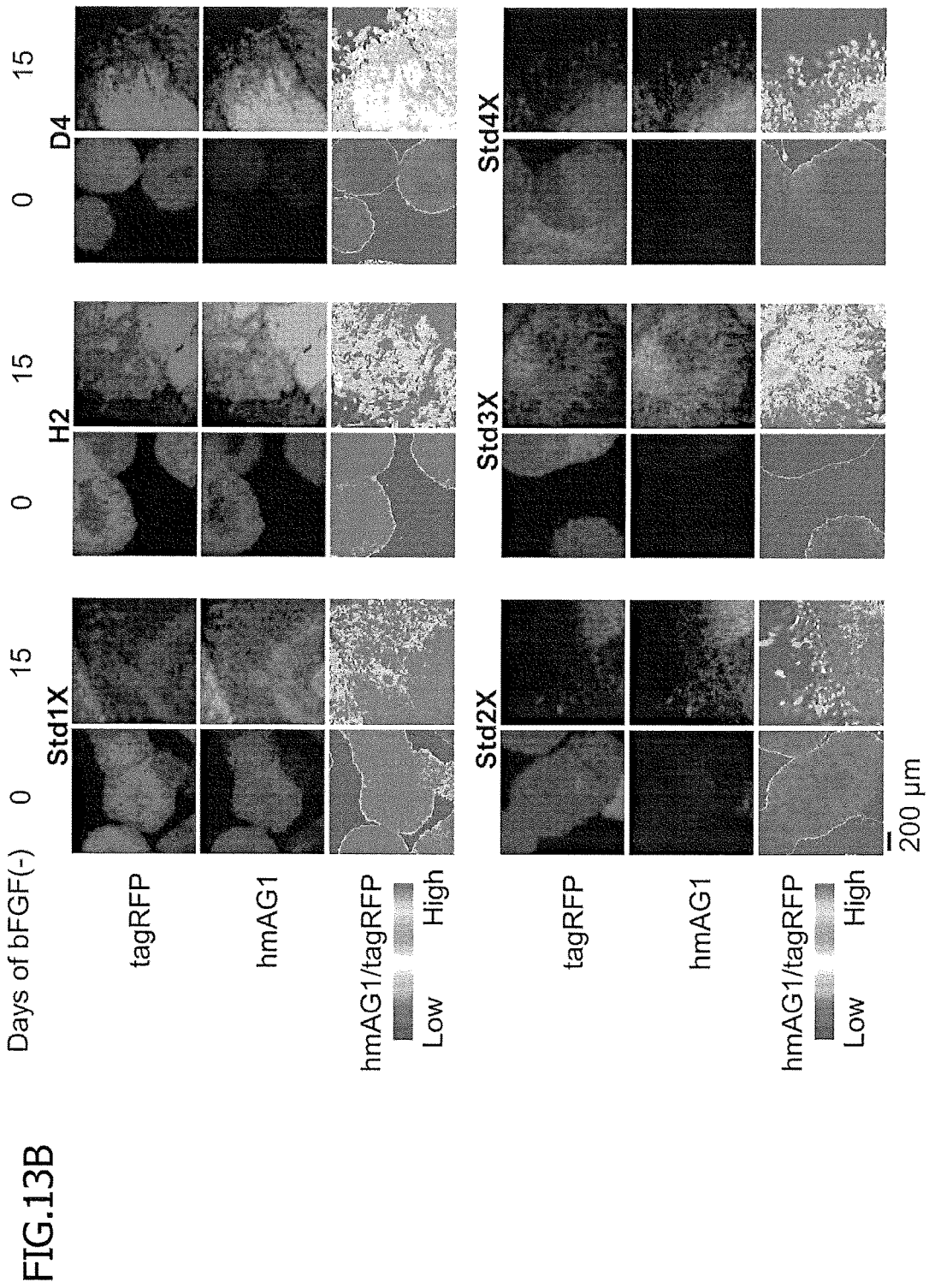
In FIG. 13B, stable reporter hiPSCs for hsa-miR-302a-5p were established using the vector shown in FIG. 13A, and were cultured in bFGF-free medium to induce spontaneous differentiation. Fluorescent microscope images were captured at day 0 or 15 after removal of bFGF from medium, and the hmAG1/tagRFP ratio was analyzed (the bottom panels).

Improvement of miRNA Sensitivity by Reducing Access Energy or Increasing Copy Number of miRNA Target Sites To further increase the miRNA sensitivity, sequences at or near the hsa-miR-302a-5p target sequence were engineered so as to improve accessibility of RISC to the target sequence. For this purpose, the access energy of the hsa-miR-302a-5p target sequence was predicted using ParasoR. Then, 3 kinds of vectors including PB-TRE2.2MS-tagRFP-P2A-hmAG1 (302a-5p)-Std1X, H2, and D4 were constructed (FIG. 13A). Among them, the H2 and D4 vectors were designed such that their access energy was low. However, the Std1X vector was not optimized in such a manner. For recognition of a target sequence by RISC, accessibility of the −3 to +1 region (provided that the 5' end position of a messenger RNA region that binds the miRNA seed region is set to position 0) is the most important, followed by the +4 to +6 region. In view of the above, the H2 vector was designed such that the access energy at the −3 to +1 region is low and the D4 vector was designed such that the access energy at both the −3 to +1 region and the +4 to +6 region was low (FIG. 6A). Each vector was transfected into hiPSCs. Then, the resulting stable reporter cells were spontaneously differentiated by culturing in bFGF-free medium. As a result, the D4 vector showed higher miRNA sensitivity than the Std1X vector, whereas the H2 vector did not (FIGS. 6B and 6C and FIG. 13B).

In addition, PB-TRE2.2MS-tagRFP-P2A-hmAG1(302a-5p)-Std2X, 3X, and 4X, which vectors have multiple (2, 3, or 4) hsa-miR-302a-5p target sequences, were also constructed (FIG. 13A). Each vector was transfected into hiPSCs. Then, the resulting stable reporter cells were spontaneously differentiated by culturing in bFGF-free medium. These vectors showed even higher miRNA sensitivity than the D4 vector, and more hsa-miR-302a-5p target sequences resulted in higher miRNA sensitivity (FIGS. 6B, 6C and 13B). Interestingly, the access energy of all hsa-miR-302a-5p target sequences in the Std2X, 3X, and 4X vectors was lower than that in the Std1X vector, and some of them were even lower than that in the H2 and D4 vectors (FIG. 6A). Thus, the present inventors improved the sensitivity of the miRNA-responsive reporter vectors by reducing the access energy and/or increasing the number of miRNA target sites.

miRNA Activity-Based Sorting of Cardiomyocytes Derived from hiPSCs

To explore the general applicability of the present miRNA-responsive reporter vectors, a reporter vector responsive to a miRNA different from hsa-miR-302a-5p was used to separate and purify specific cells differentiated from hiPSCs. It has been found out that hsa-miR-1-3p (miR-1) activity and hsa-miR-208a-3p (miR-208a) activity are high in cardiomyocytes and low in hiPSCs. Accordingly, the two were chosen as miRNAs used to separate and purify cardiomyocytes, and stable reporter hiPSCs for these miRNAs were established using the piggyBac vectors.

Figure 7A:
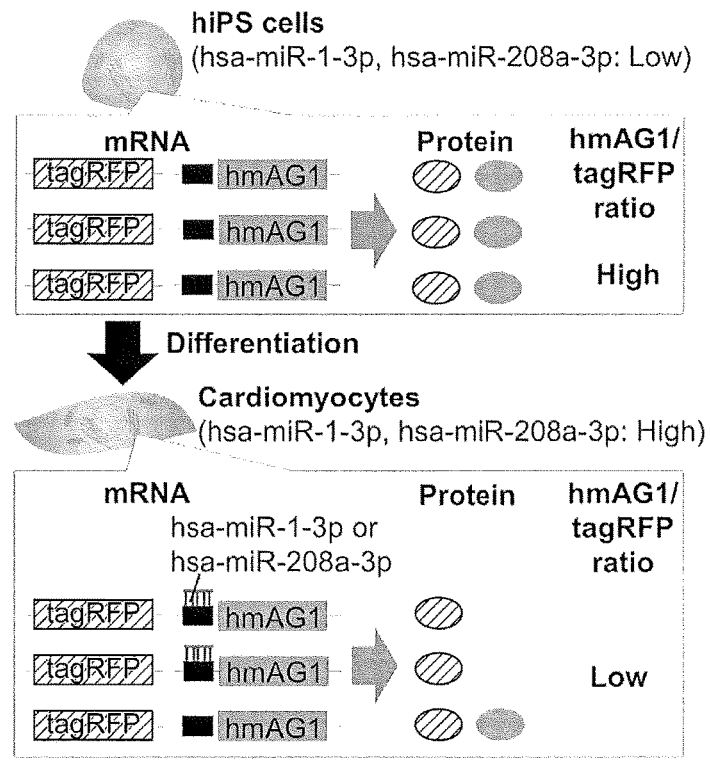
FIG. 7A is a schematic diagram of the monitoring of cardiac differentiation. While hsa-miR-1-3p and hsa-miR-208a-3p activity was low in undifferentiated hiPSCs, their activity was high in cardiomyocytes, causing the hmAG1/tagRFP ratio to decrease as cardiac differentiation proceeded.
Figure 7B:
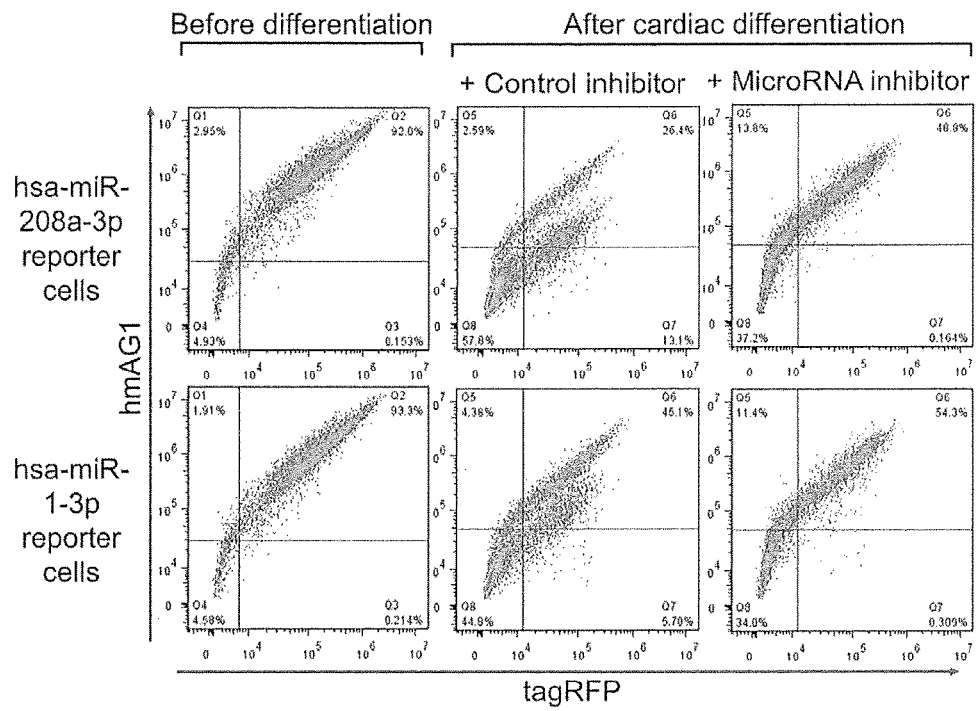
FIG. 7B shows an effect of cardiac differentiation on hsa-miR-208a-3p and hsa-miR-1-3p activity. The levels of fluorescence of tagRFP and hmAG1 in each reporter hiPSC were measured before (left) and after (middle) cardiac differentiation. Some differentiated cells were transfected with an inhibitor for the corresponding miRNA (right).

These stable reporter hiPSCs were forced to differentiate into cardiomyocytes, and a change in the hmAG1/tagRFP ratio was analyzed by flow cytometry. After the induction of cardiac differentiation, both miR-1- and miR-208a-reporter cells were roughly divided into two populations (FIG. 7B). In contrast, control reporter cells, which contained a control reporter vector without the miR-1 or 208a target sequence, showed only one population (FIG. 11). The addition of an miR-1- or miR-208a-specific inhibitor caused the low hmAG1/tagRFP (miR-1/-208a positive) population to disappear (FIG. 7B). Together, these results indicate that miR-1/-208a became active after cardiac differentiation and that the activity of these miRNAs was used to successfully separate the cells into two populations by means of repressed hmAG1 expression.

Figure 7C:
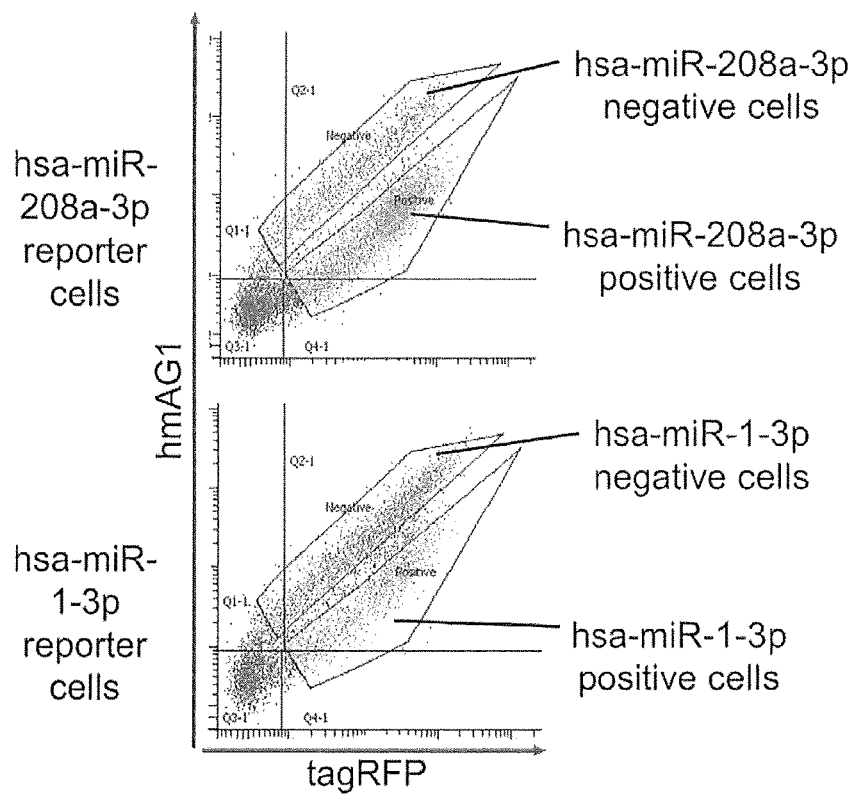
FIG. 7C shows separation and purification of differentiated cells. After differentiation, the levels of fluorescence of tagRFP and hmAG1 were measured with a flow cytometer, and cells that showed a high or low hmAG1/tagRFP ratio were regarded as miRNA negative (purple dots) or positive (green dots) cells, respectively. Each cell population was recovered, and the cTNT expression was analyzed.
Figure 7D:
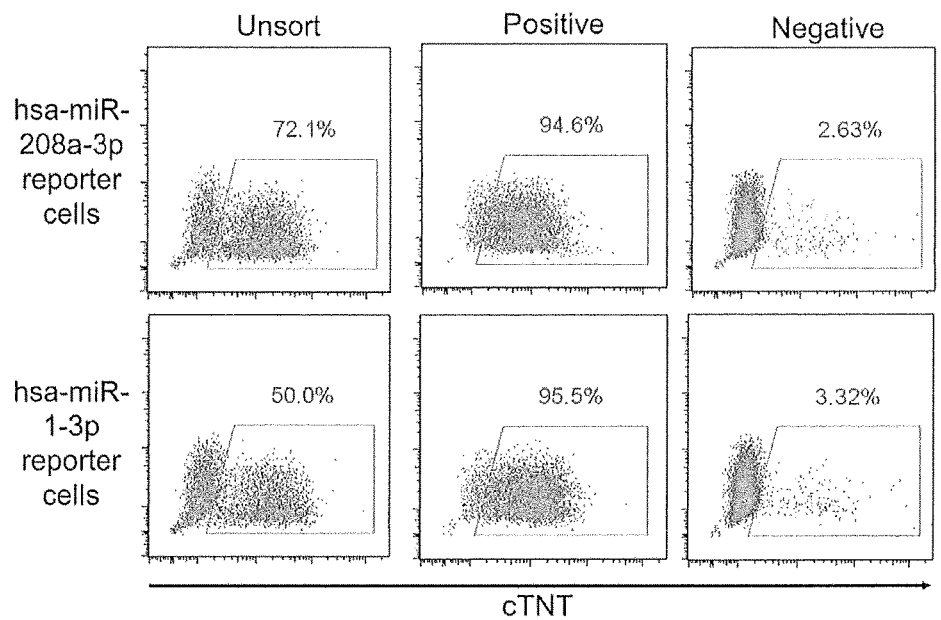
FIG. 7D shows the results obtained by collecting each differentiated cell population and by analyzing the level of expression of cTNT.
Figure 8:
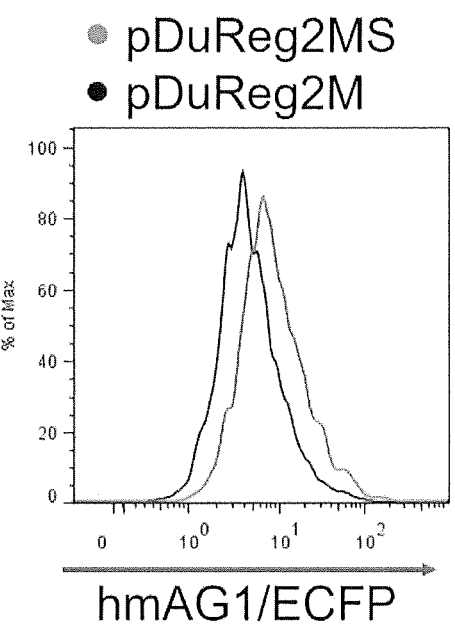
FIG. 8 is histograms illustrating the improvement in the level of expression of hmAG1 after a sno-lncRNA-derived motif was added, and the histograms shown in FIG. 1C are superimposed. Next, 293FT cells were co-transfected with pcDNA3.1-ECFP, hsa-miR-92a-3p inhibitor, and pDuReg2MS-tagRFP-hmAG1(92a-3p) or pDuReg2M-tagRFP-hmAG1(92a-3p). Then, the levels of fluorescence were analyzed as described in the figure legend of FIG. 2. The magenta histogram and the black histogram correspond to the cells containing pDuReg2MS-tagRFP-hmAG1(92a-3p) and the cells containing pDuReg2M-tagRFP-hmAG1(92a-3p).

Finally, to investigate whether the low hmAG1/tagRFP cell population actually contained cardiomyocytes, the high and low hmAG1/tagRFP cells were separated and purified. The level of expression of cardiac troponin T (cTNT), which is a marker for cardiomyocytes, in these cells were analyzed (FIGS. 7C and 7D). The results show that more than 90% of the low hmAG1/tagRFP population was cTNT positive while only less than 5% of the high hmAG1/tagRFP population was (FIG. 7D). The analysis of the fluorescent microscopic imaging also demonstrated that cTNT positive cells had a low hmAG1/tagRFP ratio (FIG. 14). These results indicate that the miR-1- and miR-208a-reporter cells can be used for detection, and separation and purification of cardiomyocytes without additional transfection or cell staining.

Discussion

This study reports novel miRNA-responsive reporter vectors that enable the continuous monitoring and visualization of miRNA dynamics in live differentiating cells and the separation and purification of specific differentiated cells (i.e., cardiomyocytes herein) derived from hiPSCs. In contrast to previous miRNA reporter vectors, the present miRNA reporter vectors were designed to distinguish between transcriptional repression and miRNA-mediated post-transcriptional repression by having the miRNA-responsive and reference reporter genes transcribed from a single promoter. The distinction of miRNA-mediated repression from transcriptional repression is especially important when differentiation-associated miRNA dynamics is monitored, because transgenes tend to be transcriptionally silenced during differentiation. In fact, upon spontaneous differentiation, many cells showed lower hmAG1 expression on day 7 than on day 0 (FIG. 3B), while hsa-miR-302a-5p expression levels remained essentially unchanged (FIG. 9). In contrast to the absolute hmAG1 expression level, the hmAG1/tagRFP ratio in the major population was similar on days 0 and 7 (FIG. 3B), indicating that the hmAG1/tagRFP ratio is a better indicator of miRNA activity than absolute hmAG1 expression level.

When integrative vectors such as piggyBac or lentivirus are used to prepare the miRNA-responsive reporter, genomic sequences surrounding the integration sites could affect the transcription of the reporter genes. These surrounding sequences may contain transcription start sites or enhancers, especially when viral vectors are used to show distinct integration site preferences for active endogenous genes. When a vector is designed such that a miRNA-responsive reporter gene and a reference reporter gene are transcribed from separate promoters, the two promoters differ in their orientation or distance from the surrounding genomic enhancers, the activity of which can change during differentiation. This change can subsequently change the expression ratio of the miRNA-responsive reporter gene to the reference reporter gene. In contrast, there is no such concern in the present vector design because the two reporter genes are transcribed from the identical promoter.

The present inventors evaluated miRNA activity by observing the expression ratio of the miRNA-responsive reporter gene to the reference reporter gene. The present inventors believe that the expression ratio can provide more sensitive and accurate information on miRNA activity than the level of expression per se of the miRNA-responsive reporter gene. Supporting this notion, the present vectors were used to detect hsa-miR-302a-5p (for hiPSCs detection), miR-1 or miR-208a (for cardiomyocytes detection) activity by using only one copy of the miRNA target site (FIGS. 3, 4, 5, and 6). Here, only one copy of a miRNA target site is necessary. Thus, the miRNA-responsive reporter vectors for the miRNAs of interest can be constructed by simply inserting the site-containing short (around 24 bp) oligo DNA into a cloning site located between the IRES and hmAG1. In addition, the miRNA sensitivity can be increased by optimizing the surrounding sequences to reduce the access energy or by increasing the copy number of the miRNA target sites (FIGS. 6 and 13). Such optimizations may enable the detection of miRNAs with lower activity than hsa-miR-302a-5p, miR-1, or miR-208a in the target cells.

For long-term vector maintenance in living cells, piggyBac or episomal-based, non-viral plasmid vectors were used. The preparation of these plasmid vectors is much easier than that of viral vectors. In addition, transgenes integrated by piggyBac vectors can be removed from genomes by re-transfection of a piggyBac transposase expression vector. Episomal vectors can be more easily removed by just culturing in the absence of drug selection. Accordingly, when use of separated and purified cells requires avoidance of influences by reporter genes, the reporter genes can be removed, which is a feature distinct from retro- or lenti-viral vectors.

Although episomal vectors are replicated and maintained even in dividing cells, it has been reported that 16% of copies of an episomal vector do not replicate in each cell cycle. Hence, episomal reporter vectors can decrease relatively rapidly in highly proliferating cells. Indeed, 80% of cells transfected with the present episomal vector set (pCXEF1-TRE2MS-tagRFP-hmAG1(302a-5p) and pCXLEΔ-rtTA-puro) did not show fluorescence, although the cells were continuously selected by puromycin (FIG. 5). This low ratio of fluorescent cells under puromycin selection may be due to the proliferation of cells containing only pCXLEΔ-rtTA-puro. These results indicate that piggyBac vectors are more suitable for highly proliferating cells than episomal vectors.

To monitor differentiation, conventionally used is a technique by which a reporter gene is knocked-in to a cell type-specific endogenous gene. Although recent developments in CRISPR/Cas9 technology has made gene knock-in easier, this approach still needs to design and validate both the guide RNAs and homology arms for each target gene. In addition, because knock-in into off-target sites can result in differentiation state-independent expression of the reporter genes, reporter cells should be cloned and checked to confirm off-target integrations do not occur. In contrast, the present dual reporter vector system should not be susceptible to the transcriptional variability caused by differences in copy numbers or integration sites (FIGS. 2C to 2E), because the present vectors can be used to distinguish between transcriptional regulation and miRNA-mediated post-transcriptional repression. Because of this, the stable miRNA responsive reporter cells in this study can be used to monitor miRNA dynamics without cell cloning. In fact, the stable reporter hiPSCs for miR-1 or miR-208a were used without their cloning, but it was still possible to detect and separate and purify cardiomyocytes (FIG. 7). This advantage of the present miRNA-responsive reporter system can save time and labor. A report shows that a dual reporter system consisting of constitutive and cell-specific promoters was previously used to monitor differentiation. However, such a system may not be suitable for integrative vectors, because genomic sequences surrounding the integration sites could affect the transcriptional property of cell type-specific promoters.

Different from the messenger RNA transfection-based, miRNA detection method, the miRNA-responsive reporter vectors in this study have a risk of insertional mutagenesis. Thus, for clinical applications that need a strictly low risk of mutagenesis, messenger RNA transfection-based methods are more suitable. However, messenger RNA transfection-based methods require optimization of the transfection condition for each cell type. In addition, the methods are not suitable for visualizing miRNA dynamics during differentiation, because repetitive RNA transfection and cell detachment as required for the messenger RNA transfection may damage and change the cell state. In contrast, the DNA-based reporter vectors developed in this study enable continuous monitoring and visualization of miRNA dynamics without repetitive transfection or cell detachment from the plate (FIG. 4). Accordingly, once the reporter stem cells are stably established, the cells can be repeatedly used to monitor and visualize miRNA dynamics during differentiation. Additionally, cell differentiation protocols often require cell-cell interactions. When the cells containing a DNA-based miRNA reporter vector are used, unlike the messenger RNA transfection-based method, no dissociation from surrounding cells is needed. Due to this, the cells are applicable in monitoring differentiation under conditions in which the cell-cell interactions are necessary. In view of the above, for non-clinical applications, the present stable reporter cells are convenient for both monitoring and separating and purifying target differentiated cells. This feature is also advantageous compared with conventional cell purification methods that use antibodies, because the present reporter vectors are more cost effective.

Cells containing the present reporter vector can be used for preclinical studies to check the therapeutic efficacy in animal disease models. Sorted differentiated cells can also be used to test drug efficacy and safety on specific cells. In addition, there are various applications to monitor differentiation by using integrative vectors. For example, this approach simplifies the screening of conditions that induce differentiation into specific target cells. Because miRNA activity changes during not only differentiation but also reprogramming and carcinogenesis, the miRNA reporter vectors can also be used to screen for genes that contribute to these cellular phenomena.

The present system may be improved in the future to expand its utility and usage. For example, addition of a destabilization domain (e.g., PEST peptide) to a fluorescent protein may make it possible to accurately measure real-time miRNA activity, as the addition of the domain can cause a decrease in the level of the residual fluorescent protein produced previously. In the present study, each reporter cell was used to monitor the dynamics of only one miRNA. However, it is possible to monitor the dynamics of multiple miRNAs in a single cell by increasing the variety of the fluorescent proteins. In addition, miRNA dynamics was monitored during the differentiation process in vitro but not in vivo. In vivo application is difficult because of the complexity of delivering reporter vectors to target cells. However, ex vivo transfection and transplantation of stem or precursor cells or the establishment of transgenic reporter animals could solve this problem. Lastly, while green and red fluorescent proteins were used in the present study, far-red or infrared fluorescent proteins, which show high tissue penetration, may be more suitable for in vivo use. There is a report showing a technique for detecting a fluorescent protein located deep in a living body. It is worth trying to incorporate such a technique into the present system.

The present non-viral vectors with single promoter-driven, dual reporter genes enable the continuous monitoring and visualization of differentiation-associated miRNA dynamics and the purification of specific differentiated cells. Using miRNA-responsive reporter piggyBac or episomal vectors, stable reporter cells can be easily established. Neither the monitoring of differentiation nor the purification of specific cells by using these stable reporter cells needs cell cloning, repeated transfection, or antibodies. In addition, these stable reporter cells can be used to monitor the cellular changes that occur during cell reprogramming or cancer development. The present miRNA-responsive reporter vectors will therefore facilitate studies regarding the various cellular changes associated with miRNA dynamics.

What is claimed is:

1. A vector comprising:
   (I) 5'- and 3'-end nucleic acid sequences for integration to be recognized by a transposase, and
   (II) a reporter gene sequence positioned between the 5'- and 3'-end nucleic acid sequences for integration, the reporter gene sequence comprising: in this order in the 5' to 3' direction, a) an inducible promoter; b) a sequence encoding a first marker protein; c) a poly(A) substitute sequence; d) an RNaseP/Z cleavage site sequence; e) an mRNA-stabilizing sequence; f) a sequence to drive polycistronic expression; g) an miRNA target sequence; h) a sequence encoding a second marker protein; i) a poly(A) substitute sequence and an RNaseP/Z cleavage site sequence, or a poly(A) signal sequence; and j) a sequence encoding an activator for the inducible promoter.

2. The vector according to claim 1, wherein the reporter gene sequence further comprises k) a strong expression promoter linked on the 3' end side of i) the poly(A) substitute sequence and RNaseP/Z cleavage site sequence, or poly(A) signal sequence, and on the 5' end side of j) the sequence encoding an activator for the inducible promoter.

3. The vector according to claim 1, wherein the reporter gene sequence further comprises, in this order in the 5' to 3' direction, l) a sequence to drive polycistronic expression; and m) a drug resistance sequence, linked on the 3' end side of j) the sequence encoding an activator for the inducible promoter.

4. A cell stably expressing a miRNA-responsive mRNA, wherein the cell has introduced therein:
   the vector according to claim 1 and a transposase or a vector encoding the transposase.

5. A method for visualizing a differentiation status of a cell, the method comprising the steps of:
   (I) introducing, into the cell, the vector according to claim 1 and a transposase or a vector encoding the transposase; and
   (II) determining the differentiation status of the cell by using, as indicators, a level of translation of the first marker protein and a level of translation of the second marker protein.

6. The method according to claim 5, wherein the cell is a cell differentiated from a pluripotent stem cell.

7. The method according to claim 5, wherein the introduction step comprises introducing, into a cell population, the vector and a transposase or a vector encoding the transposase; and
   wherein the method further comprises, after the cell differentiation status determination step, (III) introducing, into the cell population, the transposase or the vector encoding the transposase, thereby removing the reporter gene sequence from a genome of the cell.

* * * * *

UNITED STATES PATENT AND TRADEMARK OFFICE
CERTIFICATE OF CORRECTION

Page 1 of 2

PATENT NO. : 10,378,070 B2
APPLICATION NO. : 15/697831
DATED : August 13, 2019
INVENTOR(S) : Saito et al.

It is certified that error appears in the above-identified patent and that said Letters Patent is hereby corrected as shown below:

In the Specification

Column 10, Line 8, SEQ ID NO:1:
Please correct "ttttgttttctcaggattgcttttggcctttccctagctttaaaaaaa"
to read -- ttttgttttctcaggttttgcttttggcctttccctagctttaaaaaaa --

Column 10, Line 17, SEQ ID NO:2:
Please correct "gcggtgtattgctt"
to read -- gcggtgtctttgctt --

Column 17, Line 67, SEQ ID NO:11:
Please correct "gagaaaacaaccttttgttttctcaggttttgctttggcctttccctag ctt-"
to read -- gagaaaacaaccttttgttttctcaggttttgcttttggcctttccctagctt- --

Column 18, Line 47, SEQ ID NO:17:
Please correct "gaac tgaggtccaT"
to read -- gaactgaggtccaT --

Column 18, Line 49, SEQ ID NO:18:
Please correct "gagttttcactcattttgttcagcttccaaggaatgtatatatggaagtcat catc-"
to read -- gagttttcactcattttgttcagctttccaaggaatgtatatatggaagtcatcatc- --

Column 21, Line 14, SEQ ID NO:35:
Please correct "CACGTCTCCAGCCTGCTTCAGCA GGCTGAAGT-"
to read -- CACGTCTCCAGCCTGCTTCAGCAGGCTGAAGT- --

Column 21, Line 41, SEQ ID NO:40:
Please correct "GAGCAAGTACATCCACGTTTAAGTGTGT ACCTCGT-"
to read -- GAGCAAGTACATCCACGTTTAAGTGTGTACCTCGT- --

Signed and Sealed this
Fourth Day of February, 2020

Andrei Iancu
*Director of the United States Patent and Trademark Office*

CERTIFICATE OF CORRECTION (continued)
U.S. Pat. No. 10,378,070 B2

Column 21, Line 44, SEQ ID NO:41:
Please correct "GAAGCAAGTACATCCACGTT TAAGTCGCTTCCGT-"
to read -- GAAGCAAGTACATCCACGTTTAAGTCGCTTCCGT- --

Column 23, Line 32:
Please correct "500 of" to read -- 500 µl/well of --

Column 31, Line 2:
Please correct "IRA-1-60" to read -- TRA-1-60 --